US009550016B2

(12) United States Patent
Gifford

(10) Patent No.: US 9,550,016 B2
(45) Date of Patent: Jan. 24, 2017

(54) PASSIVE SEPARATION OF WHOLE BLOOD

(71) Applicant: Halcyon Biomedical, Incorporated, Friendswood, TX (US)

(72) Inventor: Sean C. Gifford, Ft. Edward, NY (US)

(73) Assignee: Halcyon Biomedical, Incorporated, Friendswood, TX (US)

( * ) Notice: Subject to any disclaimer, the term of this patent is extended or adjusted under 35 U.S.C. 154(b) by 0 days.

(21) Appl. No.: 14/601,220

(22) Filed: Jan. 20, 2015

(65) Prior Publication Data

US 2015/0202356 A1    Jul. 23, 2015

Related U.S. Application Data

(60) Provisional application No. 61/929,357, filed on Jan. 20, 2014.

(51) Int. Cl.
*A61M 1/02* (2006.01)
*A61M 1/36* (2006.01)
(Continued)

(52) U.S. Cl.
CPC .......... *A61M 1/0272* (2013.01); *A61M 1/3672* (2013.01); *A61M 1/3695* (2014.02);
(Continued)

(58) Field of Classification Search
CPC  A61M 1/0272; A61M 1/3695; A61M 1/3672; A61M 2202/0415; A61M 2202/0427; A61M 2202/0429; A61M 2202/0439; B01D 21/006; B01D 21/2444; B01D 21/28
See application file for complete search history.

(56) References Cited

U.S. PATENT DOCUMENTS

| | | | |
|---|---|---|---|
| 5,427,663 | A | 6/1995 | Austin et al. |
| 5,456,824 | A | 10/1995 | Misumi et al. |

(Continued)

FOREIGN PATENT DOCUMENTS

| | | |
|---|---|---|
| EP | 0882464 A2 | 12/1998 |
| JP | 2005124813 A | 5/2005 |

OTHER PUBLICATIONS

Hou, et al. "Microfluidic Devices for Blood Fractionation," Micromachines, 2011, vol. 2, pp. 319-343.
(Continued)

*Primary Examiner* — J. Christopher Ball
(74) *Attorney, Agent, or Firm* — Boulware & Valoir

(57) ABSTRACT

Described are systems, methods, and kits for compression sedimentation and whole blood separation. For example, a compression sedimentation system may include a compression stage configured to accept a flexible reservoir configured to contain a liquid mixture. The compression stage may include a base substrate and a compression substrate configured to apply a force to the flexible reservoir effective to create a pressure in the liquid mixture. An apparatus for whole blood separation may include a sedimentation system that separates whole blood into a supernatant including platelet rich plasma and a subnatant including red blood cells. At least one platelet-concentrating device may be included to receive the supernatant including the PRP and to separate a platelet concentrate and a platelet poor plasma from the supernatant.

30 Claims, 33 Drawing Sheets

(51) Int. Cl.
B01D 21/24 (2006.01)
B01D 21/28 (2006.01)
B01D 21/00 (2006.01)

(52) U.S. Cl.
CPC ....... *B01D 21/006* (2013.01); *B01D 21/2444* (2013.01); *B01D 21/28* (2013.01); *A61M 2202/0415* (2013.01); *A61M 2202/0427* (2013.01); *A61M 2202/0429* (2013.01); *A61M 2202/0439* (2013.01)

(56) References Cited

U.S. PATENT DOCUMENTS

| | | | |
|---|---|---|---|
| 5,632,906 | A | 5/1997 | Ishida et al. |
| 2006/0118479 | A1 | 6/2006 | Shevkoplyas et al. |
| 2007/0092509 | A1* | 4/2007 | Mittra ............... A61M 1/3472 424/140.1 |
| 2007/0160503 | A1 | 7/2007 | Sethu et al. |
| 2007/0282242 | A1 | 12/2007 | Gibbs et al. |
| 2008/0023399 | A1 | 1/2008 | Inglis et al. |
| 2008/0050275 | A1* | 2/2008 | Bischof ............... A01N 1/02 422/32 |
| 2013/0168298 | A1 | 7/2013 | Huang et al. |
| 2013/0226150 | A1 | 8/2013 | Nash et al. |

OTHER PUBLICATIONS

Gossett, et al. "Label-free Cell Separation and Sorting in Microfluidic Systems," Anal. Bioanal. Chem., 2010, v. 397, pp. 3249-3267.
Sethu, et al. "Microfluidic Diffusive Filter for Apheresis (Leukapheresis)," Lab Chip, 2006, v. 6, pp. 83-89.
Gifford, et al. "Controlled Incremental Filtration: A Simplified Approach to Design and Fabrication of High-Throughput Microfluidic Devices for Selective Enrichment of Particles," Lab Chip, 2014, v. 14, pp. 4496-4505.
Chen, et al. "Microfluidic Chip for Blood Cell Separation and Collection Based Crossflow Filtration," Sens. Actuators, B, 2008, v. 130, pp. 216-221.
Yung, et al. "Micromagnetic-Microfluidic Blood Cleansing Device," Lab Chip, 2009, v. 9, pp. 1171-1177.
Shevkoplyas, et al. "Biomimetic Autoseparation of Leukocytes from Whole Blood in Microfluidic Device," Anal. Chem., 2005, v. 77, pp. 933-937.
Zhang, et al. "Effect of Exposure Dose on the Replication Fidelity and Profile of Very High Aspect Ratio Microchannels in SU-8," Lab Chip, 2004, v. 4, pp. 646-653.
Tanyeri, et al. "A Microfluidic-based Hydrodynamic Trap: Design and Implementation," Lab Chip, 2011, v. 11, pp. 1786-1794.
Kersaudy-Kerhoas, et al. "Micro-scale Blood Plasma Separation: From Acoustophoresis to Egg-beaters," Lab Chip, 2013, v. 13, pp. 3323-3346.
Yamada, et al. "Hydrodynamic Filtration for On-Chip Particle Concentration and Classification Utilizing Microfluidics," Lab Chip, 2005, v. 5, pp. 1233-1239.
Yamada, et al. "Pinched Flow Fractionation: Continuous Size Separation of Particles Utilizing a Laminar Flow Profile in a Pinched Microchannel," Anal. Chem., 2004, v. 76, pp. 5465-5471.
Zhao, et al. "Shear-induced Particle Migration and Margination in a Cellular Suspension," Phys. Fluids, 2012, v. 24, pp. 011902-1-011902-21.
Quek, et al. "Separation of Deformable Particles in Deterministic Lateral Displacement Devices," Phys. Rev. E: Stat., Nonlinear, Soft Matter Phys., 2011, v. 83, pp. 056301-1-056301-7.
Inglis, et al. "A Scalable Approach for High Throughput Branch Flow Filtration," Lab Chip, 2013, v. 13, pp. 1724-1731.
Zhang, et al. "An All-in-One Microfluidic Device for Parallel DNA Extraction and Gene Analysis," Biomed. Microdevices, 2010, v. 12, pp. 1043-1049.
Sollier, et al. "Size-Selective Collection of Circulating Tumor Cells Using Vortex Technology," Lab Chip, 2014, v. 14, pp. 63-77.
Seo, et al. "Membrane-free Microfiltration by Asymmetric Inertial Migration," Appl. Phys. Lett., 2007, v. 91, pp. 033901-1-033901-3.
Hou, et al. "Isolation and Retrieval of Circulating Tumor Cells Using Centrifugal Forces," Sci. Rep. 2013, v. 3, pp. 1259-1267.
Alves, et al. "Isolation of Antibiotics from Industrial Fermentation Broths Using Membrane Technology," Desalination, 2002, v. 148, pp. 181-186.
Yang, et al. "A Microfluidic Device for Continuous, Real Time Blood Plasma Separation," Lab Chip, 2006, v. 6, 871-880.
Di Carlo, "Inertial Microfluidics," Lab Chip, 2009, v. 9, pp. 3038-3046.
Doyeux, et al. "Spheres in the Vicinity of a Bifurcation: Elucidating the Zweifach-Fung Effect," J. Fluid Mech., 2011, v. 674, pp. 359-388.
Inglis, et al. "Critical Particle Size for Fractionation by Deterministic Lateral Displacement," Lab Chip, 2006, v. 6, pp. 655-658.
Singh, et al. Fabrication and Characterization of HAR Microfluidic Device to Concentrate Microalgae. In Nanotechnology 2012: Electronics, Devices, Fabrication, MEMS, Fluidics, and Computational (vol. 2); Chapter 3: MEMS and NEMS Devices and Applications; 2012, pp. 157-160.
Pamme, N., "Continuous Flow Separations in Microfluidic Devices," Lab Chip, 2007, v. 7, No. 12, p. 1644-1659.
International Search Report dated May 20, 2015 for related application PCT/US2015/012107 filed Jan. 20, 2015.
Written Opinion dated May 20, 2015 for related application PCT/US2015/012107 filed Jan. 20, 2015.
International Search Report dated May 29, 2015 for related application PCT/US2015/012108 filed Jan. 20, 2015.
Written Opinion dated May 29, 2015 for related application PCT/US2015/012108 filed Jan. 20, 2015.

* cited by examiner

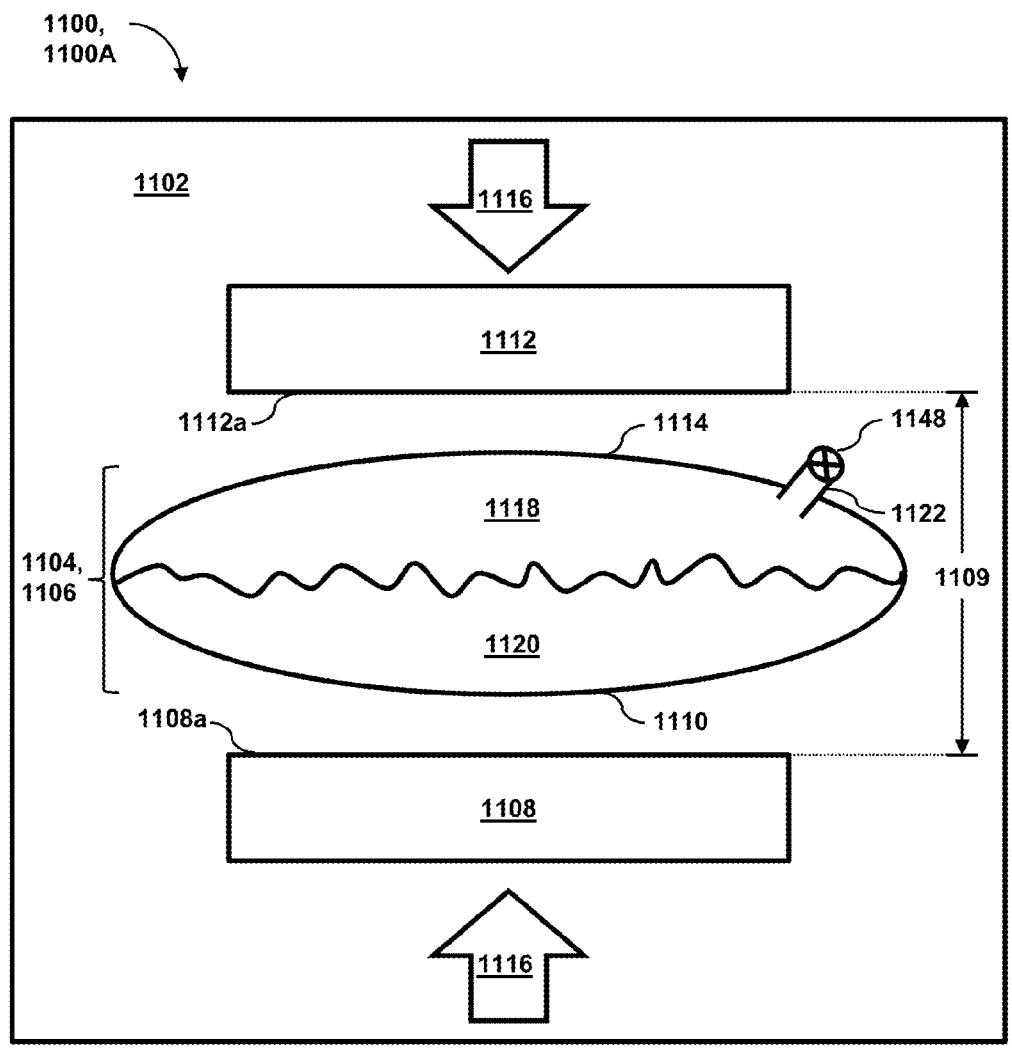
FIG. 1-A

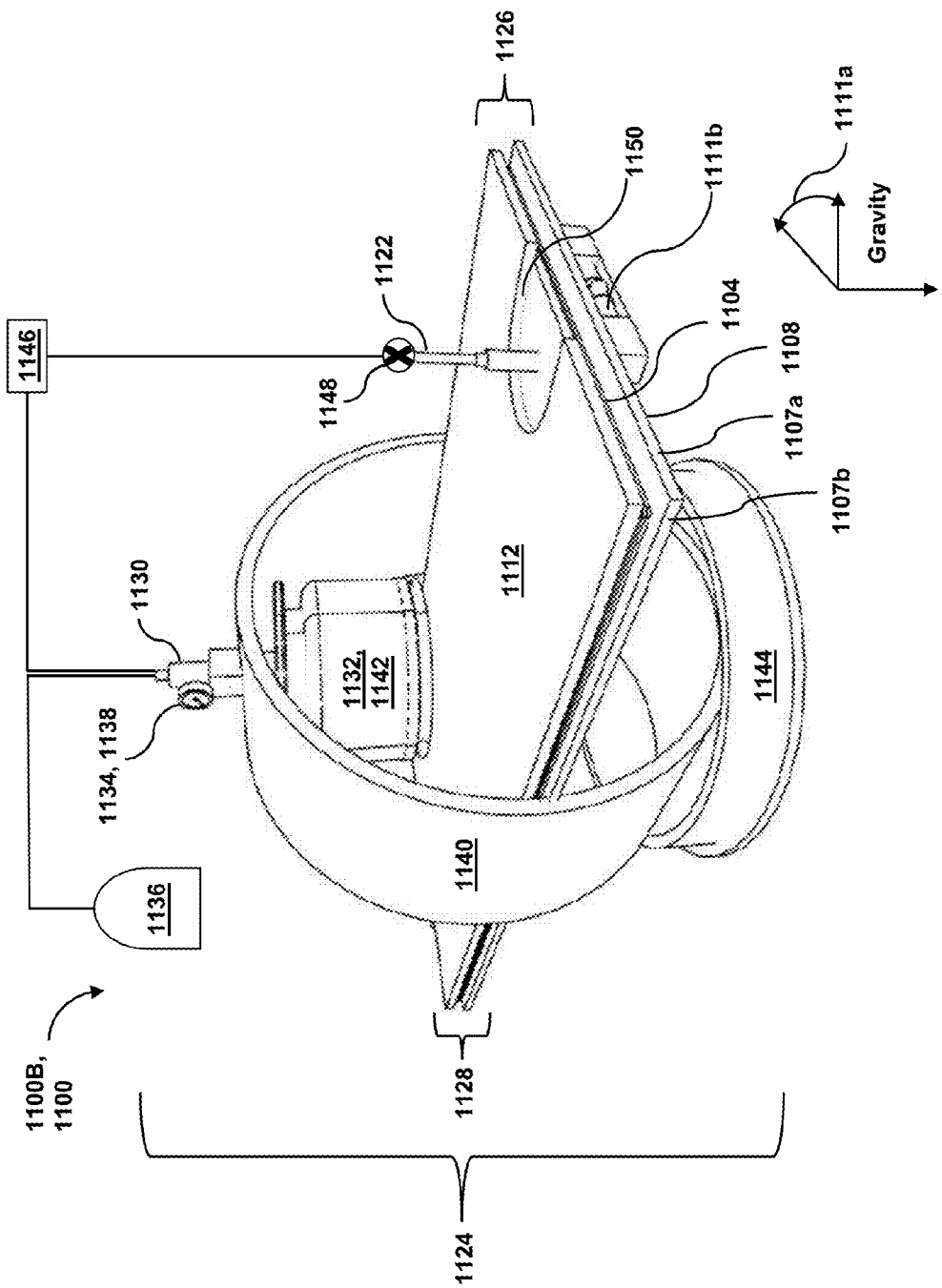
FIG. 1-B

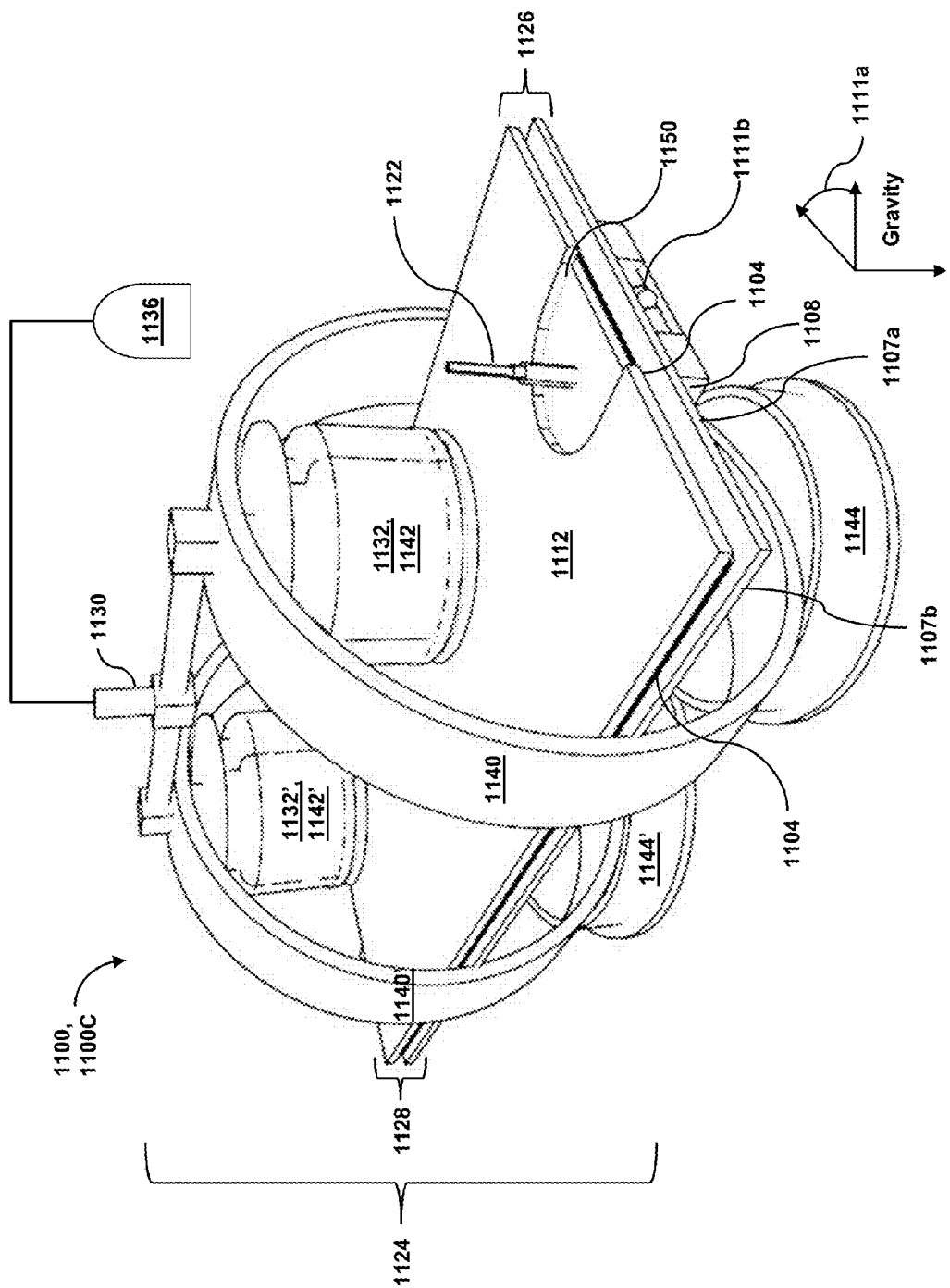
FIG. 1-C

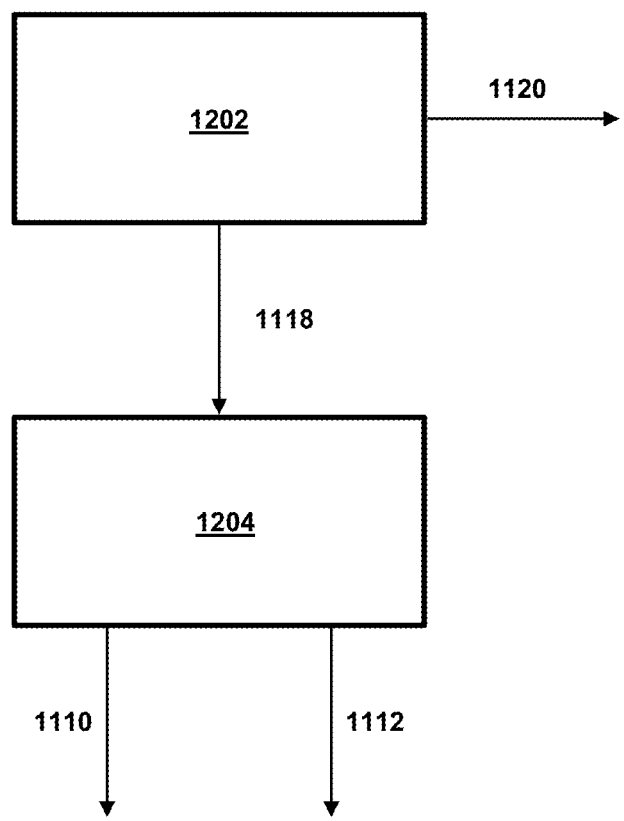
FIG. 1-D

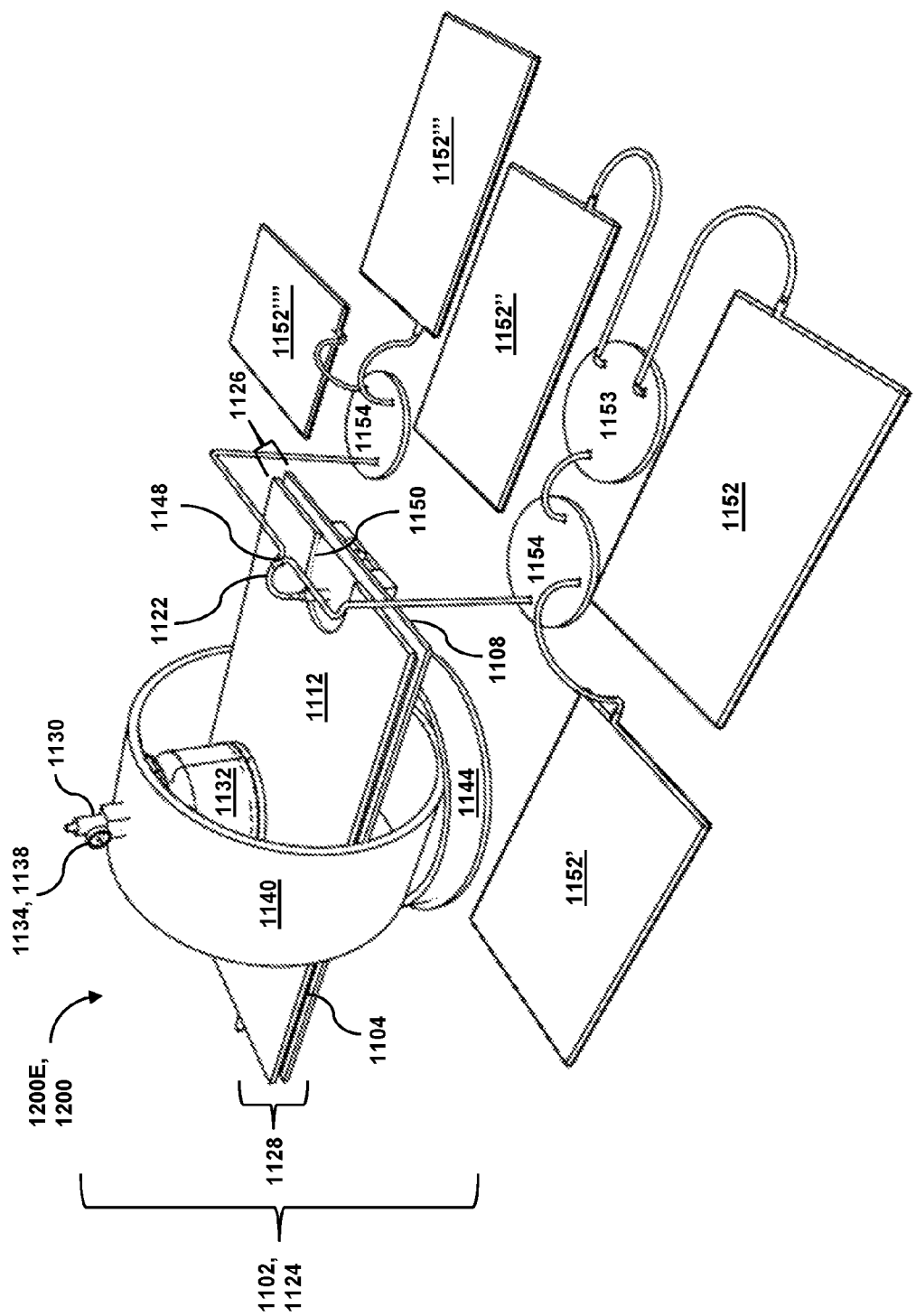
FIG. 1-E

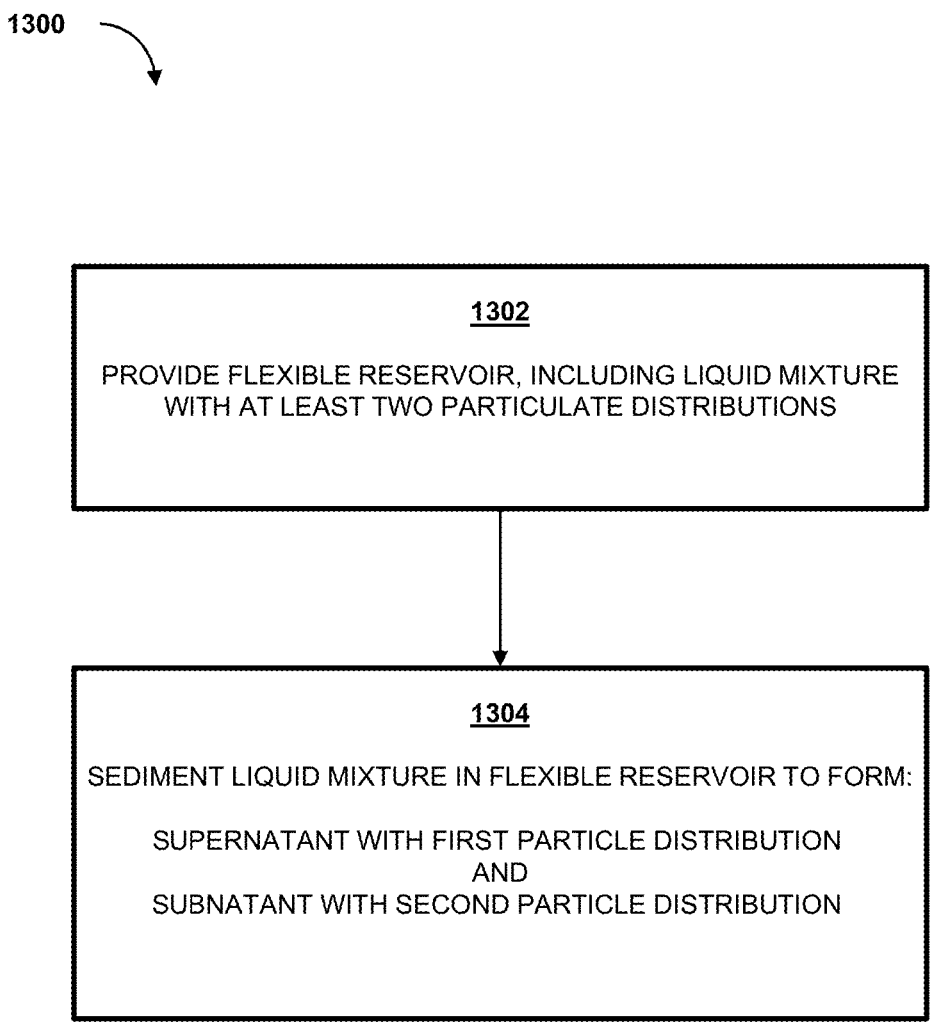
FIG. 1-F

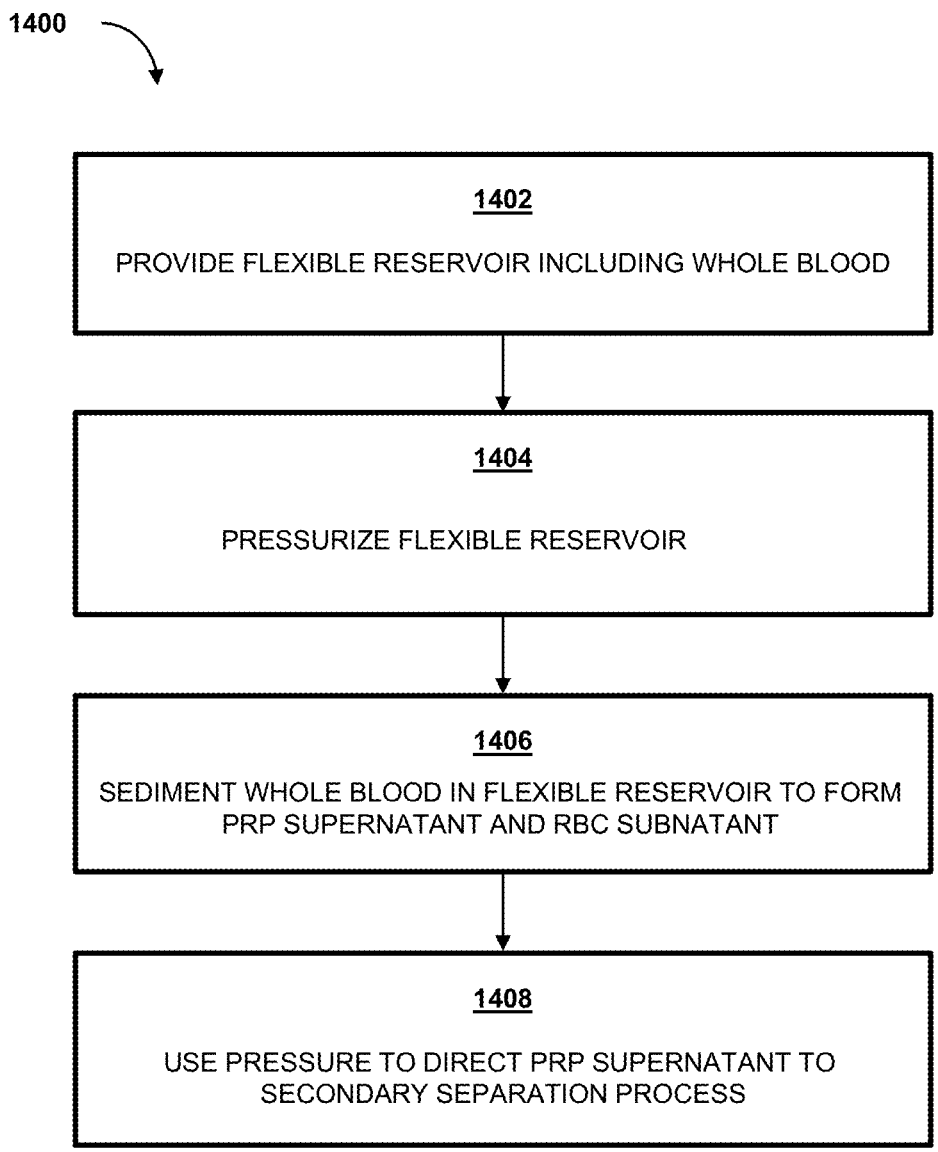
FIG. 1-G

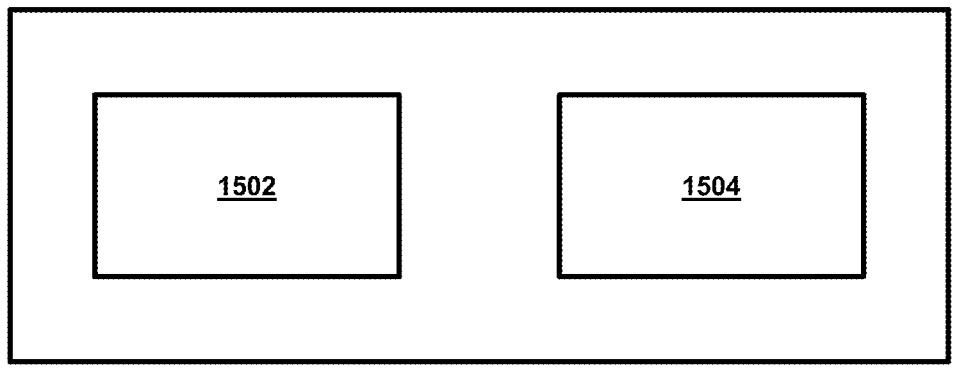
FIG. 1-H
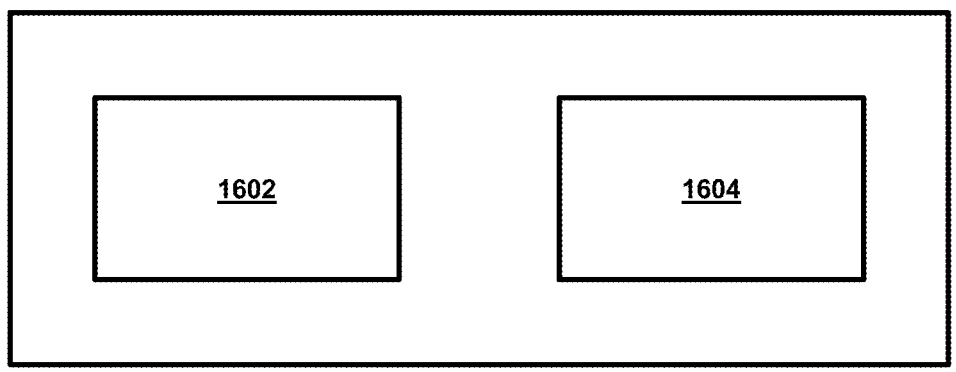
FIG. 1-I

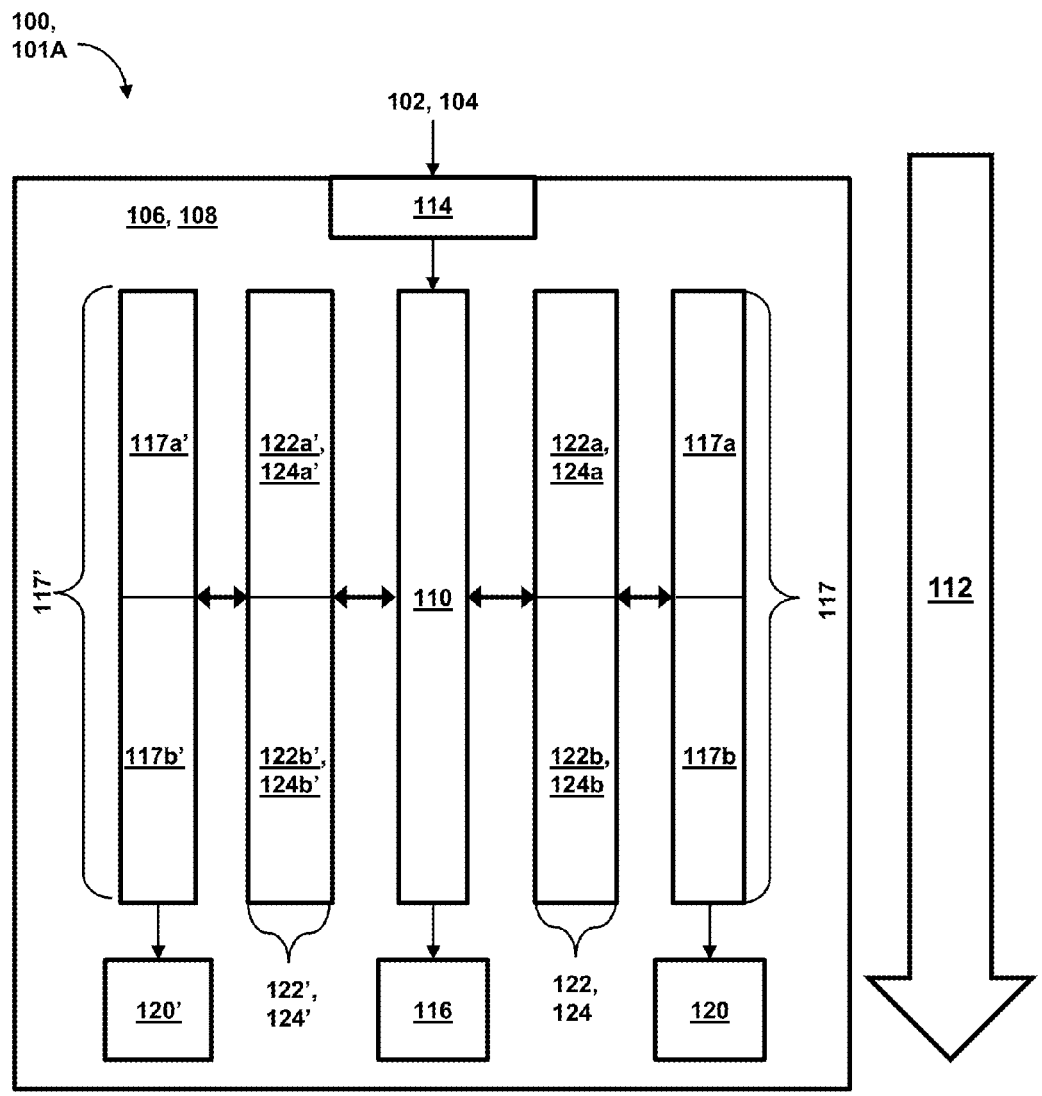
FIG. 1-J

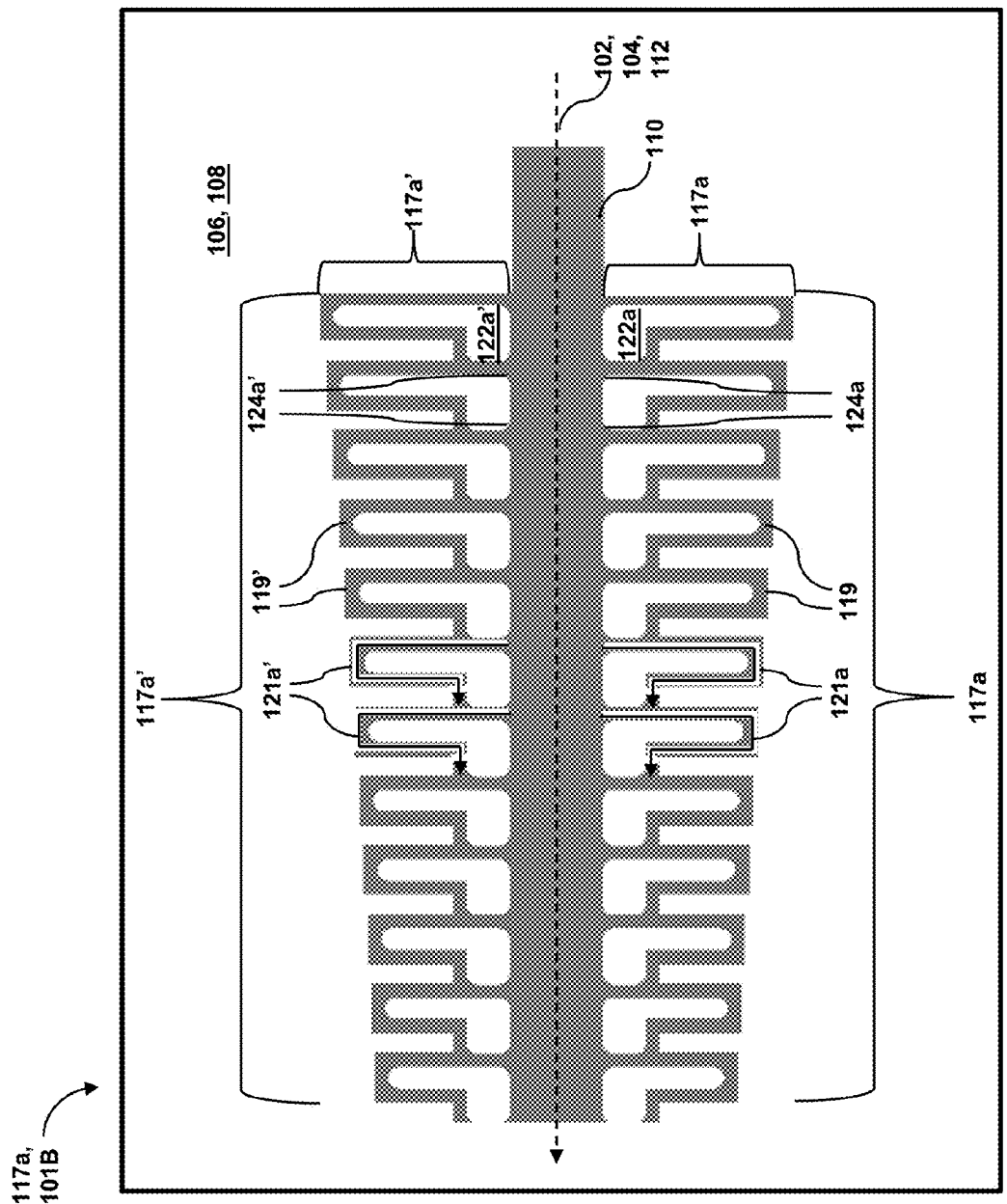
FIG. 1-K

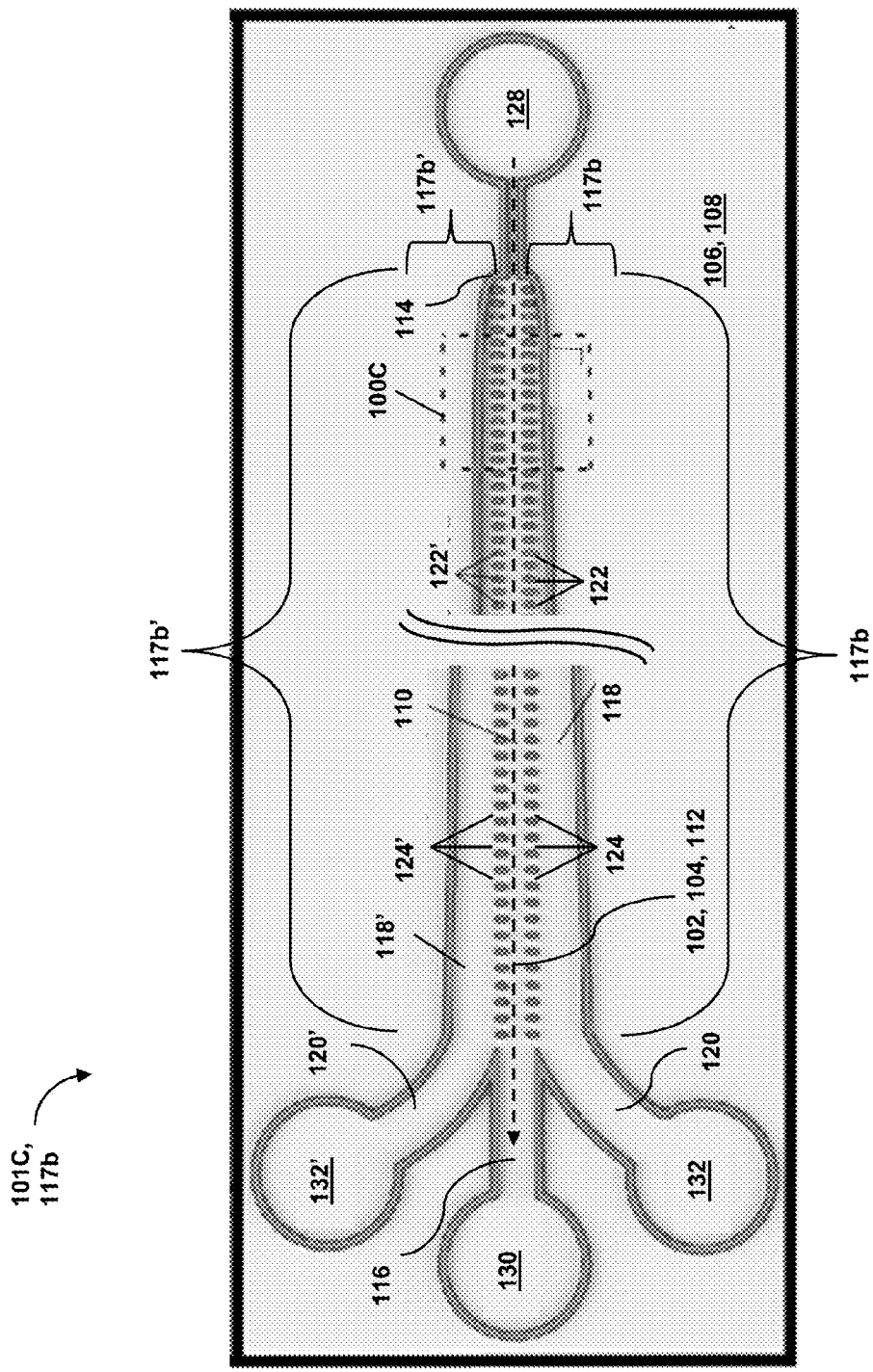
FIG. 1-L

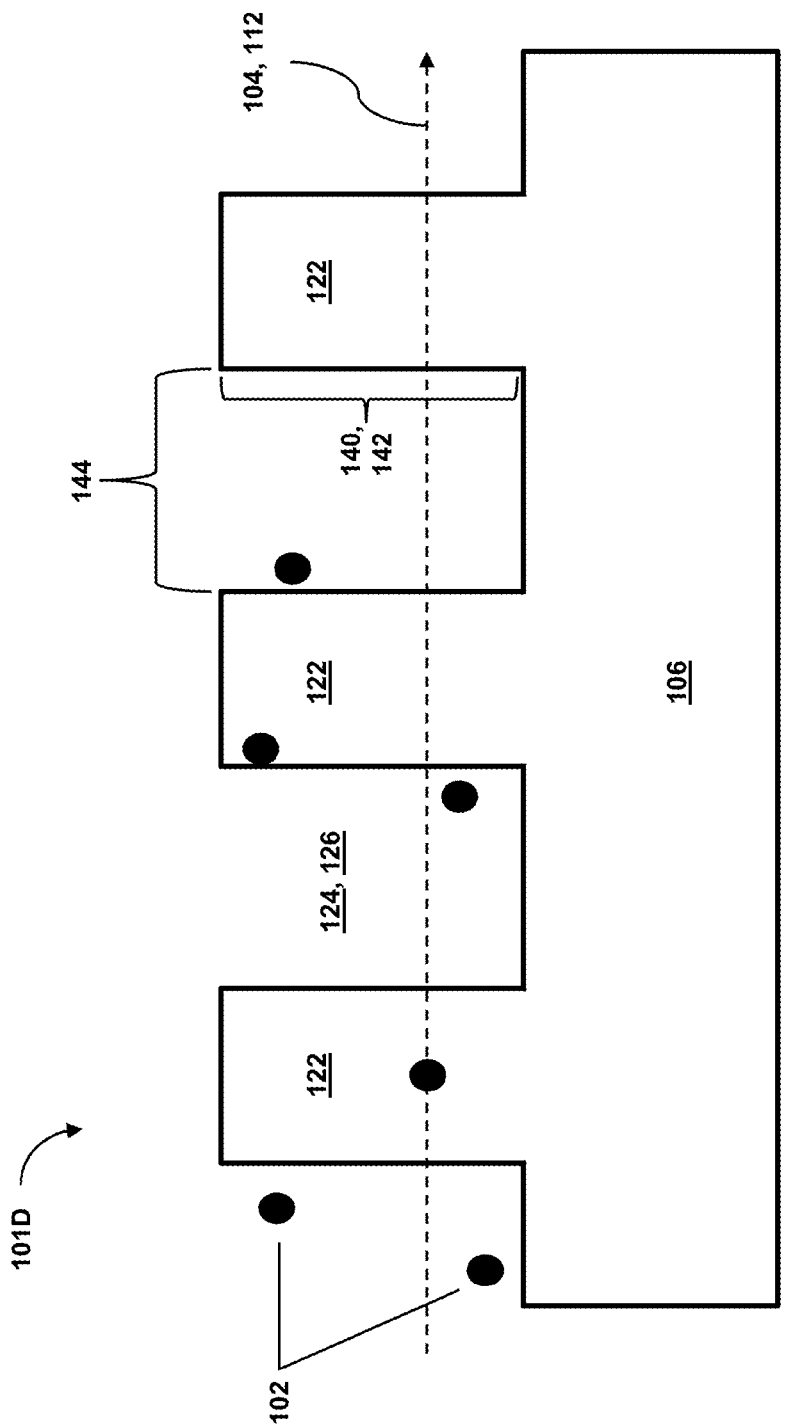
FIG. 1-M

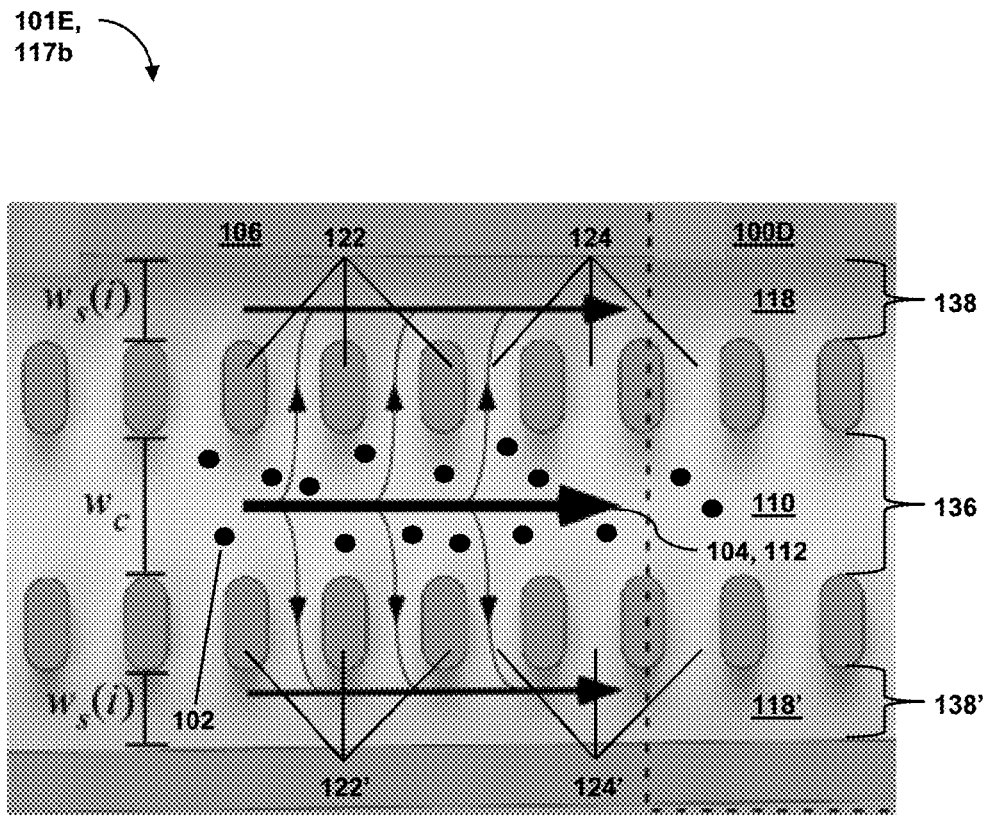
FIG. 1-N

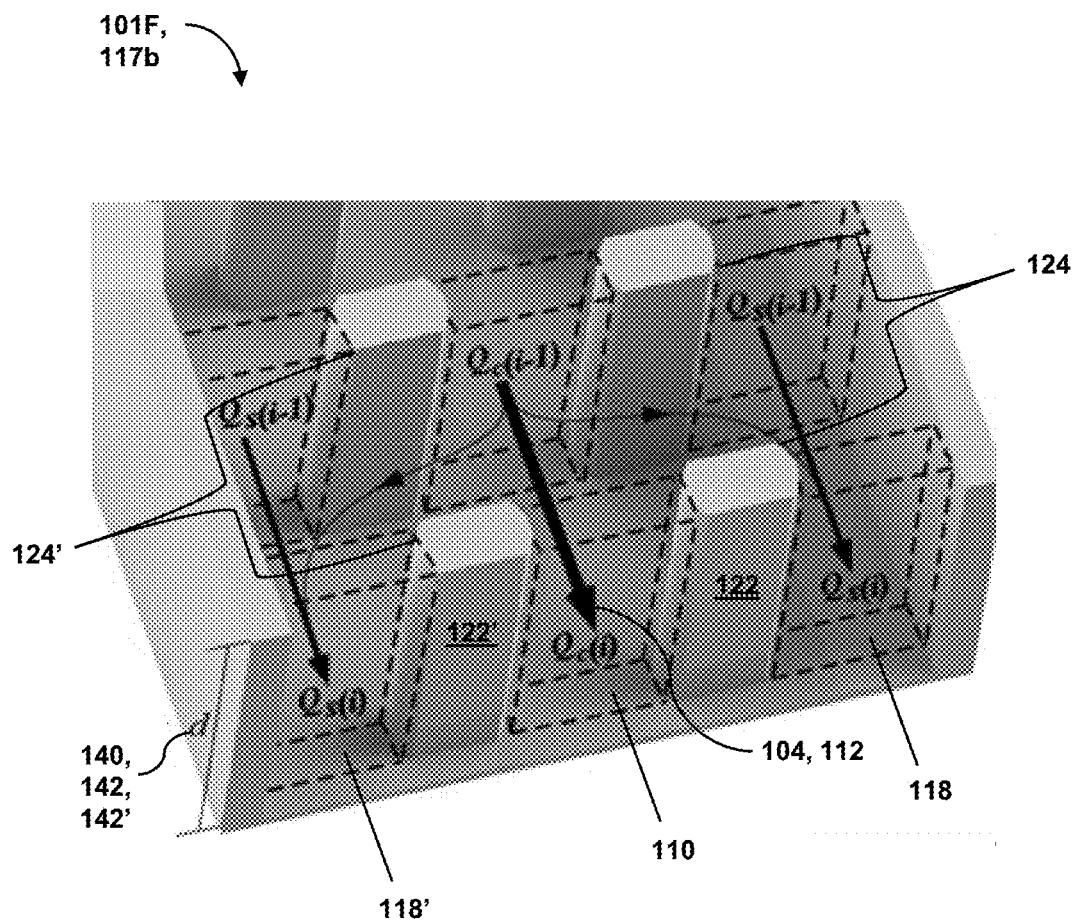
FIG. 1-O

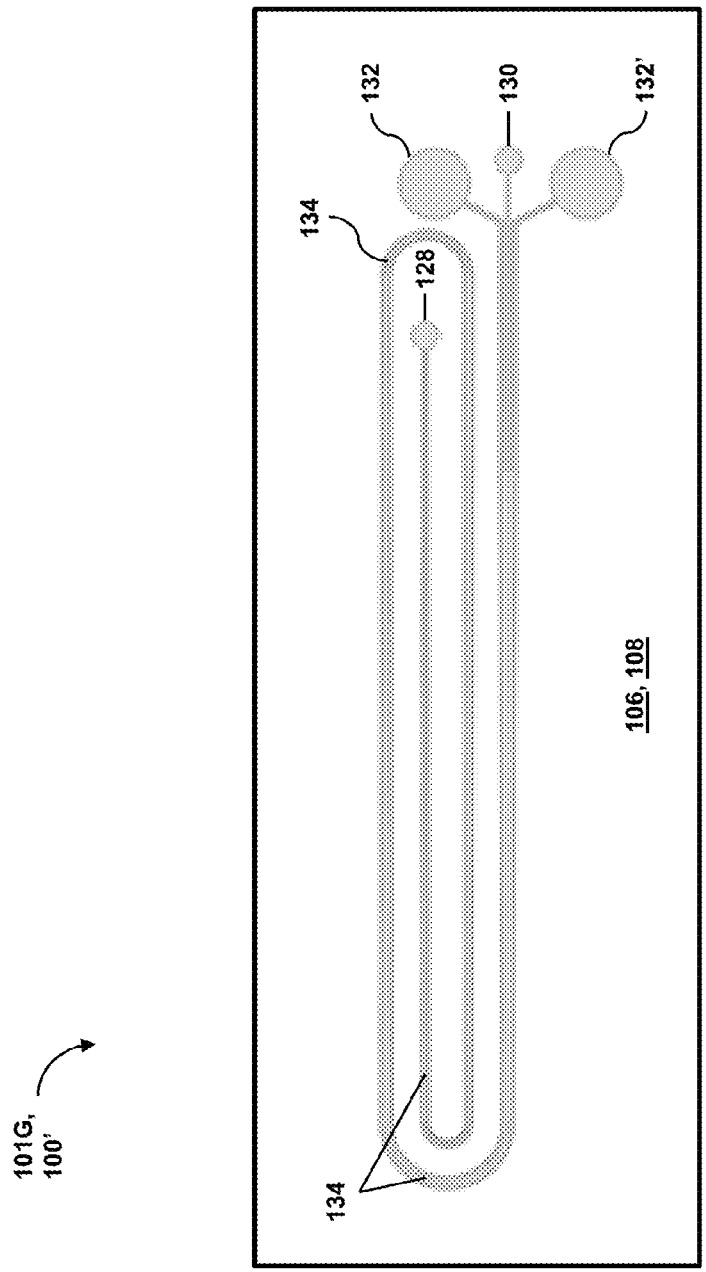
FIG. 1-P

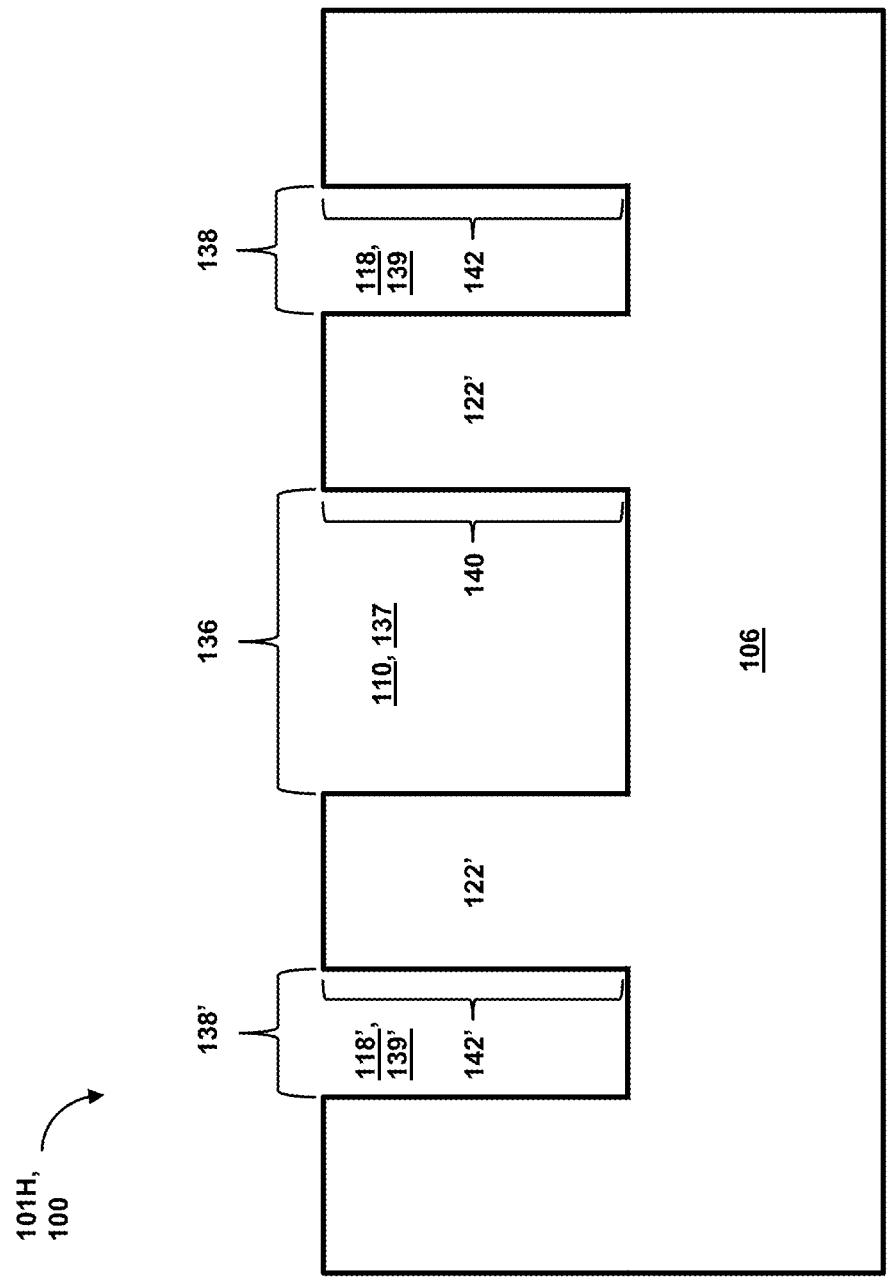
FIG. 1-Q

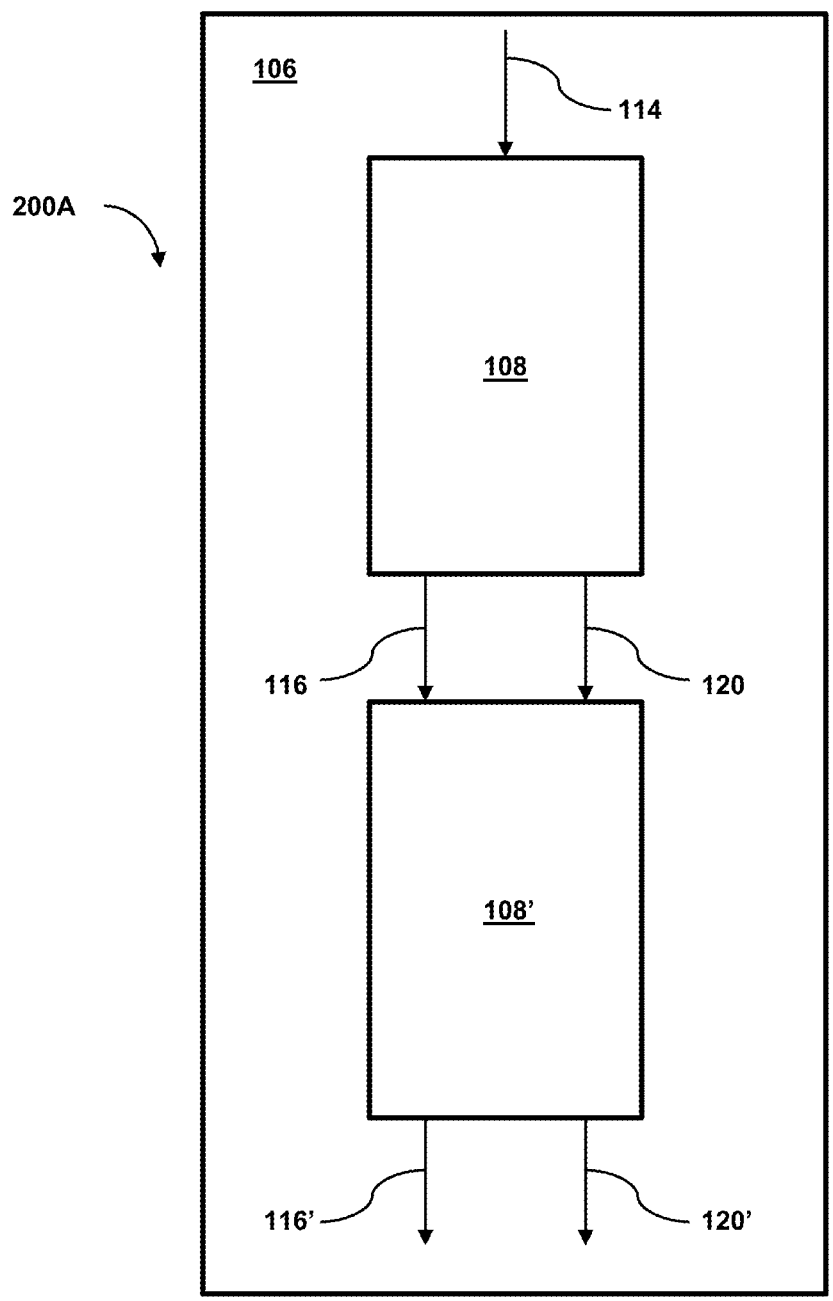
FIG. 2-A

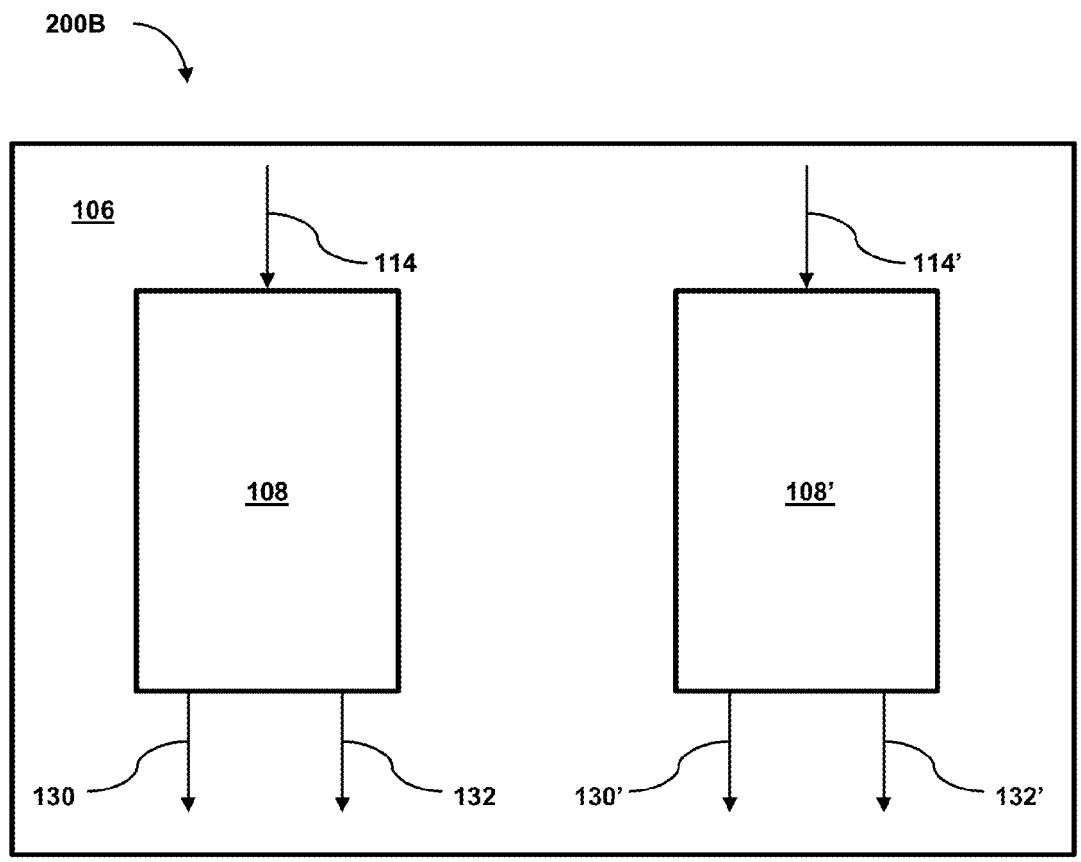
FIG. 2-B

500

502
PREPARE A CIF DEVICE DESIGN

↓

504
SELECT DESIRED GAP FLOW FRACTION $f_{gap}$ FOR CIF DEVICE

↓

506
DETERMINE A PLURALITY OF ADJUSTED DIMENSIONS ALONG THE FLOW PATH

↓

508
ADAPT CIF DEVICE DESIGN TO INCORPORATE PLURALITY OF ADJUSTED DIMENSIONS EFFECTIVE TO PROVIDE DECREASING FLOW RESISTANCE ALONG AT LEAST A PORTION OF THE FLOW PATH EFFECTIVE TO MODULATE THE CONCENTRATION OF PARTICLES OF THE DESIRED SIZE IN THE FLUID

FIG. 5

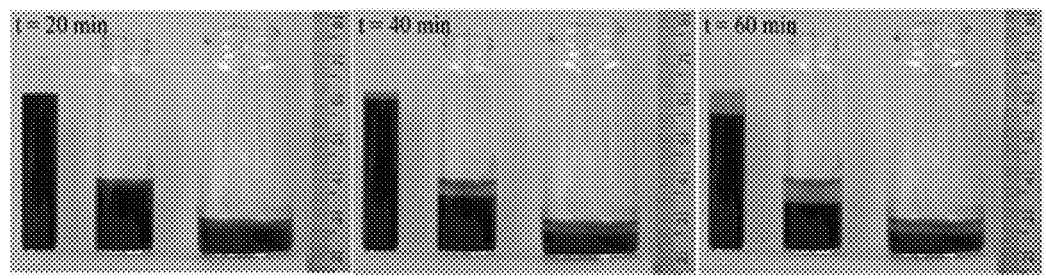
FIG. 7-A
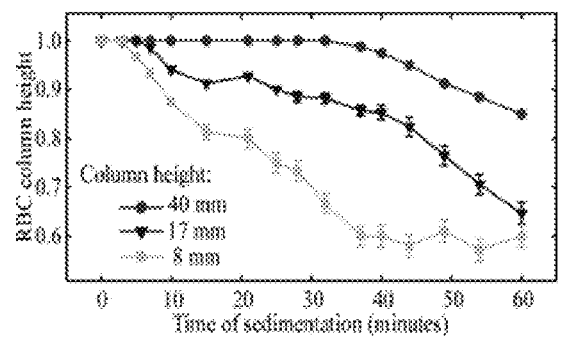
FIG. 7-B

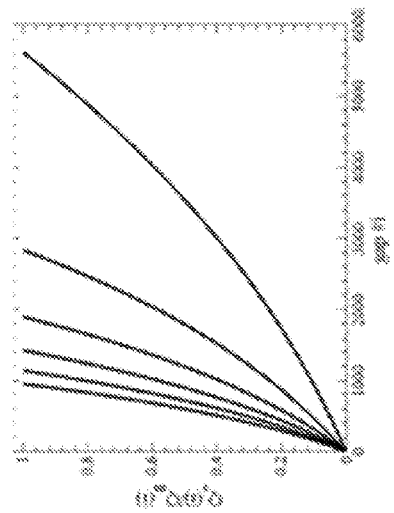
FIG. 10-A
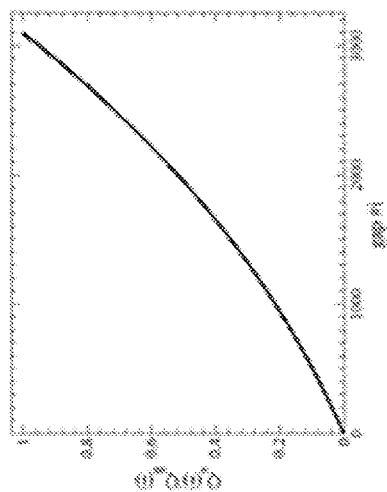
FIG. 10-B
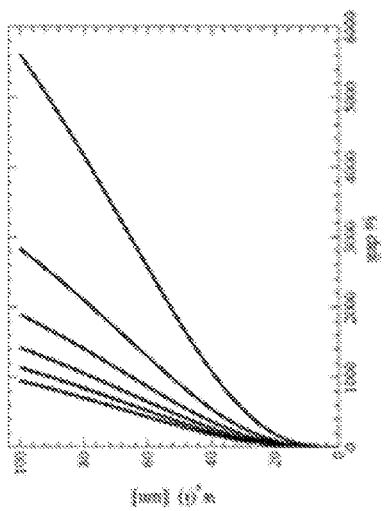
FIG. 10-C
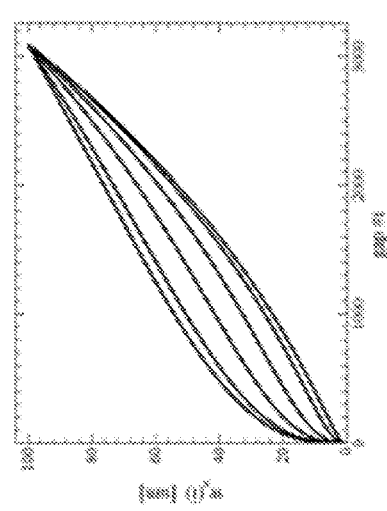
FIG. 10-D

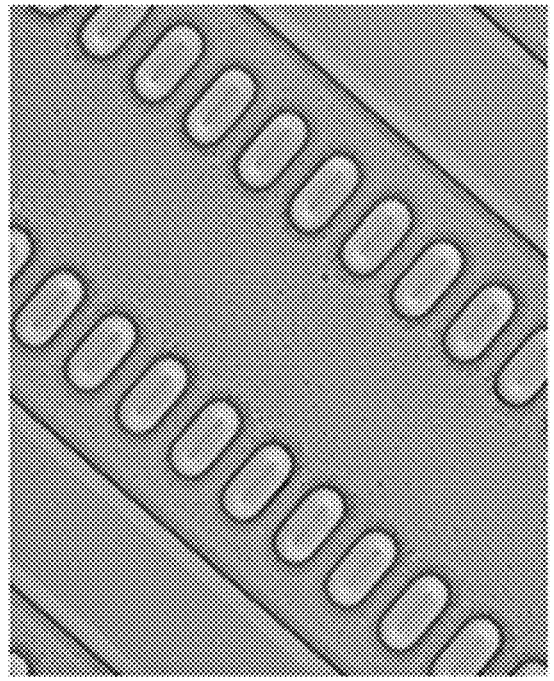
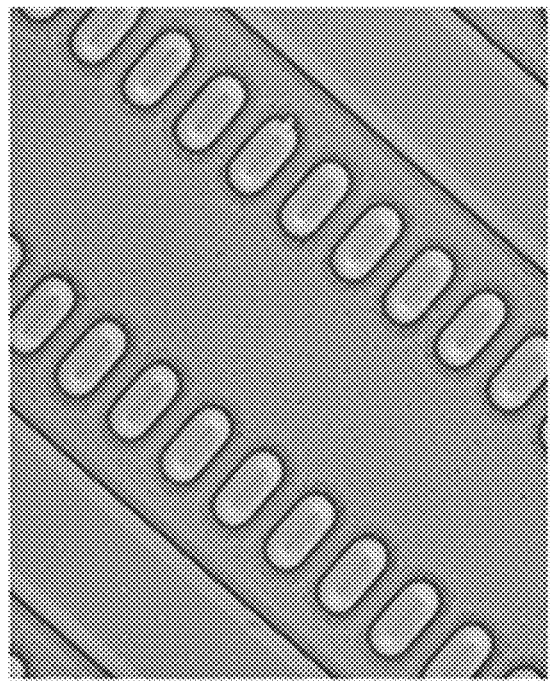
FIG. 12-A

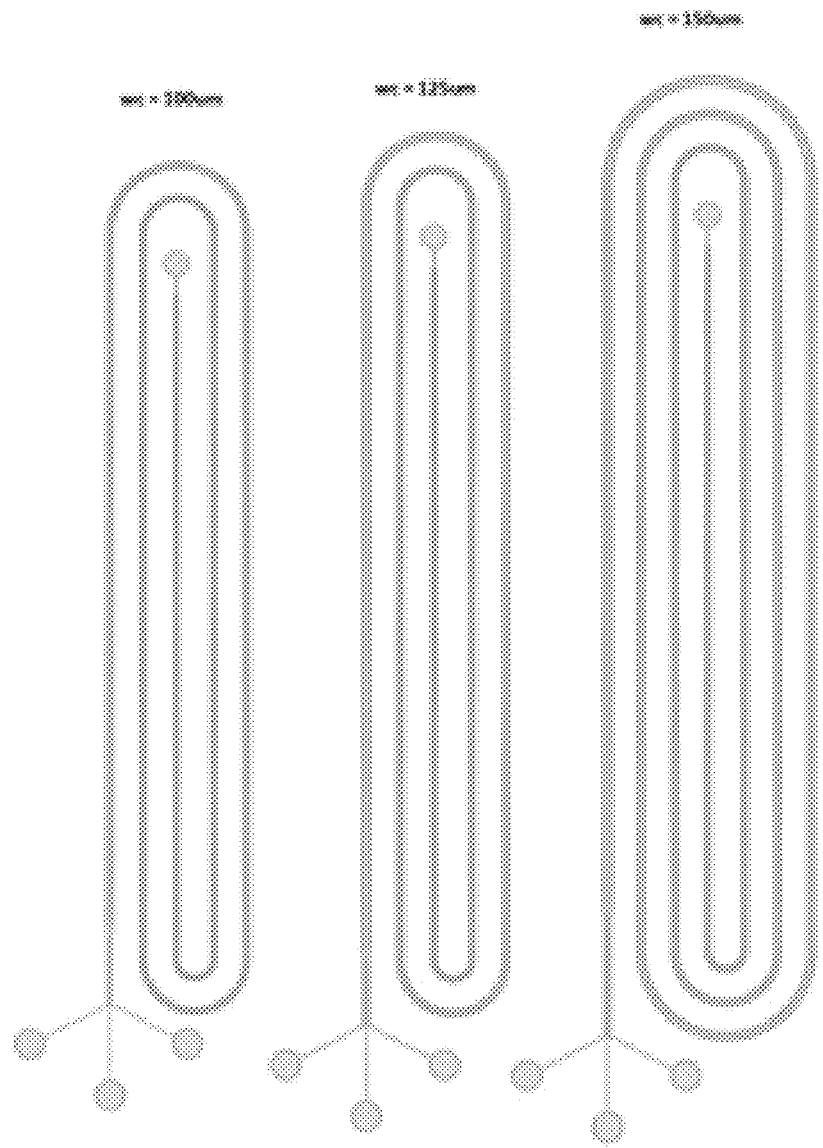
FIG. 12-B

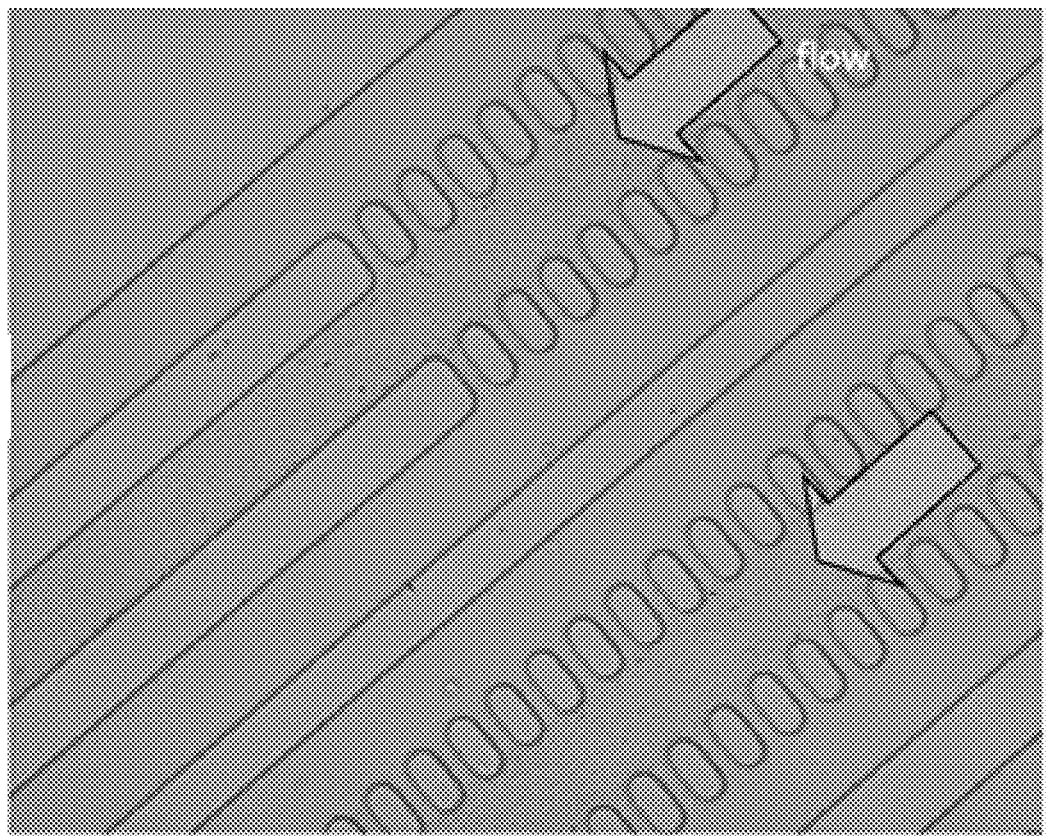
FIG. 12-C

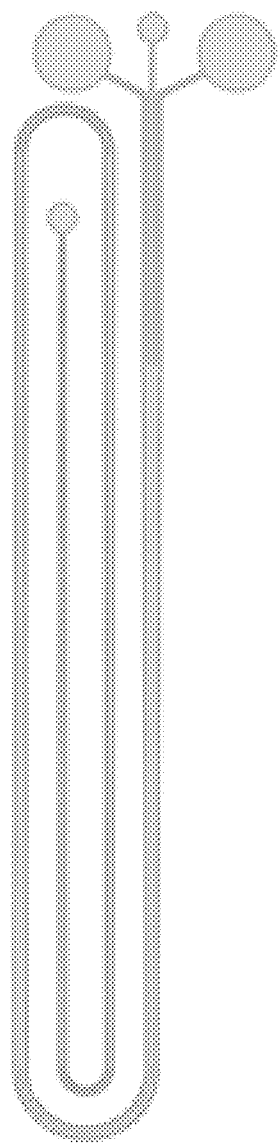
FIG. 13-A

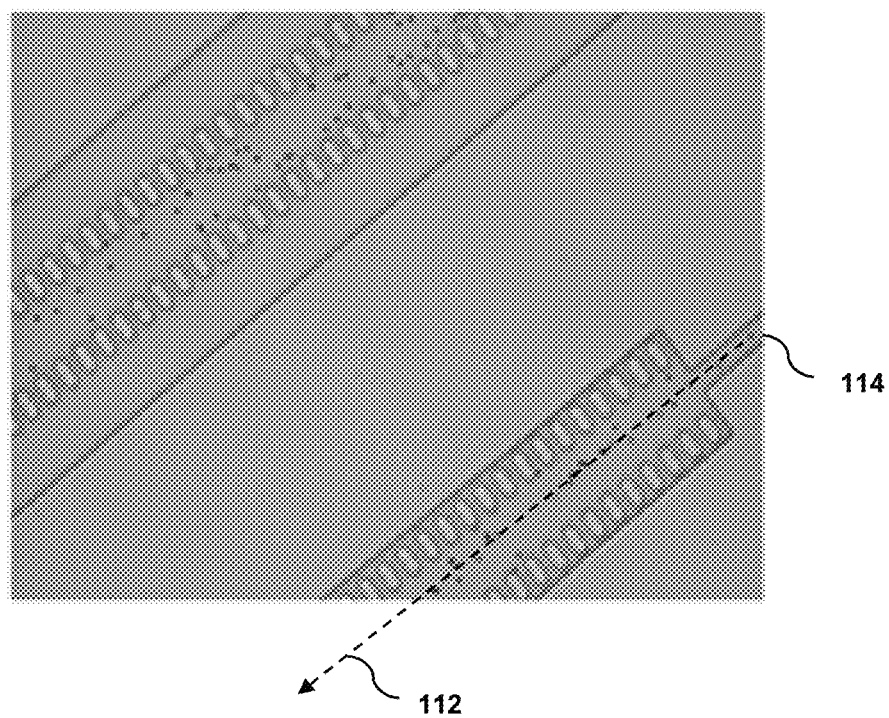
FIG. 13-B

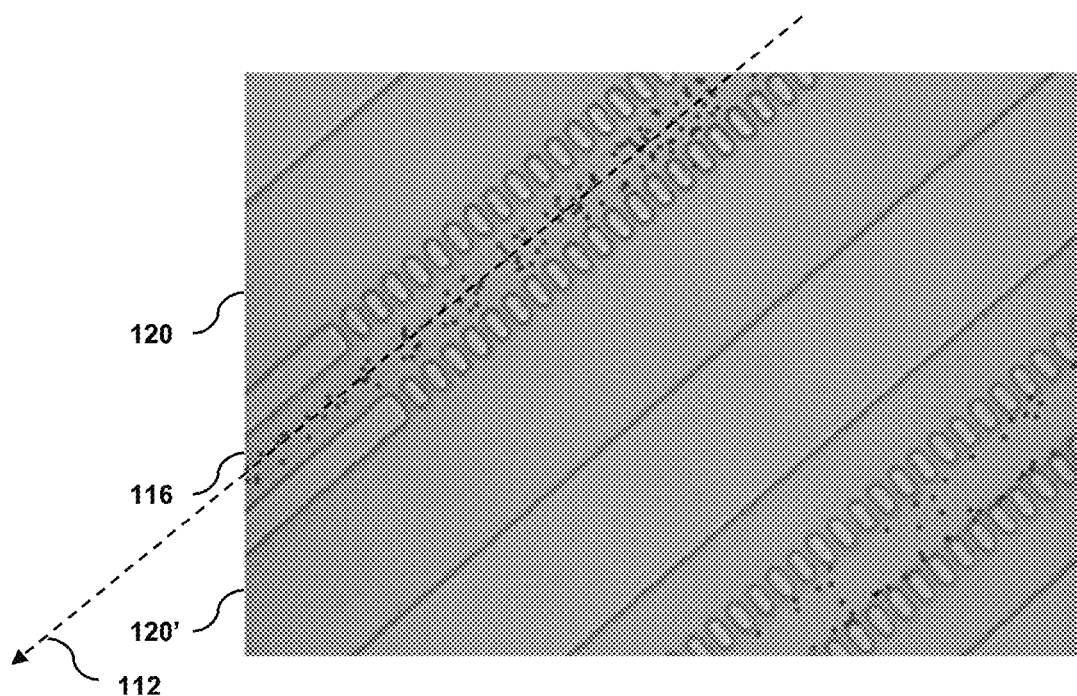
FIG. 13-C

100 million

PASSIVE SEPARATION OF WHOLE BLOOD

CROSS-REFERENCE TO RELATED APPLICATIONS

This application claims priority to U.S. Provisional Patent Application No. 61/929,357, filed on Jan. 20, 2014, which is incorporated by reference herein in its entirety.

STATEMENT REGARDING FEDERALLY SPONSORED RESEARCH

This invention was made with United States government support under federal STTR contract no. W81XWH-11-C-0008 awarded by the Department of Defense. The United States government may have certain rights in this invention.

BACKGROUND

Over 30 million individual units of the three main blood components—red blood cells (RBCs), platelet concentrate (PC), and plasma—are transfused in the U.S. every year. Nearly 70% of all whole blood (WB) donated in the U.S. is collected on mobile blood drives, often more than 100 miles away from the centralized blood banking facilities. Because of the significant differences in optimal storage conditions (1-6° C. for RBCs, 22±2° C. for platelets, −18° C. for plasma), WB should be quickly separated. The centrifugation-based equipment currently used to process WB into blood components may be undesirably expensive, bulky, laborious, and energy-intensive, especially for mobile blood collection coaches.

Further, high-speed centrifugation for WB separation may subject blood cells to damaging physical forces, may require two stages of centrifugation to separate WB into packed RBCs and platelet-rich plasma (PRP), followed by PRP into PC and platelet-poor plasma (PPP).

The present application appreciates that separation of whole blood may be a challenging endeavor.

SUMMARY

In one embodiment, a compression sedimentation system is provided. The compression sedimentation system may include a compression stage configured to accept a flexible reservoir. The flexible reservoir may be configured to contain a liquid mixture. The compression stage may include a base substrate including a first base face configured to contact a first face of the flexible reservoir. The compression stage may include a compression substrate including a first compression face configured to contact a second face of the flexible reservoir. The base substrate and the compression substrate together may be configured to apply a force to the flexible reservoir effective to create a pressure in the liquid mixture.

In another embodiment, an apparatus is provided. The apparatus may be configured to separate whole blood (WB). The apparatus may include a sedimentation system configured to separate the WB into a supernatant including platelet rich plasma (PRP) and a subnatant including red blood cells (RBC). The apparatus may include at least one platelet-concentrating device. The platelet-concentrating device may be operatively coupled to the sedimentation system to receive the supernatant including the PRP. The platelet-concentrating device may be configured to separate a platelet concentrate (PC) and a platelet poor plasma (PPP) from the supernatant including the PRP.

In one embodiment, a method for compression sedimentation is provided. The method may include providing a flexible reservoir including a liquid mixture. The liquid mixture may include two or more particulate distributions. The two or more particulate distributions may be characterized by different effective average particulate diameters. The two or more particulate distributions may be characterized by different particulate densities. The method may include sedimenting the liquid mixture in the flexible reservoir to form a supernatant and a subnatant. The supernatant may include at least a first particulate distribution. The first particulate distribution may be characterized by a first effective average particulate diameter. The first particulate distribution may be characterized by a first particulate density. The subnatant may include at least a second particulate distribution. The second particulate distribution may be characterized by a second effective average particulate diameter. The second particulate distribution may be characterized by a second particulate density.

In another embodiment, a method for separation of WB is provided. The method may include providing a flexible reservoir including the WB. The method may include sedimenting the WB in the flexible reservoir for a period of time to form a supernatant including a platelet rich plasma (PRP) and a subnatant including red blood cells (RBCs). The method may include pressurizing the flexible reservoir including one or more of the supernatant including the PRP and the subnatant including the RBCs to a pressure. The method may include using the pressure to direct one or more of the supernatant including the PRP and the subnatant including the RBCs to a secondary separation process.

In one embodiment, a kit for compression sedimentation is provided. The kit may include a compression sedimentation system. The compression sedimentation system may include a compression stage configured to accept a flexible reservoir. The flexible reservoir may be configured to contain a liquid mixture. The compression stage may include a base substrate configured to contact a first face of the flexible reservoir. The compression stage may include a compression substrate configured to contact a second face of the flexible reservoir. The kit may include instructions. The instructions may include directing a user to compress the base substrate and the compression substrate together to apply a force to the flexible reservoir effective to create a pressure in the liquid mixture.

In another embodiment, a kit for separating WB is provided. The kit may include an apparatus configured to separate WB. The apparatus may include a sedimentation system configured to separate the WB into a supernatant including platelet rich plasma (PRP) and a subnatant including red blood cells (RBC). The apparatus may include at least one platelet-concentrating device operatively coupled to the sedimentation system to receive the supernatant including the PRP. The platelet concentrating device may be configured to separate a platelet concentrate (PC) and a platelet poor plasma (PPP) from the supernatant including the PRP. The kit may include instructions. The instructions may direct a user to position a flexible reservoir including the WB in the sedimentation system. The instructions may direct a user to pressurize the flexible reservoir including the WB to a pressure. The instructions may direct the user to sediment the WB in the flexible reservoir to form a supernatant including a platelet rich plasma (PRP) and a subnatant including red blood cells (RBC). The instructions may direct the user to use the pressure to direct the supernatant including the PRP to the at least one platelet-concentrating device to separate a platelet concentrate (PC) and a platelet poor plasma (PPP) from the supernatant.

BRIEF DESCRIPTION OF THE DRAWINGS

The accompanying figures, which are incorporated in and constitute a part of the specification, illustrate example methods and apparatuses, and are used merely to illustrate example embodiments.

FIGS. 1-A, 1-B, 1-C, 1-D, 1-E, 1-F, 1-G, 1-H, and 1-I depict aspects of exemplary systems and methods using sedimentation.

FIG. 1-A is a block diagram depicting aspects of an exemplary compression sedimentation system.

FIG. 1-B is a perspective view depicting further aspects of an exemplary compression sedimentation system.

FIG. 1-C is a perspective view depicting further aspects of an exemplary compression sedimentation system.

FIG. 1-D is a block diagram depicting aspects of an exemplary apparatus for separating WB.

FIG. 1-E is a perspective view depicting further aspects of an exemplary apparatus for separating WB, leukoreduction, and the like.

FIG. 1-F is a flow diagram depicting an exemplary method for compression sedimentation.

FIG. 1-G is a flow diagram depicting an exemplary method for separating WB.

FIG. 1-H is a block diagram depicting a kit for compression sedimentation.

FIG. 1-I is a block diagram depicting a kit for separating WB.

FIGS. 1-J, 1-K, 1-L, 1-M, 1-N, 1-O, 1-P, and 1-Q depict various views of an exemplary CIF device.

FIG. 1-J is a top view illustrating an exemplary CIF device.

FIG. 1-K is a diagram illustrating a first side channel network portion of an exemplary CIF device.

FIG. 1-L is a diagram illustrating a second side channel network portion of an exemplary CIF device.

FIG. 1-M is a close-up top view along a flow path of an exemplary CIF device.

FIG. 1-N is a close-up top view along a flow path of an exemplary CIF device.

FIG. 1-O is a close-up perspective view of an exemplary CIF device.

FIG. 1-P is a top view along a flow path of an exemplary CIF device.

FIG. 1-Q is a cross section view perpendicular to a flow path of an exemplary CIF device.

FIG. 2-A is a block diagram of a CIF device including two CIF modules fluidically coupled in series.

FIG. 2-B is a block diagram of a CIF device including two CIF modules fluidically coupled in parallel.

FIG. 5 is a flow diagram depicting an exemplary method for designing a CIF device.

FIG. 7A depicts sedimentation of WB according to aspect ratio of various vessels for equivalent volumes of WB (3 mL).

FIG. 7B is a graph showing the dependence of sedimentation speed on aspect ratio of the vessel for equivalent volumes of WB (3 mL).

FIGS. 10-A, 10-B, 10-C, and 10-D are a series of graphs illustrating the dependence of device length and side channel width on input parameters such as desired device depth d and degree of flow fraction $f_{gap}$.

FIG. 10-A is a graph demonstrating an inverse correlation between the total number of gaps for achieving a given total degree of particle filtration/enrichment and the value of $f_{gap}$, which decreases linearly from $5.76 \times 10^{-3}$ to $9.6 \times 10^{-5}$ in the curves from left-to-right.

FIG. 10-B is a graph demonstrating that side channel width $w_s(i)$ may increase at each subsequent gap while the ratio of side channel flow to central channel flow may increase toward a unit endpoint condition, for the same values of $f_{gap}$ as in FIG. 10-A.

FIG. 10-C is a graph demonstrating a depth-dependence of the $w_s(i)$ curve for a variety of depths (left-to-right: 150 µm, 100 µm, 50 µm, 25 µm, 10 µm, 5 µm), while $f_{gap}$ is held constant at $1.76 \times 10^{-4}$.

FIG. 10-D is a graph demonstrating that when $f_{gap}$, is constant, the six cases in FIG. 10-C generate the same relative flow fraction curve, independent of device depth.

FIGS. 12-A, 12-B, and 12-C demonstrate a two-step process for the efficient creation of a platelet enrichment device.

FIG. 12-A is a micrograph showing the transition between platelet retention in the central channel (left panel) and platelet loss (right panel) in a parallel array of test device segments with a range of flow fraction $f_{gap}$ values, and a given value of $w_c$.

FIG. 12-B is schematic showing that long-length devices with the given parameters are easily patterned for photomask creation.

FIG. 12-C is a micrograph image of the output of a representative device during operation showing that greater than 85% of platelets may be retained in the central channel, representing approximately three times enrichment in particle concentration.

FIGS. 13-A, 13-B, and 13-C illustrate a CIF device. A value for $f_{gap}$ was selected corresponding to retaining particle diameters between 5.9 µm to 8.3 µm and was used to pattern a full-length device with a total filtration fraction of approximately 90%.

FIG. 13-A is a schematic illustrating a CIF device with end side channel widths much larger than that of the central channel.

FIG. 13-B is an image of the input of the CIF device showing the 1.5-4 µm platelets and 8.3 µm particles in the central channel.

FIG. 13-C is an image of the output of the CIF device showing selective retention and concentration of the large 8.3 µm diameter particles compared to the platelets.

DETAILED DESCRIPTION

Figure 3:
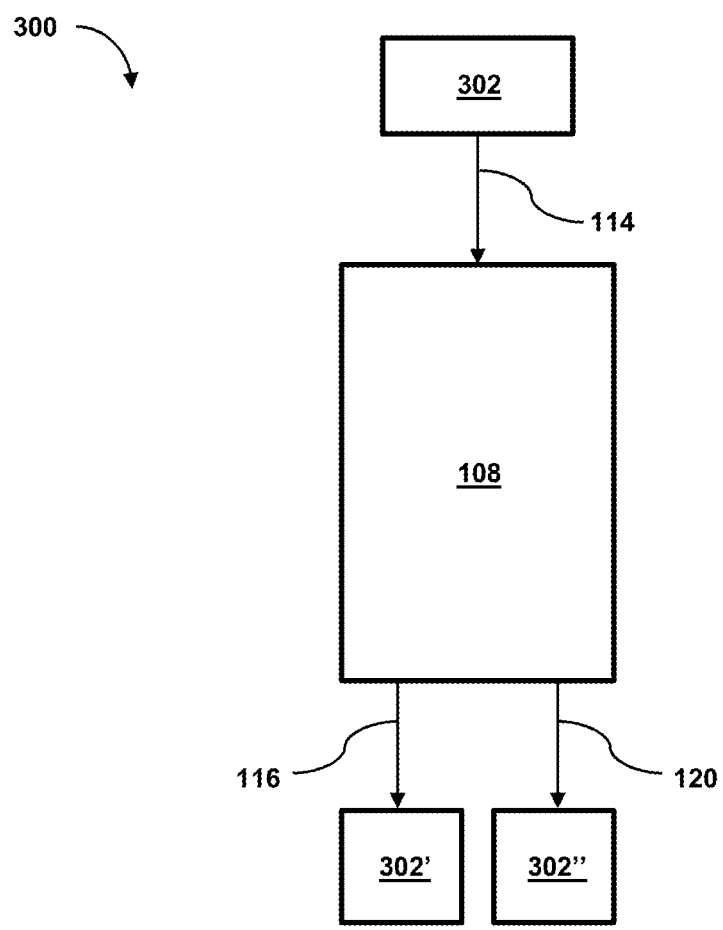
FIG. 3 is a block diagram of a CIF device including at least one additional separation device.

FIG. 1-A is a block diagram 1100A depicting aspects of an exemplary compression system 1100. In various embodiments, compression sedimentation system 1100 may include a compression stage 1102 configured to accept a flexible reservoir 1104, e.g., a blood bag. Flexible reservoir 1104 may be configured to contain a liquid mixture 1106, e.g., whole blood (WB). Compression stage 1102 may include a base substrate 1108 including a first base face 1108a configured to contact a first face 1110 of flexible reservoir 1104. Compression stage 1102 may include a compression substrate 1112 including a first compression face 1112a configured to contact a second face 1114 of flexible reservoir 1104. Base substrate 1108 and compression substrate 1112 together may be configured to apply a force 1116 to flexible reservoir 1104 effective to create a pressure in liquid mixture 1106.

In some embodiments, compression system 1100 may be configured effective to provide for sedimentation of the liquid mixture 1106 in the flexible reservoir 1104 into a supernatant 1118 and a subnatant 1120 including a sediment. Providing sedimentation may include allowing sedimentation in the case of passive sedimentation, or facilitating sedimentation, in the case of applying pressure, and the like. For example, passive separation may be relatively rapid, proceeding to carry sedimentation to a desired state of completion over a period in hours of between about one or more of: 0.25 to 5, 0.5 to 4, 0.75 to 3, and 1 to 2. Passive separation may be relatively rapid. For example, in the case of passive sedimentation under gravity, and sedimentation height 1109 with respect to gravity in flexible reservoir 1104 of between about 5 to 15 millimeters, sedimentation of whole blood may occur in 1-3 h. Further, without wishing to be bound by theory, it is believed that individual RBCs may form 'coinstacks' or so-called rouleaux, which may increase effective diameter of the RBCs and thus RBC sedimentation speed.

For example, in various embodiments, base substrate 1108 and compression substrate 1112 may together be characterized by a separation 1109 between first base face 1108a and first compression face 112b. Base substrate 1108 and compression substrate 1112 may together be configured to apply force 1116 to flexible reservoir 1104 over separation 1109 effective to create the pressure in liquid mixture 1106. Separation 1109 may include a range in millimeters of about one or more of: 5 to 15, 5 to 14, 6 to 13, and 6 to 12.

The pressure in the liquid may be effective to direct the supernatant 1118 through an output 1122 of the flexible reservoir 1104, e.g., after sedimentation has proceeded to a desired extent of completion and/or a valve 1148 coupled to output 1122 is opened.

FIG. 1-B is a perspective view 1100B depicting further aspects of an exemplary compression system 1100. In several embodiments, compression stage 1102 may include a chassis 1124. Chassis 1124 may be configured to position the base substrate 1108 and the compression substrate 1112 together to compress the flexible reservoir 1104 between the base substrate 1108 and the compression substrate 1112. Flexible reservoir 1104 may include a first end 1126 proximal to the output 1122 of the flexible reservoir 1104 and a second end 1128 distal to the output 1122 of the flexible reservoir 1104. Chassis 1124 may be configured to place the base substrate 1108 and the compression substrate 1112 in closer proximity at the second end 1128 of the flexible reservoir 1104 compared to the first end 1126 of the flexible reservoir 1104. Chassis 1124 may include one or more gas pass-through conduits 1130 configured to direct a gas to a gas spring 1132. Gas pass-through conduits 1130 each may be operatively coupled to one or more of: a gas valve 1134, a gas pressure source 1136, and a pressure gauge 1138. Chassis 1124 may include one or more mounts 1140. Mounts 1140 may be configured to receive the base substrate 1108, the compression substrate 1112, and one or more force generators 1142 effective to permit compression of the flexible reservoir 1104 between the base substrate 1108 and the compression substrate 1112 according to a force 1116 applied by the one or more force generators 1142. Chassis 1124 may be formed of any suitable material, capable of supporting force 1116 applied by the one or more force generators 1142. For example, suitable materials may include one or more of: a metal, a ceramic, a glass, a polymer, or a fiber-reinforced composite. Mounts 1140 may include one or more ring mounts.

In several embodiments, chassis 1124 may include one or more bases 1144 corresponding to the one or more mounts 1140. Bases 1144 may be configured to receive the one or more mounts 1140 effective to position a lateral edge 1107b of base substrate 1108 in an orientation normal with respect to gravity. Bases 1144 may include one or more ring bases. Bases 1144 may be configured to receive one or more mounts 1140 effective to incline a tangential edge 1107a of base substrate 1108 in an orientation at an angle 1111a with respect to gravity. Angle 1111a may be adjusted such that first end 1126 is slightly elevated compared to second end 1128. Angle 1111a may be adjustable in a range of about 0 degrees to about 10 degrees. A level indicator 1111b may be operatively coupled to indicate an angle of one or more of: lateral edge 1107b of base substrate 1108 with respect to gravity and tangential edge 1107a of base substrate 1108 with respect to gravity. A second level indicator (not shown) may be operatively coupled to indicate angle 1111a of tangential edge 1107a of base substrate 1108 with respect to gravity.

In various embodiments, one or more force generators 1142 may be configured to control the force 1116 applied to liquid mixture 1106 contained in flexible reservoir 1104. For example, force generators 1142 may be configured to control the pressure generated within liquid mixture 1106 contained in the flexible reservoir 1104 within a range in PSI of one or more of about: 0.5 to 40, 0.5 to 20, and 1 to 20. A pressure gauge 1138 may be operatively coupled to indicate the pressure applied to flexible reservoir 1104 by one or more force generators 1142 or a corresponding pressure within one or more force generators 1142. For example, the one or more force generators 1142 may include one or more gas springs 1132. Pressure gauge 1138 may be operatively coupled to indicate the pressure within one or more gas springs 1132.

FIG. 1-C is a perspective view 1100C depicting further aspects of an exemplary compression system 1100. Force generators 1142 may include two or more force generators 1142, 1142'. Force generators 1142 may include one or more of: a gas spring 1132, a mechanical spring, a clamp, a hydraulic actuator, a magnetic actuator, a piezoelectric actuator, or a weight. For example, force generators 1142 may include one or more gas springs 1132, 1132'. In various embodiments, force generators 1142 may be selected to have an operational region of relatively constant or consistent force. Accordingly, the pressure generated within flexible reservoir 1104 may be kept relatively constant while contents of the flexible reservoir 1104 are being directed out of flexible reservoir 1104. Consistent pressure may lead to consistent flow and a consistent shear rate, which may be selected effective to avoid damage to particles. For example, a pressure may be maintained to provide a shear rate below a desired threshold, for example, a platelet activation threshold. Suitable force generators for providing such consistent or constant pressure may include two or more gas springs 1132, 1132'.

A gas pressure source 1136 may be operatively coupled to the two or more gas springs 1132, 1132'. Gas pressure source 1136 may include one or more of: a manual air pump, a battery powered air pump, a line-powered air compressor, a gas generator, a pressurized gas reservoir, and the like.

In some embodiments, a controller 1146 may be operatively coupled to the one or more force generators 1142. Controller 1146 may be configured to control one or more force generators 1142 effective to control the pressure applied to liquid mixture 1106 contained in flexible reservoir 1104. Controller 1146 may be configured to control the pressure generated by one or more force generators 1142 in the liquid mixture 1106 contained in the flexible reservoir 1104 within a range in PSI of about one or more of ±: 5, 4, 3, 2, and 1. A valve 1148 may be operatively coupled to output 1122 of flexible reservoir 1104. Valve 1148 may be manual, or may be operatively coupled to the controller 1146 and the output 1122 of the flexible reservoir 1104. Controller 1146 may be configured to operate the valve 1148 to direct the supernatant 1118 from the flexible reservoir 1104 through the valve 1148.

In several embodiments, a level indicator 1111b may be operatively coupled to base substrate 1108 to indicate an orientation of base substrate 1108 with respect to gravity. One or more of base substrate 1108 and compression substrate 1112 may define at least one via 1150. Via 1150 may be configured to provide access through one or more of base substrate 1108 and compression substrate 1112 to one or more of output 1122 of flexible reservoir 1104 and an input (not shown) of the flexible reservoir 1104. Base substrate 1108 and compression substrate 1112 each may independently include one or more of: a metal, a ceramic, a glass, a polymer, or a fiber-reinforced composite. At least one of base substrate 1108 and compression substrate 1112 may include a clear portion configured to permit visual inspection of flexible reservoir 1104 between the base substrate 1108 and the compression substrate 1112. For example, it may be desirable to examine supernatant 1118, subnatant 1120, or sediments or other components within flexible reservoir 1104 to monitor the progress of sedimentation. In various embodiments, a pressure gauge 1138 may be operatively coupled to indicate the pressure within the force generators 1142. Base substrate 1108 and compression substrate 1112 each may include a substantially flat face configured to contact the respective first and second faces of the flexible reservoir 1104. Base substrate 1108 and compression substrate 1112 together may be configured to contact flexible reservoir 1104 in the form of a blood bag.

FIG. 1-D is a block diagram 1200D depicting aspects of an exemplary apparatus 1200 for separating WB. In various embodiments, apparatus 1200 may include any suitable sedimentation system 1202, e.g., sedimentation system 1100 as described herein. The sedimentation system may be configured to separate the WB into a supernatant 1118 including platelet rich plasma (PRP) and a subnatant 1120 including red blood cells (RBC). Apparatus 1200 may include at least one platelet concentrating device 1204. Platelet concentrating device 1204 may be configured to separate a platelet concentrate (PC) 1110 and a platelet poor plasma (PPP) 1112 from supernatant 1118 including the PRP. Platelet-concentrating device 1204 may include one or more of: a filter, a controlled incremental filtration (CIF) device, a centrifuge, an electrophoresis device, a chromatography column, a fluid evaporator, a sedimentation device, a deterministic lateral displacement device, a plasma skimmer, a microfluidic crossflow filtration device, a pinched flow fraction device, a hydrodynamic filtration device, a tubular pinch device, a Dean flow fractionation device, a margination device, a magnetic separator, an ultrasound focusing device, a density gradient separator, and the like.

For example, platelet concentrating device 1204 may include any CIF device described herein, such as CIF device 100. For example, apparatus 1200 may include platelet-concentrating CIF device 1153. FIG. 1-E is a perspective view 1200E depicting further aspects of an exemplary apparatus 1200 for separating and reducing the leukocyte concentration in the components of WB. For example, platelet-concentrating CIF device 1153 may be operatively coupled to the sedimentation system to receive supernatant 1118 including the PRP. CIF device 1153 may be configured to separate a platelet concentrate (PC) 1110 and a platelet poor plasma (PPP) 1112 from supernatant 1118 including the PRP. In some embodiments, apparatus 1200 may include one or more CIF device leukocyte reduction stages 1154 operatively coupled between the sedimentation system and platelet-concentrating CIF device 1153. Leukocyte reduction stages 1154 may be configured to remove at least a portion of leukocytes comprised by the supernatant 1118. For example, one or more leukocyte reduction stages 1154 may be operatively coupled to receive one or more of the PC or the PPP from an output 1122 of platelet-concentrating CIF device 1153. Each of one or more leukocyte reduction stages 1154 and platelet-concentrating CIF device 1153 may be operatively coupled to one or more reservoirs, e.g., reservoirs 1152, 1152', 1152", 1152''', 1152'''', and the like. One or more leukocyte reduction stages 1154 may be configured to remove at least a portion of leukocytes comprised by the PC or the PPP. One or more leukocyte reduction stages 1154 may be operatively coupled to the sedimentation system to receive the subnatant 1120. One or more leukocyte reduction stages 1154 may be configured to remove at least a portion of leukocytes comprised by the subnatant 1120. One or more leukocyte reduction stages 1154 may include any device known to the art for removing leukocytes, for example, one or more of: a leukocyte reducing filter and a leukocyte-reducing microfluidic crossflow filtration device. Optionally, a standard filter, e.g., a woven-mesh inline RBC trap filter (not shown) may be employed to remove RBCs. A leukocyte-reducing microfluidic crossflow filtration device may be designed, constructed and operated according to the principles described for CIF devices herein, for example, by selecting $f_{gap}$ corresponding to separating leukocytes according to larger size as compared to RBCs or platelets.

In various embodiments, the sedimentation system may include one or more of: a compression sedimentation system 1100, a centrifuge, and a passive gravity sedimentation device. For example, the sedimentation system 1202 of apparatus 1200 may include any embodiment or feature described for sedimentation system 1100 herein.

In some embodiments, apparatus 1200 may include at least one controlled incremental filtration device, including any CIF device described herein, such as CIF device 100, or any other CIF device designed, constructed, or operated according to the CIF devices described herein. For example, apparatus 1200 may include platelet-concentrating CIF device 1153, which may include any aspects of CIF device 100 as shown in FIGS. 1-J, 1-K, 1-L, 1-M, 1-N, 1-O, 1-P, and 1-Q.

FIG. 1-F is a flow diagram depicting an exemplary method 1300 for compression sedimentation. In various embodiments, the method may include 1302 providing a flexible reservoir including a liquid mixture. The liquid mixture may include two or more particulate distributions. The two or more particulate distributions may be characterized by one or more of different effective average particulate diameters and different particle densities. Method 1300 may include 1304 sedimenting the liquid mixture in the flexible reservoir to form a supernatant and a subnatant. The supernatant may include at least a first particulate distribution. The first particulate distribution may be characterized by a first effective average particulate diameter. The first particulate distribution may be characterized by a first particulate density. The subnatant may include at least a second particulate distribution. The second particulate distribution may be characterized by a second effective average particulate diameter. The second particulate distribution may be characterized by a second particulate density.

For example, the liquid may be WB, which includes a number of particulate distributions characterized by different effective average particulate diameters and densities, such as platelets, leukocytes, and red blood cells. Sedimenting the whole blood may include forming the supernatant including platelet rich plasma (PRP). Sedimenting the whole blood may include forming the subnatant may include red blood cells (RBCs). The sedimenting may be performed under gravity. Sedimenting the liquid mixture in the flexible reservoir to form the supernatant and the subnatant may be conducted for a time in minutes of less than about one or more of: 180, 120, 90, 80, 70, 60, 50, 40, 30, 25, 20, 15, 10, 5, and 1. The method may include pressurizing the flexible reservoir, including contents of the flexible reservoir, such as one or more of: the liquid mixture, the supernatant, and the subnatant. Pressurizing may include compressing the flexible reservoir between two substrates using one or more of: gas pressure, a gas spring, a mechanical spring, a clamp, a hydraulic actuator, a magnetic actuator, a piezoelectric actuator, and a weight. Pressurizing may include compressing the flexible reservoir between two substrates using one or more of: gas pressure and a gas spring driven by the gas pressure. Providing the gas pressure from a gas pressure source may include using one or more of: a manual air pump, a battery powered air pump, a line-powered air compressor, a gas generator, and a pressurized gas reservoir. Pressurizing may include generating a pressure within the flexible reservoir within a range in PSI of one or more of about: 0.5 to 40, 0.5 to 20, and 1 to 20. Pressurizing may include automatically controlling the pressure generated in the flexible reservoir within a range in PSI of about one or more of ±: 5, 4, 3, 2, and 1.

In some embodiments, the method may include directing one or more of the supernatant and the subnatant through the output of the flexible reservoir. The directing may include placing a first end of the flexible reservoir proximal to the output at a higher elevation with respect to gravity compared to a second end of the flexible reservoir distal to the output. The directing may include sequentially directing the supernatant and the subnatant through the output of the flexible reservoir, e.g., directing the supernatant before the subnatant, or directing the subnatant before the supernatant. The method may include directing the supernatant through the output of the flexible reservoir into a storage reservoir. The method may include contacting the subnatant with a storage additive. The method may include contacting a storage additive to the subnatant in the flexible reservoir; and one of: directing the storage additive and the subnatant through the output of the flexible reservoir to a storage reservoir, and storing the additive and the subnatant together in the flexible reservoir for a period of time. The method may include sedimenting the liquid mixture in the flexible reservoir to form the supernatant and the subnatant using a flat substrate. The flat substrate may be substantially to gravity within about ±10 degrees. The method may include providing the flexible reservoir in the form of a blood bag.

FIG. 1-G is a flow diagram depicting an exemplary method 1400 for separating WB. Method 1400 may include 1402 providing a flexible reservoir including the WB. Method 1400 may include 1404 pressurizing the flexible reservoir. The flexible reservoir may include one or more of: the WB, the supernatant including the PRP, and the subnatant including the RBC to a pressure. Method 1400 may include 1406 sedimenting the WB in the flexible reservoir for a period of time to form a supernatant including a platelet rich plasma (PRP) and a subnatant including red blood cells (RBC). Method 1400 may include conducting operation 1404 followed by operation 1406 or conducting operation 1406 followed by operation 1404. Method 1400 may include 1408 using the pressure to direct one or more of the supernatant including the PRP and the subnatant including the RBC to a secondary separation process.

In various embodiments, the period of time may include sedimenting the liquid mixture in the flexible reservoir to form the supernatant and the subnatant for a time in minutes of less than about one or more of: 180, 120, 90, 80, 70, 60, 50, 40, 30, 25, 20, 15, 10, 5, and 1.

In some embodiments of method 1400 the WB may be characterized by a WB platelet activation value, for example, before sedimenting. The supernatant including the PRP may be characterized by a PRP platelet activation value, e.g., after sedimentation. The PRP platelet activation value may be a percentage of the WB platelet activation value of less than one or more of about: 150, 145, 140, 135, 130, 125, 120, 115, 110, 105, 104, 103, 102, 101, and 100. Each platelet activation value may be a fraction of platelets expressing a marker for P-Selectin expression.

In several embodiments, operating the platelet concentrating process on the supernatant may form a platelet concentrate (PC) and a platelet poor plasma (PPP). The PC may be formed characterized by a PC platelet activation value. The PC platelet activation value may be a percentage of the WB platelet activation value of less than one or more of about: 150, 145, 140, 135, 130, 125, 120, 115, 110, 105, 104, 103, 102, 101, and 100.

In various embodiments, the supernatant may include the PRP and leukocytes. The method may include removing at least a portion of the leukocytes from the supernatant to form a leukocyte-depleted supernatant including the PRP. The leukocyte-depleted supernatant including the PRP may be characterized by a leukocyte-depleted PRP platelet activation value. The leukocyte-depleted PRP platelet activation value may be a percentage of the WB platelet activation value of less than one or more of about: 150, 145, 140, 135, 130, 125, 120, 115, 110, 105, 104, 103, 102, 101, and 100. Removing at least a portion of the leukocytes from the supernatant may include contacting the supernatant including the PRP and the leukocytes to one or more of: a leukocyte filter and a leukocyte-reducing microfluidic cross-flow filtration device. For example, the method may include subjecting the leukocyte-depleted supernatant including the PRP to the secondary process to form one or more of a leukocyte-depleted PC and a leukocyte-depleted PPP. The subnatant may include the RBC and leukocytes, and the method may include removing at least a portion of the leukocytes from the subnatant to form a leukocyte-depleted subnatant including the RBC. Removing at least a portion of the leukocytes from the subnatant may include contacting the subnatant including the RBC and the leukocytes to one or more of: a leukocyte filter and a leukocyte-reducing microfluidic crossflow filtration device.

In various embodiments, the method may include sedimenting the WB in the flexible reservoir to form the supernatant and the subnatant under gravity. Sedimenting the WB in the flexible reservoir to form the supernatant and the subnatant may be conducted for a time in minutes of less than about one or more of: 180, 120, 90, 80, 70, 60, 50, 40, 30, 25, 20, 15, 10, 5, and 1. The method may include pressurizing the flexible reservoir including one or more of: the WB, the supernatant, and the subnatant. The pressurizing may include compressing the flexible reservoir between two substrates using one or more of: gas pressure, a gas spring, a mechanical spring, a clamp, a hydraulic actuator, a magnetic actuator, a piezoelectric actuator, a weight, and the like. The pressurizing may include compressing the flexible reservoir between two substrates using one or more of: gas pressure and a gas spring driven by the gas pressure. The method may include providing the gas pressure from a gas pressure source including one or more of: a manual air pump, a battery powered air pump, a line-powered air compressor, a gas generator, and a pressurized gas reservoir. The pressurizing may include producing a pressure in the flexible reservoir including one or more of: the WB, the supernatant, and the subnatant. The method may include controlling the pressure within a range in PSI of one or more of about: 0.5 to 40, 0.5 to 20, and 1 to 20. The method may include controlling the pressure automatically controlling the pressure generated in the flexible reservoir within a range in PSI of about one or more of ±: 5, 4, 3, 2, and 1.

In some embodiments, directing one or more of the supernatant and the subnatant through the output of the flexible reservoir may include placing a first end of the flexible reservoir proximal to the output at a higher elevation with respect to gravity compared to a second end of the flexible reservoir distal to the output. The method may include sequentially directing the supernatant and the subnatant through the output of the flexible reservoir. Further, for example, directing the subnatant may include the RBC through the output of the flexible reservoir into a storage reservoir. The subnatant including the RBC may be contacted with a RBC storage additive. The RBC storage additive may be contacted to the subnatant including the RBC in the flexible reservoir. The method may include directing the RBC storage additive and the subnatant including the RBC through the output of the flexible reservoir to a storage reservoir. The method may include storing the RBC additive and the subnatant including the RBC together in the flexible reservoir for a period of time.

In some embodiments, sedimenting the liquid mixture in the flexible reservoir to form the supernatant and the subnatant may be performed using a flat substrate. The method may include positioning the flat substrate substantially perpendicular to gravity. The method may include using the flexible reservoir in the form of a blood bag.

In several embodiments, the secondary separation process may include one or more of: filtration, controlled incremental filtration (CIF), centrifugation, electrophoresis, chromatography, fluid evaporation, sedimentation, deterministic lateral displacement, plasma skimming, microfluidic crossflow filtration, pinched flow fractionation, hydrodynamic filtration, tubular pinch fractionation, Dean flow fractionation, margination, magnetic separation, ultrasound focusing, and density gradient separation.

In various embodiments, exemplary method 1400 for separating WB may include controlled incremental filtration. The controlled incremental filtration may include any operation or feature described herein for controlled incremental filtration. For example, the controlled incremental filtration may include method 400, described below and in FIG. 4.

FIG. 1-H is a block diagram depicting a kit 1500 for compression sedimentation. Kit 1500 may include a compression sedimentation system 1502 including any aspect of the compression sedimentation systems described herein, e.g., compression sedimentation system 1100. For example, compression sedimentation system 1100 may include a compression stage 1102 configured to accept a flexible reservoir 1104. Flexible reservoir 1104 may be configured to contain a liquid mixture 1106. Compression stage 1102 may include a base substrate 1108 configured to contact a first face 1110 of flexible reservoir 1104. Compression stage 1102 may include a compression substrate 1112 configured to contact a second face 1114 of flexible reservoir 1104. Kit 1500 may include any instructions for operating a compression sedimentation system described herein, e.g., compression sedimentation system 1100. Instructions 1504 may include directing a user to compress base substrate 1108 and compression substrate 1112 together to apply a force 1116 to flexible reservoir 1104 effective to create a pressure in liquid mixture 1106.

FIG. 1-I is a block diagram depicting a kit 1600 for separating WB. Kit 1600 may include an apparatus 1602 configured to separate WB, e.g., apparatus 1200. Apparatus 1200 may include a sedimentation system 1100 configured to separate the WB into a supernatant 1118 including platelet rich plasma (PRP) and a subnatant 1120 including red blood cells (RBC). Apparatus 1200 may include any platelet concentrating device described herein, for example, platelet concentrating device 1153. For example, apparatus 1200 may include at least one platelet-concentrating device 1153 operatively coupled to sedimentation system 1100 to receive the supernatant 1118 including the PRP. Platelet concentration device 1153 may be configured to separate a platelet concentrate (PC) 1110 and a platelet poor plasma (PPP) 1112 from the supernatant 1118 including the PRP. Kit 1600 may include instructions 1604. Instructions 1604 may include directions to a user to carry any aspect of operating a sedimentation device, e.g., sedimentation device 1100, any aspect of operating an apparatus for separating WB, e.g., apparatus 1200, or any aspect of operating a platelet concentrating device 1153. For example, the set of instructions 1604 may direct a user to position a flexible reservoir 1104 including the WB in sedimentation system 1100. Instructions 1604 may direct the user to pressurize flexible reservoir 1104, including one or more of supernatant 1118 including the PRP and subnatant 1120 including the RBC to a pressure. Instructions 1604 may direct the user to sediment the WB in flexible reservoir 1104 to form a supernatant 1118 including a platelet rich plasma (PRP) and a subnatant 1120 including red blood cells (RBC). Instructions 1604 may direct the user to use the pressure to direct supernatant 1118 including the PRP to platelet-concentrating device 1153 to separate a platelet concentrate (PC) 1110 and a platelet poor plasma (PPP) 1112 from supernatant 1118.

FIGS. 1-J, 1-K, 1-L, 1-M, 1-N, 1-O, 1-P, and 1-Q depict various views of an exemplary CIF device 100 or portions thereof. FIG. 1-J is a block diagram 101A illustrating various aspects of an exemplary CIF device 100. CIF device 100 may be configured for modulating a concentration of particles 102 of a desired size in a microfluidic flow 104. It is to be understood that microfluidic flow 104 may include fluids for testing, e.g., to determine whether significant amounts of particles 102 of the desired size are present. CIF device 100 may include a substrate 106. Substrate 106 may include at least one CIF module 108. Substrate 106 may define in each CIF module 108 a central channel 110. Central channel 110 may extend along a flow path 112 between a central channel flow input 114 and a central channel flow output 116. Substrate 106 may define a plurality of micro-features 122 adjacent to central channel 110. Plurality of micro-features 122 may define a plurality of gaps 124. Plurality of micro-features 122 may separate central channel 110 from at least one side channel network 117. Plurality of gaps 124 may be configured to fluidically couple central channel 110 to side channel network 117. Side channel network 117 may extend along central channel 110 to at least one side channel output 120. Side channel network 117 may include one or more of a first side channel network portion 117a and a second side channel network portion 117b. In CIF device 100, side channel network 117 may be characterized by a decreasing flow resistance along at least a portion of flow path 112 effective to modulate concentration of particles 102 of the desired size in microfluidic flow 104. In various embodiments, the plurality of gaps 124a in first side channel network portion 117a are characterized by one or more of: a consistent flow fraction $f_{gap}$ and a plurality of different gap volumetric flow rates. In some embodiments, the plurality of gaps 124 in side channel network 117 are characterized by one or more of: a consistent flow fraction $f_{gap}$ and a plurality of different gap volumetric flow rates.

FIG. 1-K is a top view schematic 101B illustrating various aspects of first side channel network portion 117a, including features illustrated in block form in FIG. 1-A, such as microfluidic flow 104, substrate 106, CIF module 108, central channel 110, flow path 112, plurality of micro-features 122a, and plurality of gaps 124a. Further, for example, first side channel network portion 117a may include a plurality of side channel curves 119 adjacent to central channel 110. First side channel network portion 117a may include least a portion of plurality of micro-features 122a, and at least a portion of plurality of gaps 124a. Plurality of side channel curves 119 may be characterized by a corresponding plurality of lengths 121a that decrease along flow path 112. Each side channel curve 119 may fluidically couple at least one gap of plurality of gaps 124a in first side channel network portion 117a to one or more of: an adjacent gap in plurality of gaps 124a and an adjacent curve in plurality of curves 119.

FIG. 1-L is a top view schematic 101C illustrating various aspects of second side channel network portion 117b, including features illustrated in block form in FIG. 1-A, such as particles 102, microfluidic flow 104, substrate 106, CIF module 108, central channel 110, flow path 112, central channel flow input 114, central channel flow output 116, plurality of micro-features 122a, plurality of gaps 124a, and side channel output 120. Further, for example, second side channel network portion 117b may include a side channel 118 adjacent to central channel 110. Second side channel network portion 117b may include at least a portion of plurality of micro-features 122b. Second side channel network portion 117b may include at least a portion of plurality of gaps 124b. Side channel 118 may be characterized by a flow cross-section 139 (see FIG. 1-Q). Flow cross-section 139 may increase along flow path 112 such that plurality of gaps 124b in second side channel network portion 117b are characterized by one or more of: a consistent flow fraction $f_{gap}$ and a plurality of different gap volumetric flow rates.

Referring again to FIG. 1-A, in some embodiments, side channel network 117 may include first side channel network portion 117a followed by second side channel network portion 117b in sequence along flow path 112. In several embodiments, CIF device 100 may include two of side channel networks 117, 117'. Side channel networks 117, 117' may be adjacent to central channel 110. For example, two side channel networks 117, 117' may be separated by central channel 110 and may be located on either side of central channel 110.

Referring to FIG. 1-K, for example, for two side channel networks 117, 117', substrate 106 may define two first side channel networks 117a, 117a' including at least two pluralities of side channel curves 119, 119' adjacent to central channel 110 and at least two pluralities of micro-features 122a, 122a'. At least two pluralities of side channel curves 119, 119' may be characterized by at least two corresponding pluralities of lengths 121a, 121a' that decrease along flow path 112. Central channel 110 may be separated from each of at least two pluralities of side channel curves 119, 119' by each plurality of micro-features 122a, 122a'. At least two pluralities of micro-features 122a, 122a' may define at least two pluralities of gaps 124a, 124a'. At least two pluralities of gaps 124a, 124a' may be configured to fluidically couple central channel 110 and pluralities of side channel curves 119, 119' through pluralities of micro-features 122a, 122a'. Each of pluralities of side channel curves 119, 119' may fluidically couple at least one corresponding gap of pluralities of gaps 124a, 124a' in first side channel network portion 117a to one or more of: an adjacent corresponding gap in pluralities of gaps 124a, 124a' and an adjacent corresponding curve in pluralities of side channel curves 119, 119'.

Referring to FIG. 1-M, for example, for side channel networks 117, 117', substrate 106 may define two second side channel network portions 117b, 117b' including at least two side channels 118, 118' adjacent to central channel 110 and at least two pluralities of micro-features 122b, 122b'. Central channel 110 may be separated from each of side channels 118, 118' by each plurality of micro-features 122b, 122b'. Pluralities of micro-features 122b, 122b' may define at least two pluralities of gaps 124b, 124b'. Pluralities of gaps 124b, 124a' may be configured to fluidically couple central channel 110 and side channels 118, 118' through pluralities of micro-features 122b, 122b'.

In various embodiments, corresponding associated features may be indicated by similar feature numbers and similar description exemplification in the FIGS., e.g., micro-features 122 and 122', but distinguished by the prime symbol. For example, substrate 106 may define at least two side channels 118, 118', any description herein referring to at least one side channel 118 or features associated with at least one side channel 118, such as micro-features 122', may correspondingly extend to at least one side channel 118' or corresponding features thereof, such as micro-features 122'. Further, for example, wherein substrate 106 may define at least two side channels 118, 118', each side channel 118, 118' and corresponding associated features thereof may be the same or different. For example, side channel 118 and associated features thereof may be a mirror image with respect to side channel 118' and corresponding associated features thereof across central channel 110 along at least a portion of flow path 112. For example, depths 142 and 142', may be the same or different, e.g., the same. Further, for example, plurality of micro-features 122 and plurality of gaps 124 may have the same or different dimensions, e.g., the same, compared to plurality of micro-features 122' and plurality of gaps 124' along at least a portion of flow path 112. Also, for example, plurality of micro-features 122 and plurality of gaps 124 may be aligned or offset, e.g., aligned, along at least a portion of flow path 112 with respect to plurality of micro-features 122' and plurality of gaps 124'. In various embodiments, corresponding features of central channel 110 may be the same or different, e.g., the same, as corresponding features of side channels 118 and/or 118'. For example, depths 140, 142, and 142' may be the same or different, e.g., the same. It is explicitly contemplated all corresponding associated features indicated herein by similar feature numbers and distinguished by the prime symbol may be the same or different in such manner.

FIG. 1-N is a cross-section view 101D along flow path 112, illustrating various aspects of exemplary CIF device 100. FIG. 1-N is a close-up top view 101E along flow path 112, illustrating various aspects of exemplary CIF device 100 in detail. Plurality of gaps 124 in each CIF module 108 may be characterized by an average gap cross-sectional area 126 parallel to flow path 112. Average gap cross-sectional area 126 may be sized compared to particles 102 of desired size effective to mitigate or eliminate fouling of plurality of gaps 124 by particles 102. For example, gaps of size comparable to the desired size may be fouled or obstructed by particles 102. Selecting average gap cross-sectional area 126 to be large compared to particles 102 may mitigate or eliminate such fouling. Average gap cross-sectional area 126 may be sized compared to particles 102 of desired size effective to mitigate or eliminate steric exclusion of particles 102 by plurality of gaps 124. For example, conventional size exclusion filters function by physically or sterically excluding particles on the basis of size using gaps that are smaller than the particles to be excluded. Selecting average gap cross-sectional area 126 to be large compared to particles 102 may mitigate or eliminate such steric size exclusion, such that gaps 124 may exclude particles 102 based on microfluidic flow behavior in CIF device 100, even though average gap cross-sectional area 126 is large compared to particles 102. Each gap in plurality of gaps 124 in one or more of first side channel network 117a and second side channel network 117b may be characterized by substantially a same cross-sectional flow area 126 in a plane parallel to flow path 112. Plurality of gaps 124, for example, in one or more of first side channel network 117a and second side channel network 117b may be substantially equally spaced along flow path 112. Plurality of gaps 124 in each CIF module 108 may include a number of gaps 124 of at least about one or more of: 50, 75, 100, 150, 200, 250, 500, 750, 1,000, 2,500, 5,000, 7,500, 10,000, 50,000, 100,000, 500,000, and 1,000,000, or a range between any two of the preceding values.

In various embodiments, plurality of gaps 124 in one or more of first side channel network 117a and second side channel network 117b may be characterized by an average aspect ratio of a width 144 of each gap 124 parallel to flow path 112 to a depth 142 of each gap 124 in substrate 106. The aspect ratio of width 144 to depth 142 may be of less than about one or more of about: 16:1, 15:1, 10:1, 5:1, 4:1, 3:1, 2:1, 1:1, 1:2, 1:3, 1:4, 1:5, 1:10, 1:15, 1:20, 1:25, and 1:30. Plurality of gaps 124 may be characterized by an average gap depth 142 in substrate 106. Channel 110 may be characterized by a depth 140 in substrate 106. Average gap depth 142 may be a percentage of depth 140 of about one or more of: 5, 6, 7, 8, 9, 10, 15, 20, 25, 30, 40, 50, 60, 70, 80, 90, and 100. Depth 140 may be a value in μm of greater than one or more of about: 5, 10, 15, 20, 25, 30, 35, 40, 45, 50, 75, 100, 125, 150, 200, 250, 300, 400, and 500.

In some embodiments, central channel 110 and plurality of gaps 124 may, in one or more of first side channel network 117a and second side channel network 117b being respectively characterized by a central channel width 136 perpendicular to both flow path 112 and depth 140 of central channel 110. Central channel 110 and plurality of gaps 124 may be characterized by an average gap width 144 parallel to flow path 112. Average gap width 144 may be greater than a percentage of width 136 of one or more of about: 10, 20, 21, 22, 23, 24, 25, 30, 35, 40, 45, and 50.

FIG. 1-O is a close-up perspective view 101F along flow path 112, illustrating various aspects of exemplary CIF device 100. In various embodiments, central channel 110 in each CIF module 108 may be fluidically coupled to an input source 128 through central channel flow input 114. Further, for example, side channel network 117 may be fluidically coupled to input source 128 through plurality of gaps 124 to central channel 110. Central channel 110 may be fluidically coupled to a retentate output reservoir 130. Side channel network 117 may be fluidically coupled to a filtrate output reservoir 132.

Referring to FIG. 1-P, flow path 112 may include one or more turns 134 in substrate 106. Each CIF module 108 may be configured to provide a flow path length in cm of at least one or more of about: 0.1, 0.5, 0.75, 1, 2, 2.5, 5, 7.5, 10, 15, 20, 25, 50, 75, 100, 250, 500, and 1000, or a range between any two of the preceding values.

FIG. 1-Q is a cross section view 101I1 perpendicular to flow path 112, illustrating various aspects of second side channel network portion 117b in exemplary CIF device 100. In several embodiments, second side channel network portion 117b may be characterized by a ratio of a cross-sectional area 139 of side channel 118 to a cross-sectional area 137 of central channel 110. Cross-sectional areas 137, 139 may be perpendicular to flow path 112. The ratio of cross-sectional areas 137, 139 may increase along at least a portion of flow path 112. In some embodiments, the ratio of cross-sectional areas 137, 139 may increase along at least a portion of flow path 112 according to a width 138 of at least one side channel 118 and a width 136 of central channel 110. Each width 136, 138 may be perpendicular to both flow path 112 and a depth 140 of central channel 110 in substrate 106. Flow cross-sectional area 137 may be constant along flow path 112, e.g., along second side channel network portion 117b. Further, for example, flow cross-sectional area 139 of side channel 118 may increase along flow path 112. Each CIF module 108 may be characterized along second side channel network portion 117b by a flow cross-sectional area 137 of central channel 110 perpendicular to flow path 112. Flow cross-sectional area 137 may be, for example, constant, increasing, or decreasing along flow path 112. Further, for example, cross-sectional area 139 of side channel 118 may be constant, increasing, or decreasing along flow path 112.

In several embodiments, CIF device 100 may be characterized at least in part as a function of $f_{gap}$ according to:

$$R_s(i) = \frac{1 - 2f_{gap}}{\frac{1}{R_s(i-1)} + \frac{f_{gap}}{R_c}}, \text{ and} \quad \text{(eq. 1)}$$

$$R(w, d, \mu, L) = \frac{12\mu L}{dw^3}\left[1 - \frac{192w}{d} \cdot \sum_{n=1,3,5,\ldots}^{\infty} \frac{\tanh\left(\frac{n\pi d}{2w}\right)}{(n\pi)^5}\right]^{-1}, \quad \text{(eq. 2)}$$

The symbol $R_c$ may represent flow resistance of central channel 110. The symbol $R_s(i-1)$ may represent flow resistance in a portion of at least one side network 117 between a gap i−1 and a gap i in plurality of gaps 124. The increment symbol i may be increased by 1 for each gap in plurality of gaps 124 along flow path 112. The symbol $R_s(i)$ may represent flow resistance in a portion of at least one side network 117 between the gap i and a gap i+1 in plurality of gaps 124. The symbol R(w, d, p, L) may represent resistance of a channel segment in a portion of central channel 110 or at least one side network 117. The symbol w may represent a width corresponding to approximating the channel segment as a rectangular channel. The symbol d may represent a depth corresponding to approximating the channel segment as a rectangular channel. The symbol L may represent a length corresponding to approximating the channel segment as a rectangular channel. The symbol p may represent a viscosity of the fluid. Each L may correspond to a length of the channel segment along side channel 118 between a corresponding pair of gaps in plurality of gaps 124.

In various embodiments, CIF device 100 may be characterized as follows. At least a portion of plurality of gaps 124 may be characterized by a flow fraction $f_{gap}$ compared to a volumetric flow $Q_c(i)$ through central channel 110 at the gap i. The flow fraction $f_{gap}$ may be less than one or more of about: 0.01, 0.0075, 0.005, 0.0025, 0.001, 0.00075, 0.0005, 0.00025, 0.0001, 0.000075, 0.00005, 0.000025, and 0.00001. Upon conducting a microfluidic flow using a mixture of 1% w/w 4 μm polystyrene microbeads in water at a temperature of 25° C. and a flow pressure of 2 PSI through each CIF module 108, flow fraction $f_{gap}$ may be an average characterized by a percent standard deviation among plurality of gaps 124 of less than about ±1, 2.5, 5, 7.5, 10, 15, and 20. Each CIF module 108 may be configured, upon conducting the microfluidic flow using a mixture of 1% w/w 4 μm polystyrene microbeads in water at a temperature of 25° C. and a flow pressure of 2 PSI, to concentrate particles 102 of the desired size in microfluidic flow 104. The concentration, from a starting particle concentration at central channel flow input 114 to a final concentration at central channel flow output 116 may include a concentration factor of one or more of about: 1.5:1, 2:1, 2.5:1, 3:1, 3.5:1, 4:1, 5:1, 7.5:1, 10:1, 15:1, 20:1, 25:1, 50:1, 75:1, 100:1, 125:1, 150:1, 200:1, and 250:1. Each CIF module 108 may be configured to retain a percentage of particles 102 in microfluidic flow 104. The percentage of particles 102 retained may be at least one or more of about: 50, 55, 60, 65, 70, 75, 80, 85, 90, 95, 97.5, 99, and 100.

In various embodiments, the desired size of particles 102 may be characterized by an effective average diameter in μm of greater than one or more of about: 0.5, 1, 1.2, 1.4, 1.6, 1.8, 2, 2.5, 3, 3.5, 4, 4.5, 5, 7.5, 10, 15, 20, 25, 50, 75, 100, 125, and 150. Plurality of gaps 124 may be configured in each CIF module 108 with an average gap cross-sectional area 126 parallel to flow path 112. Average gap cross-sectional area 126 may be greater than the desired size of particles 102 to be separated from the microfluidic flow. Average gap cross-sectional area 126 may be greater than the desired size of particles 102 by a factor of one or more of about: 2:1, 3:1, 4:1, 5:1, 7.5:1, 10:1, 15:1, and 20:1.

In various embodiments, particles 102 may include one or more of: red blood cells, platelets, white blood cells, circulating tumor cells, stem cells, effete stored erythrocytes, T-cells derived from autologous T-cell expansion, organic microparticles, inorganic microparticles, organometallic microparticles, metallic microparticles, aerosol particles, bacteria, yeast, fungi, algae, viruses, micro-invertebrates or eggs thereof, pollen, cell or tissue fragments, cell clusters, cellular debris (e.g., cellular debris associated with DNA or RNA purification), bioreactor-produced cells or particulates, proteins, protein aggregates, prions, vesicles, liposomes, precipitates (e.g., precipitates from blood or a blood fraction, industrial process precipitates, wastewater precipitates, and the like), particulates or cells from fermented foods (e.g., particulates or cells from fermented beverages), macromolecules, macromolecular aggregates, DNA, organelles, spores, stem cells, bubbles, droplets, and exosomes. Microfluidic flow 104 may include particles 102 in a fluid. The fluid may include one or more of: whole blood or a fraction thereof; amniotic fluid; umbilical cord blood; bile; cerebrospinal fluid; skin cells; exudate; feces; gastric fluid; lymph; milk; mucus; peritoneal fluid; plasma; pleural fluid; pus; saliva; sebum; semen; sweat; synovial fluid; tears; urine; water; buffer; groundwater; seawater; rainwater; sap; animal tissue homogenate, extract, or pressing; plant tissue homogenate, extract, or pressing; wastewater; an industrial process fluid or fluid product; fermentation broth; crystallization or precipitation fluid; a food or food process intermediate (e.g., a fermented beverage); oil; inorganic solvent; organic solvent; ionic solvent; honey; syrup; lymphatic fluid; serum; and lysate.

In various embodiments, CIF module 108 may be configured capable of conducting the microfluidic flow as one or more of: a gravitationally-directed flow, a vacuum directed flow, an electroosmotic directed flow, an electrokinetic directed flow, a mechanically pumped flow, e.g., using a syringe pump; and the like. Each CIF module 108 may be configured such that a volumetric flow of central channel flow output 116 and a volumetric flow of at least one side channel output 120 are substantially equal.

In several embodiments, substrate 106 may include two or more of CIF modules 108, 108'. Substrate 106 may include an array of two or more CIF modules 108, 108' fluidically coupled in series or in parallel. For example, substrate 106 may include an array 200A of the two or more CIF modules 108, 108' fluidically coupled in series, as depicted in FIG. 2A. Substrate 106 may include an array 200B of two or more CIF modules 108, 108' fluidically coupled in parallel, as depicted in FIG. 2-B. The arrangements and flows depicted in FIGS. 2-A and 2-B are merely exemplary, and other arrangements and flows are contemplated.

CIF device 100 may further include at least one additional separation device 302 as depicted in FIG. 3. Separation devices 302, 302', 302" may be fluidically coupled to one or more of: central channel flow input 114, central channel flow output 116, and at least one side channel flow output 120. Additional separation devices 302, 302', 302" may include one or more of: a filter, a centrifuge, an electrophoresis device, a chromatography column, a fluid evaporator, a sedimentation device, a deterministic lateral displacement device, a plasma skimmer, a margination device, a magnetic separator, an ultrasound focusing device, a density gradient separator, and the like.

Substrate 106 may include one or more of: a glass, a polymer, a metal, a ceramic, and a semiconductor. Substrate 106 may include a thermoplastic polymer, e.g., polycarbonate, or an elastomeric rubber, e.g., polydimethylsiloxane. CIF device 100 may be configured to be one or more of: disposable, sterile, and sterilizable.

Figure 4:
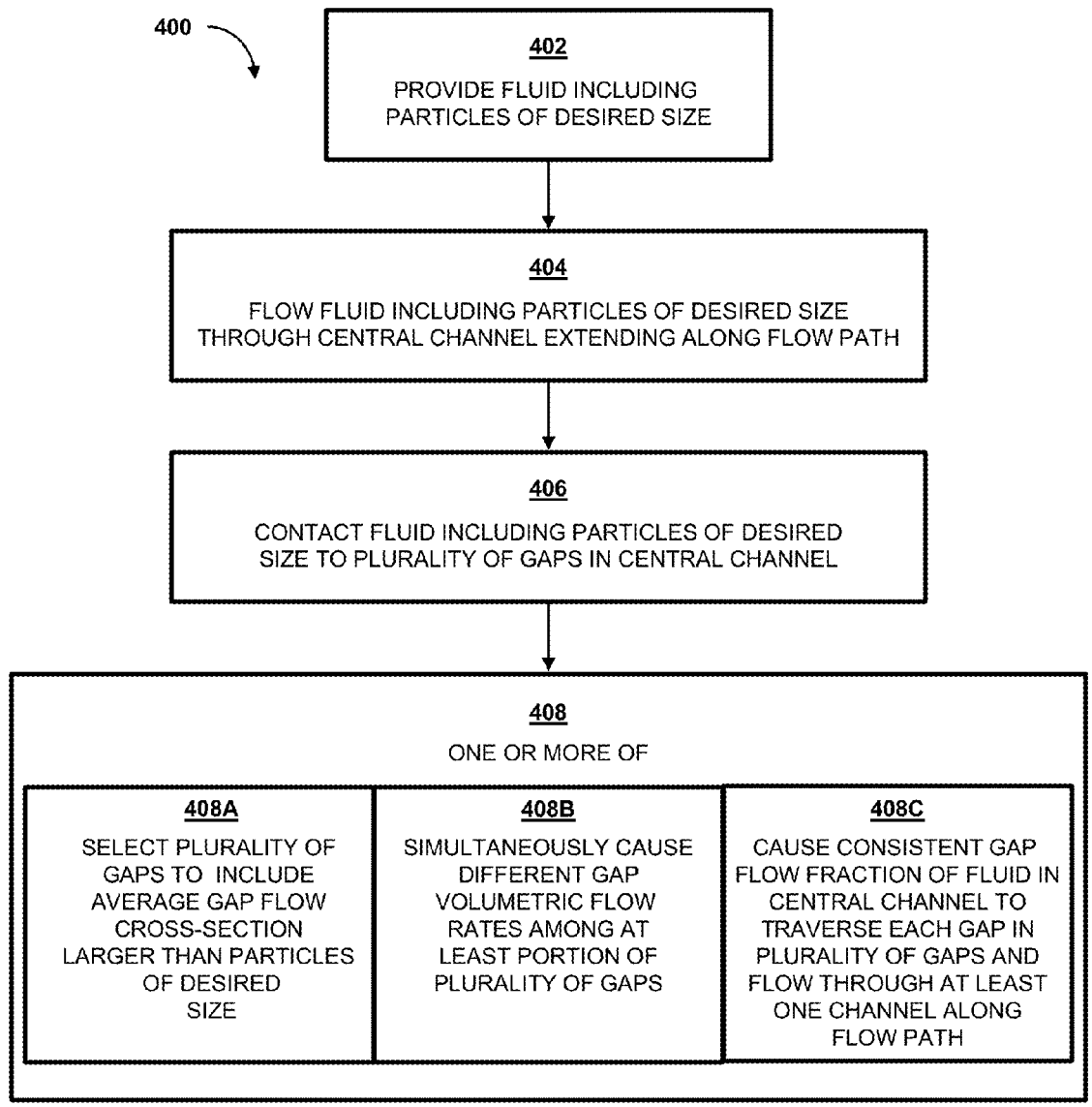
FIG. 4 is a flow diagram depicting an exemplary method for controlled incremental filtration.

FIG. 4 is a flow diagram illustrating a method 400 for controlled incremental filtration. In various embodiments, method 400 may concentrate particles of a desired size in a fluid. Method 400 may include 402 providing the fluid including the particles of the desired size. It is to be understood that "the fluid including the particles of the desired size" may include fluids for testing, e.g., to determine whether significant amounts of the particles of the desired size are present. Method 400 may include 404 flowing the fluid comprising the particles of the desired size along a flow path through a central channel. The central channel may include a plurality of gaps that fluidically couple the central channel to at least one adjacent side channel network. Method 400 may include 406 decreasing flow resistance along at least a portion of the flow path effective to modulate the concentration of particles by contacting the fluid comprising the particles of the desired size to the plurality of gaps. Method 400 may include 408, 408A selecting the plurality of gaps including an average flow cross-section larger than the particles of the desired size. Method 400 may include 408, 408B causing different gap volumetric flow rates among at least a portion of the plurality of gaps. Method 400 may include 408, 408C causing a consistent flow fraction $f_{gap}$ in the central channel to traverse each gap in the plurality of gaps and flow through the at least one side channel network along the flow path.

Method 400 may include providing the at least one side channel network. The at least one side channel network may include a first channel network portion. The first channel network portion may include a plurality of side channel curves adjacent to the central channel. The plurality of side channel curves may be characterized by decreasing length along the flow path effective to decrease the flow resistance. The at least one side channel network may include a second side channel network portion. The second side channel network portion may include a side channel adjacent to the central channel. The side channel may be characterized by an increasing flow cross-section along the flow path effective to cause one or more of: the consistent flow fraction $f_{gap}$ and the plurality of different gap volumetric flow rates. The method may include flowing the fluid through the first side channel network portion followed by the second side channel network portion in sequence along the flow path.

In some embodiments, method 400 may include selecting the plurality of gaps including an average gap cross-sectional area larger compared to the particles of desired size. Compared to gaps smaller than the particles, the larger average gap cross-sectional area larger may be effective for mitigating or eliminating fouling of the plurality of gaps by the particles. The larger average gap cross-sectional area larger may also be effective for mitigating or eliminating steric exclusion of the particles by the plurality of gaps.

In several embodiments, method 400 may include providing an average aspect ratio of a width of each gap along the flow path to a depth of each gap of less than one or more of: 16:1, 15:1, 10:1, 5:1, 4:1, 3:1, 2:1, 1:1, 1:2, 1:3, 1:4, 1:5, 1:10, 1:15, 1:20, 1:25, and 1:30. The central channel may include a depth in μm of greater than one or more of about: 5, 10, 15, 20, 25, 30, 35, 40, 45, 50, 75, 100, 125, 150, 200, 250, 300, 400, and 500. An average depth of the plurality of gaps may be greater than a depth of the central channel by a percentage of one or more of about: 5, 6, 7, 8, 9, 10, 15, 20, 25, 30, 40, 50, 60, 70, 80, 90, and 100. An average gap width along the flow path of the plurality of gaps may be greater than a width of the central channel by a percentage of one or more of about: 20, 21, 22, 23, 24, 25, 30, 40, 50, 60, 70, 80, 90, and 100. The average gap flow cross-section may be larger than the particles of the desired size by a factor of one or more of about: 2:1, 3:1, 4:1, 5:1, 7.5:1, 10:1, 15:1, and 20:1.

In various embodiments, method 400 may include providing two side channel networks adjacent to the central channel along the flow path. The method may include providing a flow path length in cm of at least one or more of about: 0.1, 0.5, 0.75, 1, 2, 2.5, 5, 7.5, 10, 15, 20, 25, 50, 75, 100, 250, 500, and 1000. The method may include providing the plurality of gaps for each at least one side channel network including a number of gaps of at least about one or more of: 50, 75, 100, 150, 200, 250, 500, 750, 1,000, 2,500, 5,000, 7,500, 10,000, 50,000, 100,000, 500,000, and 1,000,000. The method may include increasing a ratio along the flow path of a cross-sectional area of the at least one side channel to a cross-sectional area of the central channel. The ratio of the cross-sectional area of the at least one side channel to the cross-sectional area of the central channel may be increased along the flow path according to a width of the at least one side channel and a width of the central channel. The method may include increasing the ratio along the flow path, including holding the cross-sectional area of the central channel constant along the flow path and increasing the cross-sectional area of the at least one side channel along the flow path. The method may include increasing the ratio along the flow path comprising decreasing the cross-sectional area of the central channel constant along the flow path and maintaining or increasing the cross-sectional area of the at least one side channel along the flow path. The method may include increasing the ratio along the flow path including maintaining, increasing, or decreasing the cross-sectional area of the central channel along the flow path. The method may include increasing the ratio along the flow path including maintaining, increasing, or decreasing the cross-sectional area of the at least one side channel along the flow path.

In various embodiments, the method may include increasing a ratio along the flow path of a fluidic resistance of the at least one side channel to a fluidic resistance of the central channel.

In some embodiments, method 400 may include flowing the fluid characterized at least in part as a function of $f_{gap}$ according to one or more of:

$$R_s(i) = \frac{1 - 2f_{gap}}{\frac{1}{R_s(i-1)} + \frac{f_{gap}}{R_c}}, \text{ and} \quad (\text{eq. 1})$$

$$R(w, d, \mu, L) = \frac{12\mu L}{dw^3}\left[1 - \frac{192w}{d} \cdot \sum_{n=1,3,5,\ldots}^{\infty} \frac{\tanh\left(\frac{n\pi d}{2w}\right)}{(n\pi)^5}\right]^{-1}, \quad (\text{eq. 2})$$

The symbol $R_c$ may represent flow resistance of central channel 110. The symbol $R_s(i-1)$ may represent flow resistance in a portion of at least one side network 117 between a gap i−1 and a gap i in the plurality of gaps. The increment symbol i may be increased by 1 for each gap in the plurality of gaps along the flow path. The symbol $R_s(i)$ may represent flow resistance in a portion of at least one side network between the gap i and a gap i+1 in the plurality of gaps. The symbol R(w, d, p, L) may represent resistance of a channel segment in a portion of the central channel or at least one side network. The symbol w may represent a width corresponding to approximating the channel segment as a rectangular channel. The symbol d may represent a depth corresponding to approximating the channel segment as a rectangular channel. The symbol L may represent a length corresponding to approximating the channel segment as a rectangular channel. The symbol p may represent a viscosity of the fluid.

In some embodiments of method 400, the flow fraction $f_{gap}$ at a gap i may be a volumetric flow $Q_c(i)$ through the central channel at the gap i of less than one or more of about: 0.01, 0.0075, 0.005, 0.0025, 0.001, 0.00075, 0.0005, 0.00025, 0.0001, 0.000075, 0.00005, 0.000025, and 0.00001. The method may include causing the flow fraction $f_{gap}$ to have a percent standard deviation among the plurality of gaps of less than about one or more of: ±1, 2.5, 5, 7.5, 10, 15, and 20. The method may include providing each gap in the plurality of gaps with substantially the same flow cross-section. The method may include providing the plurality of gaps substantially equally spaced along the flow path.

In various embodiments, method 400 may include conducting at least one additional separation. The at least one additional separation may be conducted before or after flowing the fluid including the particles of the desired size through the central channel. The additional separation may include one or more of: filtering, centrifuging, electrophoresis, chromatography, fluid evaporation, sedimentation, deterministic lateral displacement, plasma skimming, margination, magnetic separation, ultrasound focusing device, density gradient separation, and the like.

In some embodiments, method 400 may include concentrating the particles of the desired size in the fluid in the central channel by a concentration factor of one or more of about: 1.5:1, 2:1, 2.5:1, 3:1, 3.5:1, 4:1, 5:1, 7.5:1, 10:1, 15:1, 20:1, 25:1, 50:1, 75:1, 100:1, 125:1, 150:1, 200:1, and 250:1. The method may include retaining a percentage of the particles of the desired size in the fluid in the central channel of at least one or more of about: 50, 55, 60, 65, 70, 75, 80, 85, 90, 95, 97.5, 99, and 100.

In several embodiments of method 400, the desired size of the particles may be characterized by an effective average diameter in μm of greater than one or more of about: 0.5, 1, 1.2, 1.4, 1.6, 1.8, 2, 2.5, 3, 3.5, 4, 4.5, 5, 7.5, 10, 15, 20, 25, 50, 75, 100, 125, and 150. The particles may include one or more of: red blood cells, platelets, white blood cells, circulating tumor cells, stem cells, effete stored erythrocytes, T-cells derived from autologous T-cell expansion, organic microparticles, inorganic microparticles, organometallic microparticles, metallic microparticles, aerosol particles, bacteria, yeast, fungi, algae, viruses, micro-invertebrates or eggs thereof, pollen, cell or tissue fragments, cell clusters, cellular debris (e.g., cellular debris associated with DNA or RNA purification), bioreactor-produced cells or particulates, proteins, protein aggregates, prions, vesicles, liposomes, precipitates (e.g., precipitates from blood or a blood fraction, industrial process precipitates, wastewater precipitates, and the like), particulates or cells from fermented foods (e.g., particulates or cells from fermented beverages), macromolecules, macromolecular aggregates, DNA, organelles, spores, stem cells, bubbles, droplets, exosomes, and the like. The fluid may include one or more of: whole blood or a fraction thereof; amniotic fluid; umbilical cord blood; bile; cerebrospinal fluid; skin cells; exudate; feces; gastric fluid; lymph; milk; mucus; peritoneal fluid; plasma; pleural fluid; pus; saliva; sebum; semen; sweat; synovial fluid; tears; urine; water; buffer; groundwater; seawater; rainwater; sap; animal tissue homogenate, extract, or pressing; plant tissue homogenate, extract, or pressing; wastewater; an industrial process fluid or fluid product; fermentation broth; crystallization or precipitation fluid; a food or food process intermediate (e.g., a fermented beverage); oil; inorganic solvent; organic solvent; ionic solvent; honey; syrup; lymphatic fluid; serum; lysate; and the like.

In various embodiments, method 400 may include collecting one or more of a retentate fraction from the central channel and a filtrate fraction from the at least one side network. The method may include collecting a fraction of the fluid comprising an increased or a decreased concentration of the particles of the desired size. The method may include flowing the fluid including conducting one or more of: gravitational flow, vacuum flow, electroosmotic flow, electrokinetic flow, mechanically pumped flow (e.g., using a syringe pump), and the like. The method may include providing substantially equal volumetric flows of the fluid at an output of the central channel flow and an output of the at least one side channel. The method may include operating two or more instances of the method in one or more of: parallel operation and serial operation. The method may include flowing the fluid including the particles of the desired size by flowing along one or more turns in the flow path.

FIG. 5 is a flow diagram illustrating a method 500 for designing a CIF device. The CIF device may modulate a concentration of particles of a desired size in a fluid. Method 500 may include 502 preparing a design for a CIF device. The CIF device design may include a central channel. The central channel may extend along a flow path between a central channel flow input and a central channel flow output. The CIF device design may include at least one side channel adjacent to the central channel. The at least one side channel may extend along the flow path to at least one side channel output. The central channel may be separated from the at least one side channel by a plurality of micro-features. The plurality of micro-features may define a plurality of gaps i. The plurality of gaps may be configured to fluidically couple the central channel and the at least one side channel through the plurality of micro-features. Method 500 may include 504 selecting a desired flow fraction $f_{gap}$ for the CIF device. Method 500 may include 506 determining a plurality of adjusted dimensions along the flow path. Method 500 may include 508 adapting the CIF device design to incorporate the plurality of the adjusted dimensions. Incorporating the adjusted dimensions may be effective to provide a decreasing flow resistance along at least a portion of the flow path effective to modulate the concentration of particles of the desired size in the fluid for the design for the CIF device.

In various embodiments of method 500, the adjusted dimensions along the flow path may include, in a first side network portion, a decreasing length of each of a plurality of side channel curves. The plurality of side channel curves may be adjacent to the central channel in the first side channel network portion. The adjusted dimensions along the flow path may include, in a second side network portion, an increasing ratio of a cross-sectional area of at least one side channel to a cross-sectional area of the central channel. The at least one side channel may be adjacent to the central channel in the second side network portion.

In some embodiments, method 500 may include providing one or more test CIF devices. Each of the test CIF devices may be characterized by a corresponding test flow fraction $f_{gap}$. The method may include flowing the particles of the desired size in the fluid through the one or more test CIF devices. The method may include determining the desired flow fraction $f_{gap}$ for the design for the CIF device based on each corresponding test flow fraction $f_{gap}$ in the one or more test CIF devices.

In several embodiments, method 500 may include determining the plurality of adjusted dimensions by determining a central channel flow resistance K. The method may include determining a first side channel segment flow resistance corresponding to a first side channel segment between a first pair of adjacent gaps in the plurality of gaps along the flow path. The first flow resistance may be determined according to a first functional relationship between: a viscosity of the fluid; a first effective side channel width w and a first effective channel depth d corresponding to a first cross-sectional area at the first side channel segment; and a length L of the first side channel segment. The method may include determining a second side channel segment flow resistance corresponding to a second side channel segment between a second pair of adjacent gaps in the plurality of gaps along the flow path. The second side channel segment may be located immediately downstream of the first side channel segment. The second side channel segment flow resistance may be determined according to a second functional relationship between: the central channel flow resistance, the first side channel segment flow resistance, and the desired flow fraction $f_{gap}$ for the CIF device. The method may include recalculating the first functional relationship using one or more adjusted dimensions comprising one or more of: a second effective side channel width w; a second effective channel depth d; and a second side channel length L. The one or more adjusted dimensions may be effective to cause the first side channel segment flow resistance according to the first functional relationship to equal the second side channel segment flow resistance. The one or more adjusted dimensions may be effective to cause the second side channel segment flow resistance according to the second functional relationship to be lower than the first side channel segment flow resistance by a desired amount. The method may include conducting one or more of the preceding steps for a plurality of iterations to calculate the plurality of the adjusted dimensions.

In various embodiments, method 500 may include holding the cross-sectional area of the central channel constant along the flow path and each effective channel depth d such that the ratio increases according to the one or more of: increasing the second effective side channel width w; and decreasing the second side channel length L. The side channel network may include a plurality of side channel curves characterized by a plurality of side channel curve lengths. The plurality of side channel curves may be adjacent to the central channel. The method may include progressively decreasing the plurality of side channel curve lengths along the flow path. The side channel network may include a side channel adjacent to the central channel. The method may include progressively increasing a width of the side channel along the flow path. The method may include, for each functional relationship, approximating each channel segment as a rectangular channel. The method may include recalculating the first functional relationship by numerically solving the first functional relationship for the one or more adjusted dimensions.

In some embodiments of method 500, the first functional relationship may be represented by:

$$R(w, d, \mu, L) = \frac{12\mu L}{dw^3}\left[1 - \frac{192w}{d} \cdot \sum_{n=1,3,5,\ldots}^{\infty} \frac{\tanh\left(\frac{n\pi d}{2w}\right)}{(n\pi)^5}\right]^{-1}.$$

The second functional relationship being represented by:

$$R_s(i) = \frac{1 - 2f_{gap}}{\frac{1}{R_s(i-1)} + \frac{f_{gap}}{R_c}}$$

The symbol $R_s(i-1)$ may represent the first side channel segment flow resistance. The symbol $R_s(i)$ may represent the second side channel segment flow resistance.

In several embodiments, method 500 may include selecting the plurality of gaps in the design for the CIF device characterized by an average gap cross-sectional area parallel to the central channel along the flow path. The average gap cross-sectional area may be selected larger compared to the particles of desired size effective for mitigating or eliminating fouling of the plurality of gaps by the particles. The average gap cross-sectional area may be selected larger compared to the particles of desired size effective for mitigating or eliminating steric exclusion of the particles by the plurality of gaps.

In various embodiments of method 500, the design for the CIF device may include at least two side channel networks adjacent to the central channel and at least two corresponding pluralities of the micro-features. The central channel may be separated from each of the at least two side channels by each plurality of micro-features. The at least two pluralities of micro-features may define at least two pluralities of gaps. The at least two pluralities of gaps may be configured to fluidically couple the central channel and the at least two side channels through the at least two pluralities of the micro-features. The design for the CIF device may include one or more turns in the flow path.

In some embodiments of method 500, each gap in the plurality of gaps in the design for the CIF device may be characterized by substantially the same cross-sectional flow area in a plane parallel to the flow path. For example, the plurality of gaps in the design for the CIF device may be substantially equally spaced along the flow path. The design for the CIF device may be configured to provide a flow path length in cm of at least one or more of about: 0.1, 0.5, 0.75, 1, 2, 2.5, 5, 7.5, 10, 15, 20, 25, 50, 75, 100, 250, 500, and 1000. The plurality of gaps for the design for the CIF device may include a number of gaps of at least about one or more of: 50, 75, 100, 150, 200, 250, 500, 750, 1,000, 2,500, 5,000, 7,500, 10,000, 50,000, 100,000, 500,000, and 1,000,000. The design for the CIF device may be characterized by a cross-sectional area of the central channel perpendicular to the flow path. The cross-sectional area of the central channel may be constant, increasing, or decreasing along the flow path. The design for the CIF device may be characterized by a cross-sectional area of the at least one side channel perpendicular to the flow path. The cross-sectional area of the at least one side channel may be constant, increasing, or decreasing along the flow path. The plurality of gaps in the design for the CIF device may be characterized by an average aspect ratio of a width of each gap parallel to the flow path to a depth of each gap of less than about one or more of about: 16:1, 15:1, 10:1, 5:1, 4:1, 3:1, 2:1, 1:1, 1:2, 1:3, 1:4, 1:5, 1:10, 1:15, 1:20, 1:25, and 1:30. The plurality of gaps in the design for the CIF device may be characterized by an average gap depth. The average gap depth may be greater than a percentage of a depth of the central channel of about one or more of: 5, 6, 7, 8, 9, 10, 15, 20, 25, 30, 40, 50, 60, 70, 80, 90, and 100. The central channel may be characterized by a depth in μm of greater than one or more of about: 5, 10, 15, 20, 25, 30, 35, 40, 45, 50, 75, 100, 125, 150, 200, 250, 300, 400, and 500.

In several embodiments of method 500, the central channel and the plurality of gaps may be respectively characterized by (1) a central channel width perpendicular to both the flow path and the depth of the central channel in the substrate and (2) an average gap width parallel to the flow path. The average gap width may be greater than a percentage of the width of the central channel of one or more of about: 10, 20, 21, 22, 23, 24, 25, 30, 35, 40, 45, and 50. The design for the CIF device may be configured such that compared to a volumetric flow $Q_c(i)$ through the central channel at a gap i, the desired flow fraction $f_{gap}$ is selected to be less than one or more of about: 0.01, 0.0075, 0.005, 0.0025, 0.001, 0.00075, 0.0005, 0.00025, 0.0001, 0.000075, 0.00005, 0.000025, and 0.00001. The design for the CIF device may be configured effective to provide a realized flow fraction $f_{gap}$ among the plurality of gaps characterized by a percentage standard deviation of less than about ±1, 2.5, 5, 7.5, 10, 15, and 20. The design for the CIF device may be configured effective to concentrate the particles of the desired size in the microfluidic fluid flow from a starting particle concentration at the central channel flow input to a final concentration at the central channel flow output by a concentration factor of one or more of about: 1.5:1, 2:1, 2.5:1, 3:1, 3.5:1, 4:1, 5:1, 7.5:1, 10:1, 15:1, 20:1, 25:1, 50:1, 75:1, 100:1, 125:1, 150:1, 200:1, and 250:1. The design for the CIF device may be configured effective to retain a percentage of the particles in the microfluidic fluid flow, the percentage of particles retained being at least one or more of about: 50, 55, 60, 65, 70, 75, 80, 85, 90, 95, 97.5, 99, and 100.

In various embodiments of method 500, the plurality of gaps may be configured with an average gap cross-sectional area parallel to the flow path. The average gap cross-sectional area may be greater than the desired size of the particles. The desired size of the particles may be selected with an effective average diameter in μm of greater than one or more of about: 0.5, 1, 1.2, 1.4, 1.6, 1.8, 2, 2.5, 3, 3.5, 4, 4.5, 5, 7.5, 10, 15, 20, 25, 50, 75, 100, 125, and 150. The average gap cross-sectional area may be greater than the desired size of the particles by a factor of one or more of about: 2:1, 3:1, 4:1, 5:1, 7.5:1, 10:1, 15:1, and 20:1. The particles may include one or more of: red blood cells, platelets, white blood cells, circulating tumor cells, stem cells, effete stored erythrocytes, T-cells derived from autologous T-cell expansion, organic microparticles, inorganic microparticles, organometallic microparticles, metallic microparticles, aerosol particles, bacteria, yeast, fungi, algae, viruses, micro-invertebrates or eggs thereof, pollen, cell or tissue fragments, cell clusters, cellular debris (e.g., cellular debris associated with DNA or RNA purification), bioreactor-produced cells or particulates, proteins, protein aggregates, prions, vesicles, liposomes, precipitates (e.g., precipitates from blood or a blood fraction, industrial process precipitates, wastewater precipitates, and the like), particulates or cells from fermented foods (e.g., particulates or cells from fermented beverages), macromolecules, macromolecular aggregates, DNA, organelles, spores, stem cells, bubbles, droplets, exosomes, and the like. The fluid may include one or more of: whole blood or a fraction thereof; amniotic fluid; umbilical cord blood; bile; cerebrospinal fluid; skin cells; exudate; feces; gastric fluid; lymph; milk; mucus; peritoneal fluid; plasma; pleural fluid; pus; saliva; sebum; semen; sweat; synovial fluid; tears; urine; water; buffer; groundwater; seawater; rainwater; sap; animal tissue homogenate, extract, or pressing; plant tissue homogenate, extract, or pressing; wastewater; an industrial process fluid or fluid product; fermentation broth; crystallization or precipitation fluid; a food or food process intermediate (e.g., a fermented beverage); oil; inorganic solvent; organic solvent; ionic solvent; honey; syrup; lymphatic fluid; serum; lysate; and the like.

In some embodiments of method 500, the design for the CIF device may be configured effective to passively conduct microfluidic fluid flow as one or more of: gravitational flow, vacuum flow, electroosmotic flow, electrokinetic flow, mechanically pumped flow (e.g., using a syringe pump), and the like. The design for the CIF device may be configured such that a volumetric flow of the central channel flow output and a volumetric flow of the at least one side channel output are substantially equal.

Figure 6:
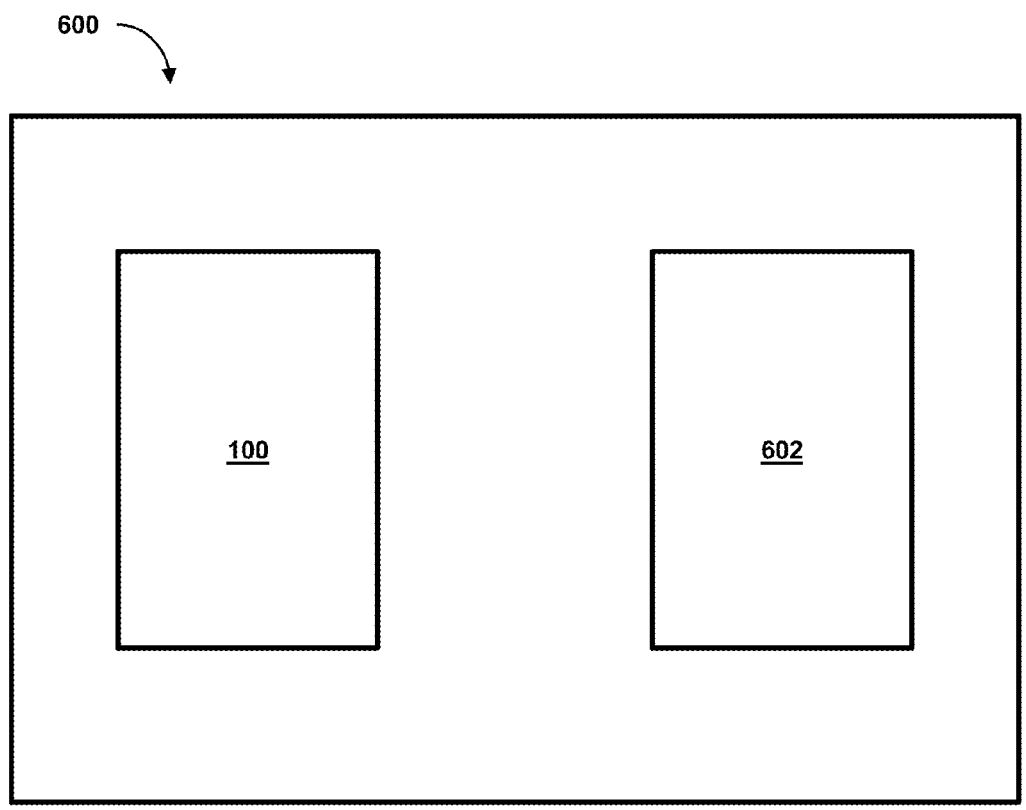
FIG. 6 is a block diagram illustrating an exemplary kit including a CIF device and instructions for conducting an exemplary method for controlled incremental filtration.

FIG. 6 is a block diagram illustrating a kit 600. Kit 600 may include any aspects of the CIF devices described herein, e.g., CIF device 100. For example, kit 600 may include CIF device 100 configured for modulating a concentration of particles 102 of a desired size in a microfluidic flow 104. CIF device 100 may include substrate 106. Substrate 106 may include at least one CIF module 108. Substrate 106 may define in each CIF module 108 a central channel 110. Central channel 110 may extend along a flow path 112 between a central channel flow input 114 and a central channel flow output 116. Substrate 106 may define a plurality of micro-features 122 adjacent to central channel 110. Plurality of micro-features 122 may define a plurality of gaps 124. Plurality of micro-features 122 may separate central channel 110 from at least one side channel network 117. Plurality of gaps 124 may be configured to fluidically couple central channel 110 to at least one side channel network 117. Side channel network 117 may extend along central channel 110 to at least one side channel output 120. Side channel network 117 may include one or more of a first side channel network portion 117a and a second side channel network portion 117a.

In CIF device 100, first side channel network portion 117a may include: a plurality of side channel curves 119 adjacent to central channel 110, at least a portion of plurality of micro-features 122a, and at least a portion of plurality of gaps 124a. Plurality of side channel curves 119 may be characterized by a corresponding plurality of lengths 121a that decrease along flow path 112. Each side channel curve 119 may fluidically couple at least one gap of plurality of gaps 124a in first side channel network portion 117a to one or more of: an adjacent gap in the plurality of gaps 124a and an adjacent curve in the plurality of curves 119.

In CIF device 100, second side channel network portion 117b may include: a side channel 118 adjacent to the central channel 110, at least a portion of plurality of micro-features 122b, and at least a portion of plurality of gaps 124b. Side channel 118 may be characterized by a flow cross-section 139. Flow cross-section 139 may increase along flow path 112 such that plurality of gaps 124b in second side channel network portion 117b are characterized by one or more of: a consistent flow fraction $f_{gap}$ and a plurality of different gap volumetric flow rates.

In CIF device 100, at least one side channel network 117 may be characterized by a decreasing flow resistance along at least a portion of flow path 112 effective to modulate the concentration of particles 102 of the desired size in microfluidic flow 104.

Kit 600 may include may include a set of instructions 602. Instructions 602 may include directions to a user to carry any aspect of operating a CIF device as described herein, for example, any aspect of method 400. For example, set of instructions 602 may include directions to a user to provide the fluid including particles 102 of the desired size. Instructions 602 may include directions to a user to flow the fluid including the particles of the desired size along a flow path through the central channel. Set of instructions 602 may include directions to a user to decrease flow resistance along at least a portion of the flow path effective to modulate the concentration of particles by contacting the fluid comprising the particles of the desired size to the plurality of gaps. Set of instructions 602 may include directions to a user to select the plurality of gaps including an average flow cross-section larger with respect to the particles of the desired size. Set of instructions 602 may include directions to a user to cause different gap volumetric flow rates among at least a portion of the plurality of gaps. Set of instructions 602 may include directions to a user to cause a consistent flow fraction $f_{gap}$ in the central channel to traverse each gap in the plurality of gaps and flow through the at least one side channel network along the flow path In various embodiments, the CIF devices described herein may promote efficiency and predictability of particle concentration in the central channel by permitting an equal amount of fluid to be taken by each side channel network from the central channel, for example, in embodiments including at least two side channels.

In some embodiments, the methods of CIF device design described herein may be used to create a CIF device mold using soft lithography, microCNC machining, laser ablation, or other well-known mold making techniques. Such techniques may simplify the design process and may allow creation of a device by changing a few, e.g., one or two parameters. The methods of CIF device design described herein may promote rapid prototyping. The methods of CIF device design described herein may facilitate production of longer CIF device flow paths capable of greater particle enrichment compared to shorter flow paths. The methods of CIF device design described herein may be simpler than complex CFD modeling techniques that may be computationally limited to a few dozen filtration points or gaps. By comparison, the methods of CIF device design described herein may be less computationally demanding and may be used to quickly generate designs including many thousands of filtration points. The methods of CIF device design described herein may reduce the number of design parameters compared to such complex CFD modeling techniques, facilitating a fast, recursive, numerical approach to generate a CAD drawing for a desired CIF device. The methods of CIF device design described herein may also be more effective than such complex CFD modeling techniques, particularly with respect to predicting effectiveness of contemplated CIF designs. The methods of CIF device design described herein may permit devices of desirable volumetric throughput that may be driven by moderate pressure, passive methods, e.g., by gravitational pressure.

In several embodiments, the CIF devices described herein may concentrate particles above a desired size in a central flow channel compared to adjacent side channels. The central channel and side channels may be separated by gaps, which may be several times larger than the particles of interest, in contrast to known crossflow filtration, which may rely primarily on simple size exclusion. The CIF devices described herein may include side channels having a width that gradually increases along the flow path of the device to provide a filtration size cutoff corresponding to the particles of desired size. This architecture may facilitate calculation of dimensions suitable to provide a consistent filter fraction $f_{gap}$ at each gap. The methods of CIF device design described herein may, by numerically determining the side channel width, permit larger gaps as the filtration points compared to known design techniques. Accordingly, the methods of CIF device design described herein may permit construction of CIF devices with deeper channels compared to known design techniques, which may mitigate or avoid feature collapse or adhesion upon de-molding.

In various embodiments, analytical solutions may be used to generate a CAD drawing in a two-step process of identification followed by implementation. Predictions of flow dynamics often fail, for example in known CFD techniques, so a test step according to the methods described herein may facilitate choosing a suitable $f_{gap}$ value for manufacturing a complete design with the desired total degree of filtration/enrichment. The quick generation of CAD designs with many filtration points enables one to filter to a higher degree in a single device and/or enrich smaller particles.

By controlling the fraction of central channel fluid that flows through each filtration point ($f_{gap}$), the methods and devices described herein permit the use of gaps much larger than the particle(s) of interest, without losing a significant amount of the particles to the side channels of the device. Such large gaps may permit the manufacture of deeper devices, which may increase throughput and expand available applications of the CIF devices. For example, the methods of CIF device design described herein may provide an effective CIF device in a manageable footprint capable of more than just 'lab on a chip' applications, for example, even while the size of the relevant particle of interest may be much smaller, such as with platelets. The methods of CIF device design described herein may provide CIF devices that are more adjustable compared to macroscopic crossflow filtration. The methods of CIF device design described herein may permit the CIF devices to be made out of inexpensive materials such as injection molded plastics without highly-specialized filtration membranes.

EXAMPLES

Experimental Considerations for Device Design and Fabrication

The CIF devices described herein may retain or deplete particles of a specified size from a complex aqueous suspension or slurry. As shown in FIGS. 1-N and 1-O, the central flow channel may have a constant width ($w_c$) and may be flanked by side channels having a width immediately downstream of gap i, $w_s(i)$ corresponding to a desired value of $f_{gap}$, and the side channel width immediately downstream of the preceding gap, $w_s(i-1)$. This recursive approach to calculating the side channel width may permit a CAD drawing of a device design to be built up quickly, using a small number of governing equations and simplifying assumptions. For example, an assumption permitting an easily-implementable model is to treat the space between gaps as nodes that may allow equalization of pressure across the width of the device. Without wishing to be bound by theory, it is believed that relatively large-mouthed (~20 µm) gaps may be used, which present only a small amount of resistance to the small amount of flow of fluid through each gap, facilitating pressure equilibration, for example, with main channel widths on the order of 100 µm. Without wishing to be bound by theory, it is believed that devices that remove on the order of 0.05% of the fluid from the central channel at each gap (i.e., $f_{gap} \sim 5 \times 10^{-4}$) may be desirable. Accordingly, a recursive equation for volumetric flow in the side and central channels at gap i, [$Q_s(i)$ and $Q_c(i)$, respectively] may be used. Once expanded, the recursive equation may describe the growth in side channel width along the length of the device corresponding to a consistent, e.g., constant, $f_{gap}$:

$$Q_s(i) = Q_s(i-1) + f_{gap} \cdot Q_c(i-1)$$

The preceding relation may be expressed in terms of pressure differential between gap I and gap i+1, ΔP(i), the resistance of a side channel segment immediately downstream of gap i, $R_s(i)$, and the central channel segment resistance, $R_c$, as:

$$\frac{\Delta P(i)}{R_s(i)} = \frac{\Delta P(i-1)}{R_s(i-1)} + f_{gap} \cdot \frac{\Delta P(i-1)}{R_c}$$

Assuming an incompressible fluid, the sum of volumetric flows through the three channel segments of a CIF device with two side channels may equal a constant. Accordingly, a ratio of ΔP(i−1) to ΔP(i) may equal $(1-2 \cdot f_{gap})^{-1}$. The preceding relation may be reformulated as:

$$R_s(i) = \frac{1 - 2f_{gap}}{\frac{1}{R_s(i-1)} + \frac{f_{gap}}{R_c}} \quad \text{(eq. 1)}$$

For example, the method for determining the width of the side channels may begin with an arbitrary side channel width at i=1, e.g., close or equal to zero. Subsequently, eq. 1 may be used to determine the width of subsequent side channels, $w_s(i)$ by adding a small amount to the value of $w_s(i-1)$ until the value of $R_s(i)$ according to eq. 2 below also satisfies eq. 1. This approach may be encoded in any number of software packages capable of numerical solutions, such as MATLAB (MathWorks, Natick, Mass.).

The fluidic resistance (R) of each channel segment may be calculated from a corresponding width (w) and depth (d) via an analytically-derived solution for a rectangular channel:

$$R(w, d, \mu, L) = \frac{12 \mu L}{d w^3}\left[1 - \frac{192 w}{d} \cdot \sum_{n=1,3,5,\ldots}^{\infty} \frac{\tanh\left(\frac{n \pi d}{2w}\right)}{(n \pi)^5}\right]^{-1} \quad \text{(eq. 2)}$$

where μ is the viscosity of the fluid, and L is the channel length, which in one embodiment is simply assumed to equal the length, along the direction of flow, of a micro-feature, e.g., a micro-pillar in the device, as shown in FIG. 1-O. In various examples, neither of μ or L affects the side channel width calculation, where the values of μ and L may be considered to be constant across the channel segments. Without wishing to be bound by theory, the assumption that the value of μ may be considered to be constant across the channel segments may not correspond to particulate solutions that are highly concentrated in the central channel and depleted in the side channels. In various examples, d and w can be reversed in the equation without affecting the validity of eq. (2), thus making the solution aspect ratio independent, in contrast to other treatments of R(w).

FIGS. 10-A-D are a series of plots illustrating the relationship between the progressive increase in side channel width along the length of a device, calculated as a function of device depth and $f_{gap}$. Each curve in FIGS. 10-A-D was generated using only equations 1 and 2 above, with an initial side channel width of zero and a central channel width of 100 um.

Example 1

CIF Device Fabrication

Desired device parameters were input into custom-written MATLAB software and the resultant design feature coordinates were exported for generating a CAD of each device. Chrome-on-glass photomasks of the CAD device designs were then used to pattern the microchannel patterns into photoresist (SU8 3050, ~100-150 μm deep) spun onto standard 4" silicon wafers and subjected to UV (i-line) exposure. Inverse polydimethylsiloxane (PDMS; SylGard 184, Dow Corning, Midland, Mich.) molds of the wafer/photoresist masters were created and sealed to PDMS-coated glass slides via air plasma oxidation. Input and output fluidic ports were created in the ~5 mm thick PDMS via biopsy punches prior to sealing. PDMS devices were then treated with polyethylene glycol (PEG) prior to the introduction of the particulate suspensions of interest. Fluid was driven through the devices by inserting into the input port an appropriate length of 1.5 mm-diameter polyethylene tubing, which was attached to a 10 mL plastic vessel and hung at heights between 1 inch to 5 feet above the device. Both the tubing and vessel were filled with a liquid buffer appropriate for the particle type(s) being studied. After a sufficient volume of fluid had passed through a given device, samples were collected from each of the output ports for analysis.

Though the above method incorporates one standard method for rapid prototyping bench-scale microfluidic devices, larger and more durable metal master molds may also be created e.g, via electroforming. Such metal master molds may be more appropriate for mass producing plastic devices via e.g. injection molding or hot embossing, since producing devices by curing PDMS is time consuming and not cost-effective in many applications. Other methods known to the art for mass producing polymeric devices may also be used.

Example 2A

CIF Two-Step Design Process for Polystyrene Bead Separation

In a first step, a number of filtration channels were tested in parallel, each with a different value of $f_{gap}$. By observing which particles were maintained or not maintained in the central channel as a function of $f_{gap}$, the appropriate $f_{gap}$ value was selected for use in patterning a complete device in step two.

Figure 11:
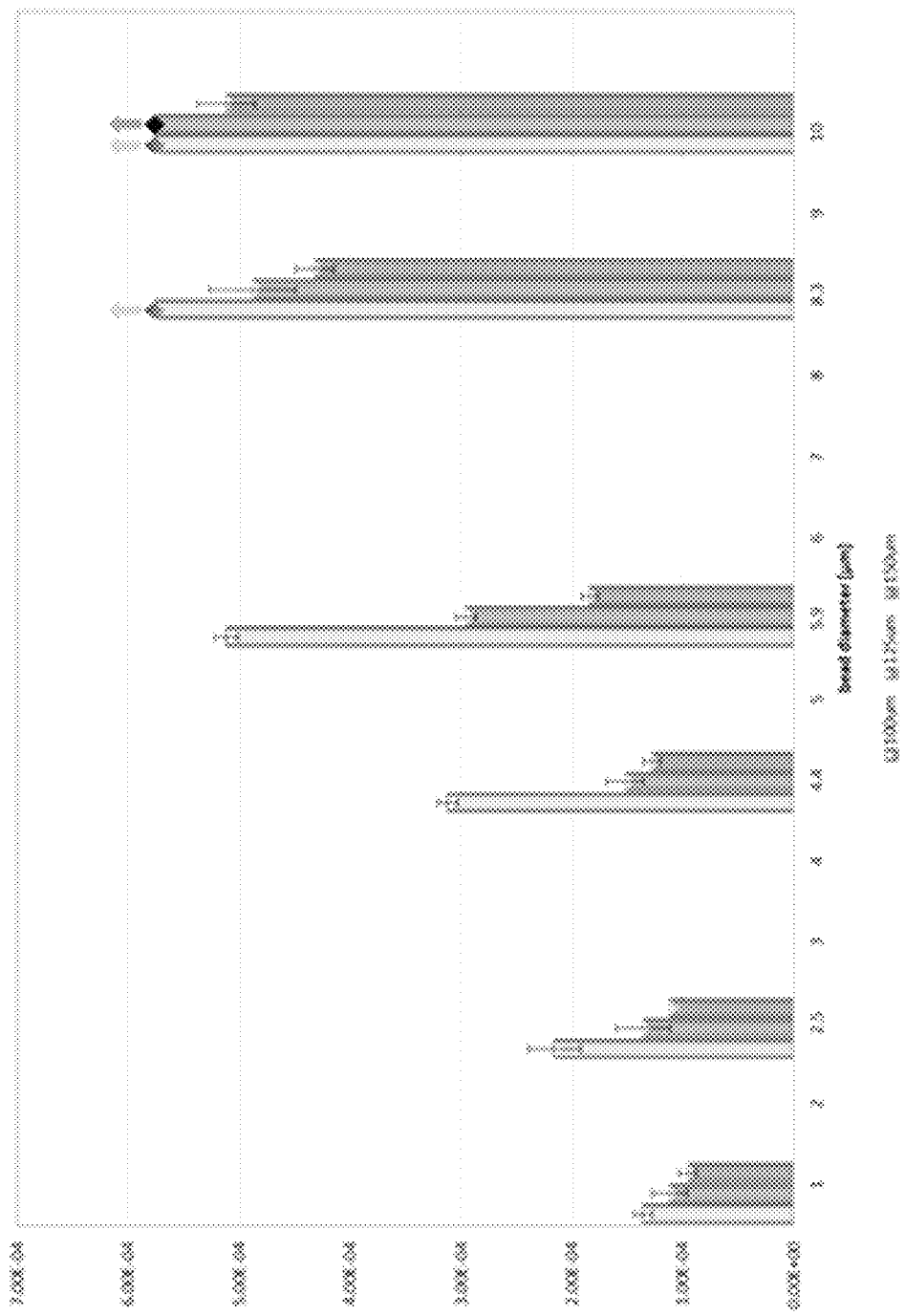
FIG. 11 is a bar graph demonstrating shows the effect of central channel width on flow fraction $f_{gap}$.

FIG. 11 presents the results of performing step one on beads of various diameters in three microchannel arrays with different central channel widths (100 μm, 125 μm, and 150 μm). In each case, a parallel array of 33 test devices was designed to explore a wide range of the degree filtration per gap, with device $f_{gap}$ values ranging linearly from $6.4 \times 10^{-5}$ (device #1) to $5.76 \times 10^{-4}$ (device #33). Arrays of devices with the given parameters were designed according to eqs. 1 and 2 and created for testing. Values for the $f_{gap}$ cutoff threshold ($f^*_{gap}$) for polystyrene beads of various diameters were determined visually by observing the $f_{gap}$ below which the beads were consistently maintained in the central flow channel. As the width of the central channel increased or the size of the particle decreased, the $f_{gap}$ limit at which particles begin to be dragged along with fluid flow through the gaps was observed to decrease. A range of $f_{gap}$ values was also tested in order to determine a desired value for the particle of interest.

Example 2B

Application of CIF Two-Step Design Based on Polystrene Bead and Platelet Separation The results in Example 2A give approximate guiding values useful for investigating particle enrichment/filtration applications more complex than simple beads in saline solution. One such application of keen practical interest is further enrichment of platelets in a suspension of PRP to levels above the AABB standard for PC. Platelets have an approximately discoid but also highly variable, non-uniform and dynamic shape, with effective diameters of ~1.5-4 µm. The behavior of PRP flowing through the same three arrays as described in FIG. 11 was investigated, with particular attention to devices in the range of #2 to #10, corresponding to $f_{gap}$ values ~1-2×10$^{-4}$. The platelets of the subjects studied consistently remained in the central flow channel for devices below #9 (for $w_c$=100 µm), #8 (125 µm), and #5 (150 µm), corresponding to $f^*_{gap}$ values of 1.92×10$^{-4}$ 1.76×10$^{-4}$ and 1.28×10$^{-4}$, respectively. FIG. 12-A demonstrates a difference between platelets flowing through devices #4 and #5, showing at the transition between a lossless degree of filtration and an excessive degree of filtration took place around device #5 (with $w_c$=150 µm and d=150 µm). The platelets were not observed to be present in the inter-obstacle gaps in the left-side panel (device #4) but are observed in the right-side panel (device #5), which indicates $f_{gap}$ had become larger than desirable in device #5.

Example 3A

Enriching Platelets in a PRP Suspension after Sedimentation of RBCs

Figure 9:
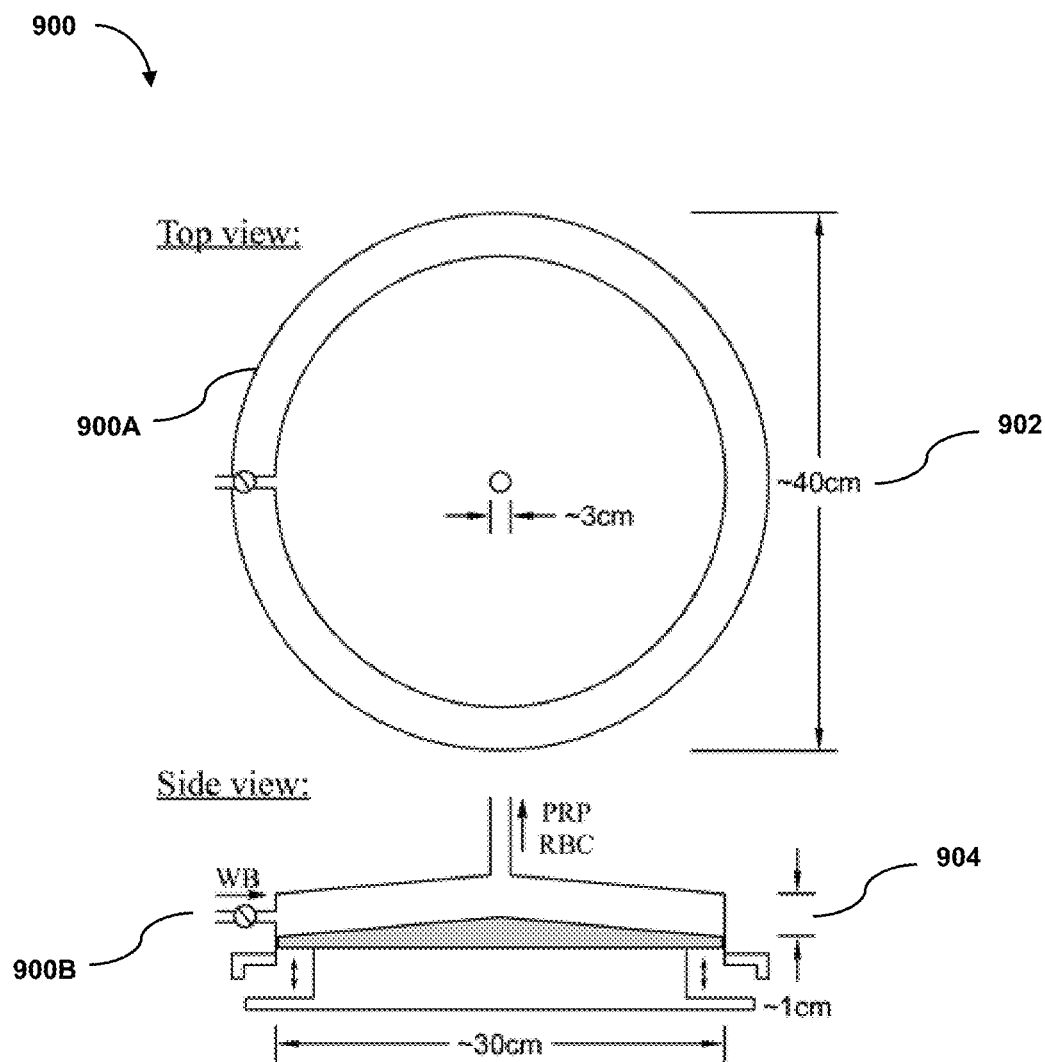
FIG. 9 shows an exemplary Stage 1 module for separating a 500 mL unit of WB into RBCs and PRP using 1×g sedimentation.

The guiding values for $w_c$ and $f_{gap}$ established for bead and platelet enrichment in Examples 2A, 2B were used to design a longer CIF device, via eqs. 1 and 2 above, with the goal of filtering a desired amount of plasma out of a sample of PRP while retaining PC in the central channel for collection. The CIF device thus designed was used in conjunction with the following sedimentation process for separating WB into RBCs and platelet-rich plasma (PRP). Sedimentation dynamics were compared for 3 mL volumes of fresh, human WB [Hematocrit (HCT)=0.42; Platelet count (PLT)=409×10$^3$/µL] in cylindrical vessels with different inner diameters (corresponding WB column heights: 40, 17 and 8 mm). RBCs in the short/wide 8 mm column achieved sedimentation in about 35 minutes, and the 17 mm-high column had nearly finished sedimentation in 60 minutes, while the tall/narrow 40 mm column continued to settle, as depicted in FIG. 7A and as graphed in FIG. 7B. In all three vessels, packed RBCs had HCT of ~0.7 and PLT ranging from 83–123×10$^3$/µL (lower than WB). The layer of PRP had PLT within 1,093–1,174×10$^3$/µL, which implies that platelets were being actively extruded from the layer of packed RBCs during sedimentation. FIG. 9 is a schematic showing a wide aspect ratio vessel 900, including a width 902 and a depth 904. This example demonstrates that 500 mL of WB can be completely separated at 1×g into packed RBCs and PRP in less than 60 minutes, if WB is spread into an about 10 mm-high cylindrical column in a vessel with a diameter of about 25 cm, as shown in FIG. 9.

Figure 8:
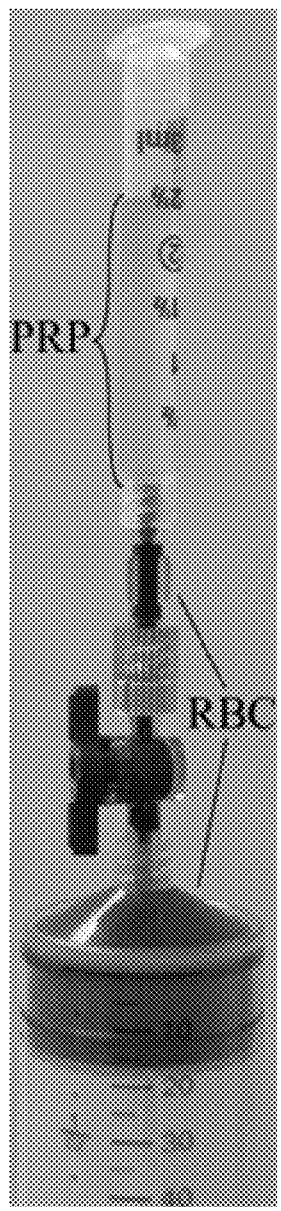
FIG. 8 depicts an exemplary PRP layer expressed into a 3 mL syringe after 55 minutes of sedimentation.

Additional experiments were performed using a modified 140 mL syringe on 8 mL volumes (~10 mm column height) of WB from 7 different donors (4 female, 3 male). The parameters of WB among the subjects varied significantly (HCT=0.42±0.02, PLT=220±96×10$^3$/µL, platelet activation 3.8%). For each experiment, after 55 min of sedimentation, the PRP layer was expressed into a 3 mL syringe, as shown in FIG. 8. The average HCT of the resultant packed RBC fractions was 0.67±0.06 and the supernatant PRP had platelet activation of ~5% and a mean PLT value of 552±174K/µL, corresponding to a 2.5-fold enrichment. No hemolysis was observed.

Example 3B

Design of a Device for Sedimentation of RBCs

The dependence of sedimentation time $T_s$ and HCTRBC (HCT of the RBC fraction) on the height of the WB column were measured. The heights of test WB columns were varied between 5 mm to 15 mm in cylindrical vessels using 10 mL volumes of fresh WB collected from consenting volunteers (n=10, male and female to capture the inter-gender differences of RBC sedimentation). The dependence of $T_s$ and HCTRBC on the shape of the sedimentation vessel for a given WB column height of either 5 mm, 10 mm, or 15 mm using vessels shaped as a traditional cone or inverted cone with the opening angle of the cone ranging from 30° to 180° were quantified. Cone-shaped vessels were fabricated by casting appropriately shaped molds produced using a 3D prototype printer in silicone elastomer (Rhodorsil V-1082, condensation-cure PDMS with a tin-based catalyst, Bluestar Silicones, York, S.C.). In one example, the Stage 1 device module was fabricated via standard injection molding techniques and sterilized using gamma radiation. The Stage 1 module was capable of accepting donated WB directly or from a standard blood collection bag. The Stage 1 module initiated the RBC separation immediately upon filling.

Example 3C

Products of RBC Sedimentation

After $T_s$~60 minutes at rest in normal gravity, whole blood passively separated into components with packed RBCs on the bottom and a PRP overlayer. The PRP was expressed out of the top of the slightly tapered device after RBC sedimentation was complete to minimize mixing of the biphasic solution after sedimentation. The PRP was directed to a CIF-based device for further processing as described in Example 3D. The heavier, more viscous RBC layer was expressed into a standard blood bag for hypothermic storage.

Example 3D

PRP Enrichment Using the CIF Device

In the second step of CIF device design for the platelet enrichment application, the three threshold values of $f_{gap}$ found in step one from Example 2A, 2B above were used to pattern complete devices for each of the corresponding central channel widths. Associated final side-channel widths were selected to produce the desired level of particle enrichment after a single pass through a given device. Approximately 70% of the total volume of the input PRP was targeted for removal and the final side-channel widths were calculated using eq. 2 above such that the ratio of side-channel flow resistance to center channel flow resistance produced the desired relative volumetric flow rates in each channel at the end of the device. Removing approximately 70% of the total volume of fluid from the input sample was expected to increase the particle count in the main channel by about 3.33 times, if no particles were lost with the removed fluid. FIG. 12-B shows the three complete devices to scale, generated by software written according to the modeling approach described above, with the flow path of each device incorporating several turns to fit onto a standard 4" wafer via photolithography. Each turn may include appropriate modification of the side channel widths through the course of the turn effective to avoid by an inner channel of the turn having a shorter overall path length (and thus resistance) than a channel further from the focal point of the turn.

The smaller the value of $f^*_{gap}$, the longer the device must be to achieve a desired total amount of filtration. For this example, a 125 µm wide central channel with a $f^*_{gap}$ value of $1.76 \times 10^{-4}$ was selected as optimal after considering also the increased throughput which generally accompanies a higher value of $w_c$. An application having desired particles of much smaller effective size would be expected to use a more conservative filtration fraction per gap. FIG. 12-C shows a representative image of the output of the device created based on these parameters. The input platelet count (PLT) was 354K/µL, the combined output PLT value of the side channels was 68K/µL, and the central channel output was 999K/µL. These results demonstrate that the PLT of the sample was increased ~3-fold, with very little loss (<15%) of platelets to the side channels.

Example 4

Retaining Beads of a Defined Size in the Central Channel

A device was created with a 125 µm wide central channel with an $f_{gap}$ value of $4.52 \times 10^{-4}$ and channel depths of 150 µm to demonstrate concentration of particles above a certain size within an overall complex mixture. The device was patterned with the width of the side channels increasing to 2.5× the central channel along the flow path, corresponding to a flow rate ~5× higher than the central channel. Beads with a diameter of 8.3 µm were added to a PRP suspension and run through the device, resulting in ~90% removal of the original volume of fluid.

FIG. 13 shows the schematic of the device and a representative image of the flow into output collection channels. This example shows that the platelets, which are typically under 4 µm in diameter, were pulled into the side/filtration channels, while the larger 8.3 µm beads were maintained in the central/concentration channel, consistent with the step one test results shown in FIG. 11. Thus, larger particles were more heavily concentrated using the CIF approach in the same device footprint according to the corresponding larger value of $f^*_{gap}$ relative to the smaller platelets. This example demonstrates that size-specific subpopulations can be enriched out of a mixture of variously-sized particles using a CIF-based device. Several such devices may be employed in series to effect a more complex selective removal or enrichment of a desired range of particle sizes, for example, to separate or concentrate particles in a range, e.g., above 3 µm and below 10 µm.

Example 5

Input Design of a CIF Device to Facilitate Large-Scale Manufacture

The side-channel width at the beginning of a CIF device may be designed to begin very close to, or at, zero. The device shown in FIG. 13-B has an initial side channel width of ~8 µm. However, such an initial width may undesirably divert particles desired for concentration into the side channels. In practice, micro-device construction via photolithography or other methods may be limited by the smallest feature size within the design. It may be useful to make the minimum feature size as large as possible to facilitate device manufacture. In general, larger minimum feature sizes increase the depth of the channels which can be feasibly fabricated. This may correspond to an upper practical limit to an aspect ratio of a microdevice, according to the technical constraints of both master mold fabrication and the ability to reliably extract parts molded of substrates such as PDMS, thermoplastic, etc. from the mold.

In one example of increasing the minimum feature size of a CIF device, the design considerations may be adapted at the input of the device by adjusting the length of the side-channel, rather than its width (which is the case described in preceding Examples). This is shown in FIG. 1-K for one particular CAD design. Here, eq. 1 was used to determine the side channel dimensions at each filtration point. The side channel width was initially set to be equal to the gap size of the designed array. Progressive decreases in side channel resistance were achieved by decreasing the total side channel length at each filtration point at every other gap in the device architecture. Analogous to the width-dependent calculation described in preceding Examples, a small amount may be iteratively subtracted from an initial value of the side channel length. The initial length was set at a large value relative to the central channel dimensions to provide a minimal amount of fluid flow into the side channels at the first opening. The small amount was iteratively subtracted from the initial value of the side channel length until the value of the side channel resistance calculated in eq. 2 satisfies eq. 1. This process was repeated at each filtration point. The custom-written software constructed the side channel of the calculated length by drawing a side channel that directs its fluid flow first away from, and then back toward, the main flow of the device, as shown in Figure XYZ. More advanced formulation of eq. 2 may facilitate an accurate estimate of side channel resistance, considering the non-linearity of the side channel geometry. This approach may be encoded in the CIF device design software to take place at the start of a device until the calculated side channel segment length is no larger than the corresponding central channel segment length. After that point in the CIF design process, the side channel widths would be allowed to progressively increase, as described in the above Examples.

Prophetic Example 6

Design of a CIF Device with Decreasing Central Channel Width

In some applications or embodiments, it may be desirable to also progressively decrease the central channel width while increasing the side channel width. This may be done either while maintaining the total device width or not. This type of modified approach and similar formulations can be encoded into software for subsequent CAD drawing and device manufacture by employing the same incremental calculations described for the constant width central channel examples described above.

Prophetic Example 7

Separation of Whole Blood

Whole blood is drawn from a donor directly into a flexible reservoir, e.g., flexible reservoir 1104, containing standard, approved anticoagulant (e.g. CPD, CP2D), using standard phlebotomy techniques. Alternatively, whole blood is introduced into the flexible reservoir after having already being drawn into a standard-sized blood bag+anticoagulant. The volume of whole blood may be 450-500 mL and the volume of standard anticoagulant may be about 70 mL. The dimensions of the flexible reservoir are chosen with a large surface area on a side such that the 'height' of the reservoir when laid on the large surface area side is in the range of 5-15 mm when the flexible reservoir is filled with the WB+anticoagulant. A conventional blood bag is a suitable example of flexible reservoir 1104. An input line of the flexible reservoir may be sealed off, e.g., using a standard blood bag tubing sterile sealing device. The flexible reservoir is placed between, e.g., a base substrate 1108 and a compression substrate 1112 within compression stage 1102 and pressurized.

A suitable pressure may be determined empirically by the flowrate desired while later expressing the PRP through any downstream devices and corresponding approximate fluidic resistance that may be attached to the system; e.g., a platelet-concentrating CIF device, such as CIF device 100. After a period of initial sedimentation time, the WB begins separating into a biphasic solution of PRP supernatant and packed RBC subnatant.

An output valve of the flexible reservoir, such as a conventional blood bag 'snap valve' is opened, allowing the PRP to begin flowing through downstream devices in the system. The sedimentation time may depend on several factors such as the height of the blood/reservoir and the propensity of the donor's blood to form rouleaux. Some visible separation of the WB into two phases may be expected in most WB samples within about 1-2 hours. Further sedimentation of the RBC layer may be allowed to occur as the PRP is being expressed out of the top of the flexible reservoir. Removal of the PRP from the flexible reservoir may take about 1 hr or more to complete, depending on the fluidic resistance of any devices that may be attached downstream.

In one example, the first device downstream of the flexible reservoir may be a standard PRP leukoreduction filter. In another example, the first device downstream of the flexible reservoir may be a CIF-style leukoreduction device that diverts WBCs into a satellite bag, allowing the leuko-reduced PRP to proceed further downstream to a platelet-concentrating device, e.g., a platelet-concentrating CIF-style device. In some examples, the leukoreduction stage may be omitted and the PRP may proceed directly to the platelet-concentrating device after exiting the flexible reservoir.

The platelet concentrating device may concentrate the platelets within the PRP into, e.g., ~35-100 mL of platelet concentrate. The remainder of the PRP volume may be largely free of platelets. The resultant PC and PPP may be collected into respective storage bags and sealed off after collection has completed, then placed in appropriate storage environments according to the contents of each storage bag.

A standard filter may be used remove residual platelets from the PPP if desired. An additive solution to promote healthy storage of the PC may be added to the PC storage bag if desired.

After the PRP layer has been fully expressed from the flexible reservoir, a valve or clamp is used to divert the packed RBC subnatant layer to a tubing branch that connects the reservoir to a RBC storage bag. This may be accomplished manually or automatically, for example, using a photodiode to sense the much darker RBC layer being expressed into the output tubing.

In some examples, the RBC storage bag may contain a standard amount of FDA-approved additive solution (~110 mL of "AS-1", e.g.) which may be flowed into the large reservoir to lower the viscosity of the packed RBC layer. In such examples, the flexible reservoir may first be depressurized. The RBC+AS may be expressed out of the large reservoir through a LR filter or LR-CIF device (as above), which may require repressurization of the reservoir, or, e.g., hanging the reservoir at a height of 1-5 ft above the downstream devices, much as is done currently with standard WB processing through LR filters.

Once the RBC+AS solution has been fully collected into its storage bag, following any leukoreduction that may have been desired, the bag is sealed off and placed into an appropriate RBC storage environment.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the terms "operatively coupled" or "operatively connected" are used in the specification or the claims, it is intended to mean that the identified components are connected in a way to perform a designated function. To the extent that the term "substantially" is used in the specification or the claims, it is intended to mean that the identified components have the relation or qualities indicated with degree of error as would be acceptable in the subject industry.

As used in the specification and the claims, the singular forms "a," "an," and "the" include the plural unless the singular is expressly specified. For example, reference to "a compound" may include a mixture of two or more compounds, as well as a single compound.

As used herein, the term "about" in conjunction with a number is intended to include ±10% of the number. In other words, "about 10" may mean from 9 to 11.

As used herein, the terms "optional" and "optionally" mean that the subsequently described circumstance may or may not occur, so that the description includes instances where the circumstance occurs and instances where it does not.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The various aspects and embodiments disclosed herein are for purposes of illustration and are not intended to be limiting, with the true scope and spirit being indicated by the following claims.

The invention claimed is:

1. A passive compression sedimentation system, comprising:
   a compression stage configured to accept a flexible reservoir configured to contain a liquid mixture, the compression stage comprising:
      a base substrate comprising a first base face configured to contact a first face of the flexible reservoir, the first base face of the base substrate being within about ±10 degrees of perpendicular with respect to gravity; and
      a compression substrate comprising a first compression face configured to contact a second face of the flexible reservoir,
   the base substrate and the compression substrate together configured to apply a force to the flexible reservoir effective to create a pressure in the liquid mixture; and
   the passive compression sedimentation system configured effective to provide passive sedimentation of the liquid mixture in the flexible reservoir into a supernatant and a subnatant comprising a sediment.

2. The passive compression sedimentation system of claim 1, being configured effective to provide for passive sedimentation under normal gravity of the liquid mixture in the flexible reservoir into the supernatant and the subnatant comprising the sediment, the pressure in the liquid being effective to direct the supernatant through an output of the flexible reservoir after sedimentation has proceeded to a desired extent and a valve operatively coupled to the flexible reservoir is opened.

3. The passive compression sedimentation system of claim 1, the base substrate and the compression substrate together being:
   characterized by a separation between the first face and the second face; and
   configured to apply the force to the flexible reservoir over the separation effective to create the pressure in the liquid mixture, the separation comprising a range in millimeters of about one or more of: 5 to 15, 5 to 14, 6 to 13, and 6 to 12.

4. The passive compression sedimentation system of claim 1, the compression stage further comprising a chassis, the chassis configured to position the base substrate and the compression substrate together to compress the flexible reservoir between the base substrate and the compression substrate, the chassis comprising one or more mounts, the one or more mounts being configured to receive the base substrate, the compression substrate, and one or more force generators effective to permit compression of the flexible reservoir between the base substrate and the compression substrate according to a force applied by the one or more force generators.

5. The passive compression sedimentation system of claim 4, the chassis comprising one or more gas pass-through conduits configured to direct a gas to a gas spring, the one or more gas pass-through conduits each being operatively coupled to one or more of: a gas valve, a gas pressure source, and a pressure gauge.

6. The passive compression sedimentation system of claim 4, the chassis comprising one or more bases corresponding to the one or more mounts, the one or more bases being configured to receive the one or more mounts effective to position a lateral edge of the base substrate in an orientation normal with respect to gravity and a tangential edge of the base substrate in an orientation at an angle with respect to gravity such that the first end is slightly elevated compared to the second end, the angle being a range of about 0 degrees to about 10 degrees.

7. The passive compression sedimentation system of claim 4, the one or more force generators comprising one or more gas springs, further comprising a pressure gauge operatively coupled to indicate the pressure within the one or more gas springs.

8. The passive compression sedimentation system of claim 4, the one or more force generators comprising one or more of: a gas spring, a mechanical spring, a clamp, a hydraulic actuator, a magnetic actuator, a piezoelectric actuator, and a weight.

9. The passive compression sedimentation system of claim 1, further comprising a level indicator operatively coupled to indicate an orientation of one or more of: the lateral edge of the base substrate with respect to gravity and the tangential edge of the base substrate with respect to gravity.

10. The passive compression sedimentation system of claim 1, one or more of the base substrate and the compression substrate defining at least one via, the at least one via configured to provide access through one or more of the base substrate and the compression substrate to one or more of the output of the flexible reservoir and an input of the flexible reservoir.

11. The passive compression sedimentation system of claim 1, the base substrate and the compression substrate together being configured to contact the flexible reservoir in the form of a blood bag.

12. An apparatus configured to separate whole blood (WB), comprising:
   a passive sedimentation system configured for passive sedimentation of the WB into a supernatant comprising platelet rich plasma (PRP) and a subnatant comprising red blood cells (RBC), the passive sedimentation system configured to accept a flexible reservoir configured to contain a liquid mixture, the passive sedimentation system comprising a base substrate comprising a first base face configured to contact a first face of the flexible reservoir, the first base face of the base substrate being within about ±10 degrees of perpendicular with respect to gravity; and
   at least one platelet-concentrating device operatively coupled to the passive sedimentation system to receive the supernatant comprising the PRP, the platelet-concentrating device being configured to separate a platelet concentrate (PC) and a platelet poor plasma (PPP) from the supernatant comprising the PRP.

13. The apparatus of claim 12, the platelet-concentrating device comprising one or more of: a filter, a centrifuge, an electrophoresis device, a chromatography column, a fluid evaporator, a sedimentation device, a deterministic lateral displacement device, a plasma skimmer, a microfluidic crossflow filtration device, a pinched flow fraction device, a hydrodynamic filtration device, a tubular pinch device, a Dean flow fractionation device, a margination device, a magnetic separator, an ultrasound focusing device, and a density gradient separator.

14. The apparatus of claim 12, further comprising one or more leukocyte reduction stages operatively coupled to the passive sedimentation system to receive the subnatant, the one or more leukocyte reduction stages configured to remove at least a portion of leukocytes comprised by the subnatant.

15. The apparatus of claim 12, the passive sedimentation system comprising one or more of: a passive compression sedimentation system and a passive gravity sedimentation device.

16. The apparatus of claim 12, the passive sedimentation system comprising a passive compression sedimentation system, comprising:
a compression stage configured to accept a flexible reservoir configured to contain a liquid mixture, the compression stage comprising:
a base substrate comprising a first base face configured to contact a first face of the flexible reservoir, the first base face of the base substrate being within about ±10 degrees of perpendicular with respect to gravity; and
a compression substrate comprising a first compression face configured to contact a second face of the flexible reservoir,
the base substrate and the compression substrate together configured to apply a force to the flexible reservoir effective to create a pressure in the liquid mixture; and
the passive compression sedimentation system configured effective to provide sedimentation of the WB in the flexible reservoir into the supernatant comprising the PRP and the subnatant comprising the RBCs, the sedimentation comprising passive sedimentation under gravity.

17. A method for compression sedimentation, comprising:
providing a flexible reservoir comprising a liquid mixture, the liquid mixture comprising two or more particulate distributions, the two or more particulate distributions characterized by one or more of: different effective average particulate diameters and different densities; and
passively sedimenting the liquid mixture in the flexible reservoir to form a supernatant and a subnatant, the passively sedimenting comprising using a flat substrate, the flat substrate being perpendicular to gravity within about ±10 degrees,
the supernatant comprising at least a first particulate distribution characterized by one or more of a first effective average particulate diameter and a first particulate density; and
the subnatant comprising at least a second particulate distribution characterized by one or more of a second effective average particulate diameter and a second particulate density.

18. The method of claim 17, the liquid mixture comprising whole blood, passively sedimenting the whole blood comprising forming the supernatant comprising platelet rich plasma (PRP) and forming the subnatant comprising red blood cells (RBC).

19. The method of claim 17, further comprising pressurizing the flexible reservoir comprising one or more of: the liquid mixture, the supernatant, and the subnatant, pressurizing comprising compressing the flexible reservoir between two substrates using one or more of: gas pressure, a gas spring, a mechanical spring, a clamp, a hydraulic actuator, a magnetic actuator, a piezoelectric actuator, and a weight.

20. The method of claim 17, further comprising directing one or more of the supernatant and the subnatant through the output of the flexible reservoir, the directing comprising placing a first end of the flexible reservoir proximal to the output at a higher elevation with respect to gravity compared to a second end of the flexible reservoir distal to the output.

21. The method of claim 17, further comprising one or more of:
directing the supernatant through the output of the flexible reservoir into a storage reservoir;
contacting the subnatant with a storage additive;
directing the storage additive and the subnatant through the output of the flexible reservoir to a storage reservoir; and
storing the additive and the subnatant together in the flexible reservoir for a period of time.

22. A method for separation of whole blood (WB), comprising:
providing a flexible reservoir comprising the WB;
pressurizing the flexible reservoir comprising one or more of the WB, the supernatant comprising the PRP and the subnatant comprising the RBCs to a pressure; and
sedimenting the WB in the flexible reservoir for a period of time to form a supernatant comprising a platelet rich plasma (PRP) and a subnatant comprising red blood cells (RBCs) the sedimenting comprising using a flat substrate, the flat substrate being perpendicular to gravity within about ±10 degrees;
using the pressure to direct one or more of the supernatant comprising the PRP and the subnatant comprising the RBCs to a secondary separation process, thereby separating the WB.

23. The method of claim 22, one or more of:
the WB characterized being characterized by a WB platelet activation value and the supernatant comprising the PRP being formed characterized by a PRP platelet activation value, the PRP platelet activation value being a percentage of the WB platelet activation value of less than one or more of about: 150, 145, 140, 135, 130, 125, 120, 115, 110, 105, 104, 103, 102, 101, and 100;
the WB being characterized by a WB platelet activation value and the PC being formed characterized by a PC platelet activation value, the PC platelet activation value being a percentage of the WB platelet activation value of less than one or more of about: 150, 145, 140, 135, 130, 125, 120, 115, 110, 105, 104, 103, 102, 101, and 1; and
the WB characterized by a WB platelet activation value and the leukocyte-depleted supernatant comprising the PRP being formed characterized by a leukocyte-depleted PRP platelet activation value, the leukocyte-depleted PRP platelet activation value being a percentage of the WB platelet activation value of less than one or more of about: 150, 145, 140, 135, 130, 125, 120, 115, 110, 105, 104, 103, 102, 101, and 100.

24. The method of claim 22, operating the secondary separation process on the supernatant comprising the PRP to form a platelet concentrate (PC) and a platelet poor plasma (PPP).

25. The method of claim 22, the supernatant comprising the PRP and leukocytes, the method comprising removing at least a portion of the leukocytes from the supernatant to form a leukocyte-depleted supernatant comprising the PRP.

26. The method of claim 25, the removing at least a portion of the leukocytes from the supernatant comprising contacting the supernatant comprising the PRP and the leukocytes to one or more of: a leukocyte filter and a leukocyte-reducing microfluidic crossflow filtration device.

27. The method of claim 22, the subnatant comprising the RBC and leukocytes, the method comprising removing at least a portion of the leukocytes from the subnatant to form a leukocyte-depleted subnatant comprising the RBC.

28. The method of claim 27, removing at least a portion of the leukocytes from the subnatant comprising contacting the subnatant comprising the PRP and the leukocytes to one or more of: a leukocyte filter and a leukocyte-reducing microfluidic crossflow filtration device.

29. The method of claim 22, the sedimenting the WB in the flexible reservoir to form the supernatant and the subnatant being conducted for a time in minutes of less than about one or more of: 180, 120, 90, 80, 70, 60, 50, 40, 30, 25, 20, 15, 10, 5, and 1.

30. The method of claim 22, further comprising one or more of:
    directing the subnatant comprising the RBC through the output of the flexible reservoir into a storage reservoir;
    contacting the subnatant comprising the RBC with a RBC storage additive;
    contacting a RBC storage additive to the subnatant comprising the RBC in the flexible reservoir;
    directing the RBC storage additive and the subnatant comprising the RBC through the output of the flexible reservoir to a storage reservoir; and
    storing the RBC additive and the subnatant comprising the RBC together in the flexible reservoir for a period of time.

* * * * *